(12) United States Patent
Podolyan et al.

(10) Patent No.: US 11,578,013 B2
(45) Date of Patent: Feb. 14, 2023

(54) NITRIFICATION INHIBITORS

(71) Applicant: Lincoln University, Hamilton (NZ)

(72) Inventors: Andriy Podolyan, Hamilton (NZ); David Rennison, Hamilton (NZ); Gregory Cook, Hamilton (NZ); Hong Jie Di, Hamilton (NZ); Keith Craig Cameron, Hamilton (NZ); Margaret Anne Brimble, Hamilton (NZ); Scott Ferguson, Hamilton (NZ); Robert Starr Ronimus, Hamilton (NZ); Vincenzo Carbone, Hamilton (NZ)

(73) Assignee: Lincoln University, Hamilton (NZ)

( * ) Notice: Subject to any disclaimer, the term of this patent is extended or adjusted under 35 U.S.C. 154(b) by 0 days.

(21) Appl. No.: 17/665,243

(22) Filed: Feb. 4, 2022

(65) Prior Publication Data
US 2022/0153655 A1 May 19, 2022

Related U.S. Application Data

(63) Continuation of application No. PCT/NZ2021/050085, filed on May 25, 2021.

(30) Foreign Application Priority Data

May 25, 2020 (NZ) .................................. 764712
May 26, 2020 (NZ) .................................. 764783
(Continued)

(51) Int. Cl.
*C05G 3/90* (2020.01)
*B09C 1/08* (2006.01)
(Continued)

(52) U.S. Cl.
CPC ................. *C05G 3/90* (2020.02); *B09C 1/08* (2013.01); *C02F 1/68* (2013.01); *C05C 3/00* (2013.01);
(Continued)

(58) Field of Classification Search
None
See application file for complete search history.

(56) References Cited

U.S. PATENT DOCUMENTS 3,533,774 A 10/1970 Nault et al.
3,778,441 A * 12/1973 Burckhardt .......... C07D 215/40
546/171
(Continued)

FOREIGN PATENT DOCUMENTS

WO WO 2016/070184 A1 5/2016

OTHER PUBLICATIONS

G.W.McCarty and J.M. Bremner, "Inhibition of Nitrification in Soil by Acetylenic Compounds", Soil Sci. Soc. Am. J., vol. 50, pp. 1198-1201 (1986).*
(Continued)

*Primary Examiner* — Wayne A Langel
(74) *Attorney, Agent, or Firm* — Knobbe, Martens, Olson & Bear, LLP

(57) ABSTRACT

Nitrification inhibitors and uses of same to prevent nitrate leaching or nitrous oxide emissions as well as increase pasture or crop production. The nitrification inhibitors and formulations including same may be used for direct or indirect application to soil or pasture.

13 Claims, 22 Drawing Sheets

(30) Foreign Application Priority Data

| May 29, 2020 | (NZ) | 764780 |
| Jun. 8, 2020 | (NZ) | 765203 |
| Jun. 8, 2020 | (NZ) | 765211 |
| Jun. 9, 2020 | (NZ) | 765239 |
| Dec. 14, 2020 | (NZ) | 771062 |
| Apr. 9, 2021 | (NZ) | 774851 |
| Apr. 12, 2021 | (NZ) | 774955 |

(51) Int. Cl.

| C02F 1/68 | (2006.01) |
| C05C 3/00 | (2006.01) |
| C05C 9/00 | (2006.01) |
| C07D 237/14 | (2006.01) |
| C07D 239/34 | (2006.01) |
| C07D 241/18 | (2006.01) |
| C02F 103/20 | (2006.01) |

(52) U.S. Cl.
CPC ............. *C05C 9/00* (2013.01); *C07D 237/14* (2013.01); *C07D 239/34* (2013.01); *C07D 241/18* (2013.01); *C02F 2103/20* (2013.01)

(56) References Cited

U.S. PATENT DOCUMENTS

| 4,552,581 A | 11/1985 | Bremner | |
| 11,124,462 B1* | 9/2021 | Hocking | C07F 9/224 |
| 2017/0036969 A1* | 2/2017 | Nave | C07D 311/22 |
| 2020/0024205 A1* | 1/2020 | McKnight | C05C 3/00 |
| 2021/0047192 A1* | 2/2021 | Nave | C07C 205/38 |
| 2021/0053888 A1* | 2/2021 | Nesvadba | A01N 43/58 |

OTHER PUBLICATIONS

Sharma et al, Synthesis and Evaluation of some Pyrazoles for N-regulation of Soil-applied Urea in Rice-Wheat Culture, Pesticide Research Journal, vol. 18 (1): 7-11 (Jun. 2006).*

International Search Report in PCT/NZ2021/050085 dated Jul. 23, 2021.

Di, H.J., et al., "How does the application of different nitrification inhibitors affect nitrous oxide emissions and nitrate leaching from cow urine in grazed pastures?", Soil Use and Management. 2012, vol. 28, pp. 54-61.

* cited by examiner

A

C

D

A

B

A

B

A

B

C

D

B

C

D

C

A

B

C

D

E

F

NITRIFICATION INHIBITORS

BACKGROUND OF THE INVENTION

Field of the Invention

The present invention relates to improvements in and relating to nitrification inhibitors.

Description of the Related Art

The present invention relates to a global problem concerning negative effects upon the environment which are a by-product of modern farming.

In particular, nitrate ($NO_3^-$) leaching occurring as a result of intensive agricultural land use, such as in livestock production systems, cropping systems, and intensive horticultural systems, has been shown to be a major cause of water contamination in ground water, rivers and lakes, and is indeed a major global environmental problem.

Furthermore, nitrous oxide ($N_2O$) is a potent greenhouse gas with long-term global warming potential 298 times more powerful than $CO_2$.

In grazed pasture lands most of the $N_2O$ and $NO_3^-$ comes from nitrogen (N) returned to the land via excreta particularly urine from the grazed animals which can have a N loading of about 300 kg to 1000 kg N ha$^{-1}$. Most of the N in animal urine is urea $(NH_2)_2CO$ and upon entering the soil is quickly hydrolysed to plant available ammonium ($NH_4^+$) via the enzyme urease as per the equations below (Tisdale et. al. 1985):

$$(NH_2)_2CO + H_2O + \text{urease} \rightarrow NH_3 + H_2NCOOH \rightarrow 2NH_3 \text{ (gas)} + CO_{2\,gas}) \quad NH_{3\,(gas)} + H_2O \rightarrow NH_4^+ + OH^-$$

and then nitrification occurs via microbes including species of the genera Nitrosornonas, *Nitrosospira, Nitrosococcus, Nitrobacter* and *Nitrococcus* where $NH_3$ is oxidized to hydroxylamine ($NH_2OH$) and then into nitrite ($NO_2$) and nitrate ($NO_3^-$) in order to derive energy (Di and Cameron 2016).

Keeping the N in the form of $NH_4^+$ is also beneficial as the top layer of soil colloids are negatively charged and thus help hold the positively charged $NH_4^+$ ions in situ. This would reduce nitrogen leaching. Nitrate which is negatively charged is not strongly retained by the soil colloids and is thus easily leached whenever there is drainage through the soil (Di and Cameron 2016).

Furthermore, keeping the nitrogen in the ammonium form by slowing down the nitrification process is also beneficial for reducing the greenhouse gas nitrous oxide ($N_2O$) emissions, as $N_2O$ is predominantly produced from nitrification (the oxidation of ammonia to nitrate, known as nitrification) and denitrification (the reduction of nitrate to gaseous forms, including $N_2O$).

Therefore, one effective way to reduce both nitrate leaching and nitrous oxide emissions in agricultural soils is to slow down or stop the nitrification process as it is the nitrification process that leads to the production of nitrate that can be leached and leads to the production of $N_2O$.

Previous research has shown that both nitrate leaching and nitrous oxide emissions can be reduced by inhibiting the nitrification process (Di and Cameron, 2016).

$$NH_3 + O_2 + 2H^+ + 2e^- \xrightarrow{\text{Ammonia Monooxygenase (amoA)}} NH_2OH + H_2O \quad (2)$$

$$NH_2OH + H_2O \xrightarrow{\text{Hydroxylamine oxidoreductase}} NO_2^- + 5H^+ + 4e^- \quad (3)$$

$$2NO_2^- + O_2 \xrightarrow{\text{Nitrite oxydoreductase}} 2NO_3^- \quad (4)$$

Furthermore, in agricultural land $NO_3^-$ can also come from nitrogen fertilisers such as urea which is hydrolysed in the soil to produce ammonia/ammonium; the ammonium from the nitrogen fertilizer can be nitrified to produce nitrate in the soil in a similar way as the ammonium from the animal urine in the soil.

Research over the last two decades has clearly demonstrated that $N_2O$ emissions and nitrate leaching can be effectively reduced by the use of nitrification inhibitors to treat grazed pasture soils where animal urine patches are deposited, or nitrogen fertilisers are applied—(see for example Di and Cameron, 2002; de Klein et al., 2011; Dai et al., 2013).

NZ Patent 520549 teaches a soil treatment method which applies a nitrification inhibitor in solution and/or fine particle suspension form to cover substantially the whole of the pasture to reduce among other things nitrate leaching and nitrous oxide emissions.

In particular, NZ 520549 teaches the use of dicyandiamide (DCD) as a nitrification inhibitor to treat soil. DCD was selected as a preferred nitrification inhibitor for commercial agricultural use—as of all the known nitrification inhibitors—DCD was:

partially soluble and therefore both easy and cost effective to deliver to a pasture system; and
importantly not toxic.

DCD is rated 10 times less toxic than table salt.

For example, another well-known commercially used nitrification inhibitor, DMPP (3,4-Dimethylpyrazole phosphate) has oral lethal dose ($LD_{50}$) in rats ranging from 300 to 2,000 mg kg$^{-1}$ body weight, compared with an oral $LD_{50}$ of greater than 30,000 mg kg$^{-1}$ body weight of female rats for DCD. Hence, why DCD was the preferred nitrification inhibitor in NZ 520549.

However, the use of DCD as a nitrification inhibitor in New Zealand ceased in 2013 due to the risk of detection of DCD in milk products and the lack of an international standard for DCD residues in food. This risk was partly a result of the relatively high rates of DCD application (i.e. 10 kg/ha) to achieve the desired environmental outcomes.

There therefore remains a clear need for other nitrification inhibitors as alternatives to replace DCD which:

are low in toxicity, high in efficacy (thus low rates of application), and present no food safety concerns, and
can be easily, and cost effectively applied to farmland, to reduce the adverse environmental impact of nitrates and nitrous dioxide caused by modern farming, mentioned above.

There is also a need for nitrification inhibitors which are not volatile (or low in volatility); not flammable; otherwise, non-hazardous; or not unsafe to manufacture or handle.

There is also a need for new nitrification inhibitors to help guard against the effectiveness of known nitrification inhibitors potentially decreasing due to continued long-term use.

In addition, there is also a need for different nitrification inhibitors as some may be better suited for different soil and environmental conditions.

In addition, there is a need for new compounds which can function as active ingredients in the field in relation to nitrification inhibitor formulations.

Importantly, to help feed the growing world population, there will likely to be an increase in intensity of farming, involving:

the increasing use of nitrogen fertilisers or other organic manures as nutrient sources; and
greater numbers of livestock around the globe.

Thus, the need for effective safe nitrification inhibitors will increase in order to mitigate the environmental impacts.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

Definitions

The term 'NNI' as used herein refers to a new nitrification inhibitor of the present invention which exhibits nitrification inhibition at the same, or preferably, a lower dosage rate than DCD.

The term 'sufficient quantity' as used herein refers to a dosage amount of an NNI to give the desired percentage of nitrification inhibition. The figures list possible dosage amounts, as examples, for the various NNIs outlined herein.

The term 'dosage quantity' as used herein refers to a defined amount of NNI which corresponds to the amount required to be applied:

to a defined area of land/plants in order to reduce nitrification and/or increase the amount of plant available nitrogen;
to a defined amount of nitrogen fertilizer to reduce nitrification rate of ammonium from the nitrogen fertilizer when applied to soil;
into a defined volume of liquid to ensure said liquid can inhibit the nitrification process should the liquid be re-applied to land and/or plants;
into a defined volume of farm effluent to inhibit the nitrification process should the effluent be re-applied to land and/or plants.

As a representative example only, 1 kg of NNI is a dosage quantity for 1 hectare of land/plants to be treated where the Nitrification Inhibitor is in the form of 2-Ethynyl 1,3 Diazine.

The term 'nitrogen efficiency' as used herein refers to ability for nitrogen to remain in the soil in a plant assimilable form.

The term 'N' when used on its own as a symbol (i.e., not as part of a chemical formula for a compound) represents the element nitrogen. It will be remembered that $NO_3^-$ is only temporarily available to plants as it is subject to nitrate leaching and, unlike $NH_4^+$, is not held by the negatively charged soil exchange surfaces in the soil.

The term 'agricultural land' as used herein refers to areas of land used for agricultural/horticultural purposes, including but not limited to: grazing pastures; or crop land; in relation to which the application of nitrogen is beneficial, or occurs as a consequence of the agricultural use of the land e.g. via animal urination, or N fertiliser application.

The term 'urban land' as used herein refers to areas of land such as parks, gardens, playing fields, and golf courses and the like where it is desirous to apply nitrogen to fertilise grass or plants growing or to be grown thereon.

The term 'urine patch' as used herein refers to an area of land which has been subjected to the deposit of animal urine thereon. The term 'urine patch' may include a specific patch of land upon which the urine was actually deposited by an animal urinating thereon, or may cover a defined area of land such as a paddock, or other bounded/demarcated area, where animals have been located for a period of time, during which, one or more of the animals may have urinated.

The term 'topsoil' as used herein refers to the top 0 cm to 30 cm of soil which has the highest concentration of organic matter and is where most of the soil biological activity occurs.

SUMMARY OF THE INVENTION

Having seen the fate of DCD (as outlined above) finding new environmentally and food safe commercially suitable nitrification inhibitors presents an unmet need in order to produce more food for a growing world population without polluting the planet.

Consequently, whilst in vitro laboratory testing can provide some initial indications as to possible candidate compounds that may have potential as nitrification inhibitors this provides no insight into whether the compound will function as a commercially useful nitrification inhibitor in the field.

Soil testing is the only definitive way to ascertain whether something has potential to be a nitrification inhibitor. It is therefore a time consuming and very expensive exercise to find new potential commercial nitrification inhibitors.

Depending on the destined use of the nitrification inhibitor, certain attributes of the nitrification inhibitor are preferred to other attributes. For example, a nitrification inhibitor that is water soluble would be easier to make into an aqueous solution for land application. Furthermore, a nitrification inhibitor with a lower volatility is preferred to one with a high volatility because low volatility improves storage and extends shelf life.

Known Commercially Accepted Nitrification Inhibitors

Despite all the research in this area to date there are only a handful of nitrification inhibitors which have been successfully commercialized which include:

DCD (aka dicyandiamide)

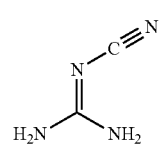

DMPP (aka 3,4-dimethylpyrazole phosphate)

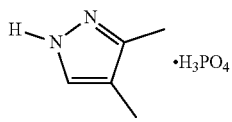

Nitrapyrin (aka 2-chloro-6-(trichloromethyl)pyridine)

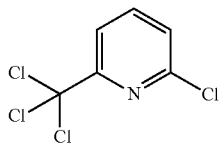 [SMILES: Clc1cccc(C(Cl)(Cl)Cl)n1]

DMPSA (aka 3 4-dimethylpyrazole succinic acid)

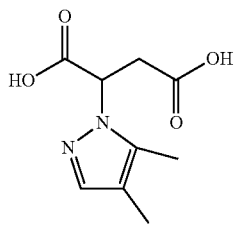

The diversity and contrast in chemical structure of these known commercially utilized nitrification inhibitors makes it impossible to predict what chemical structures will have desired nitrification inhibitor properties.

BRIEF DESCRIPTION OF THE DRAWINGS

Further aspects of the present invention will become apparent from the ensuing description which is given by way of example only and with reference to the accompanying drawings in which:

FIG. 16 shows the nitrate-N concentration in the soil at the end of 30 days of incubation, as affected by the application of 1,4-diethynylbenzene at 2 kg/ha, illustrating the highly efficient inhibition of nitrification by 1,4-diethynylbenzene, as shown by the lower nitrate-N concentrations in the urine+1,4-diethynylbenzene treated soil compared with

DETAILED DESCRIPTION OF THE PREFERRED EMBODIMENT

Broadest Aspects of the Present Invention

Figure 1:
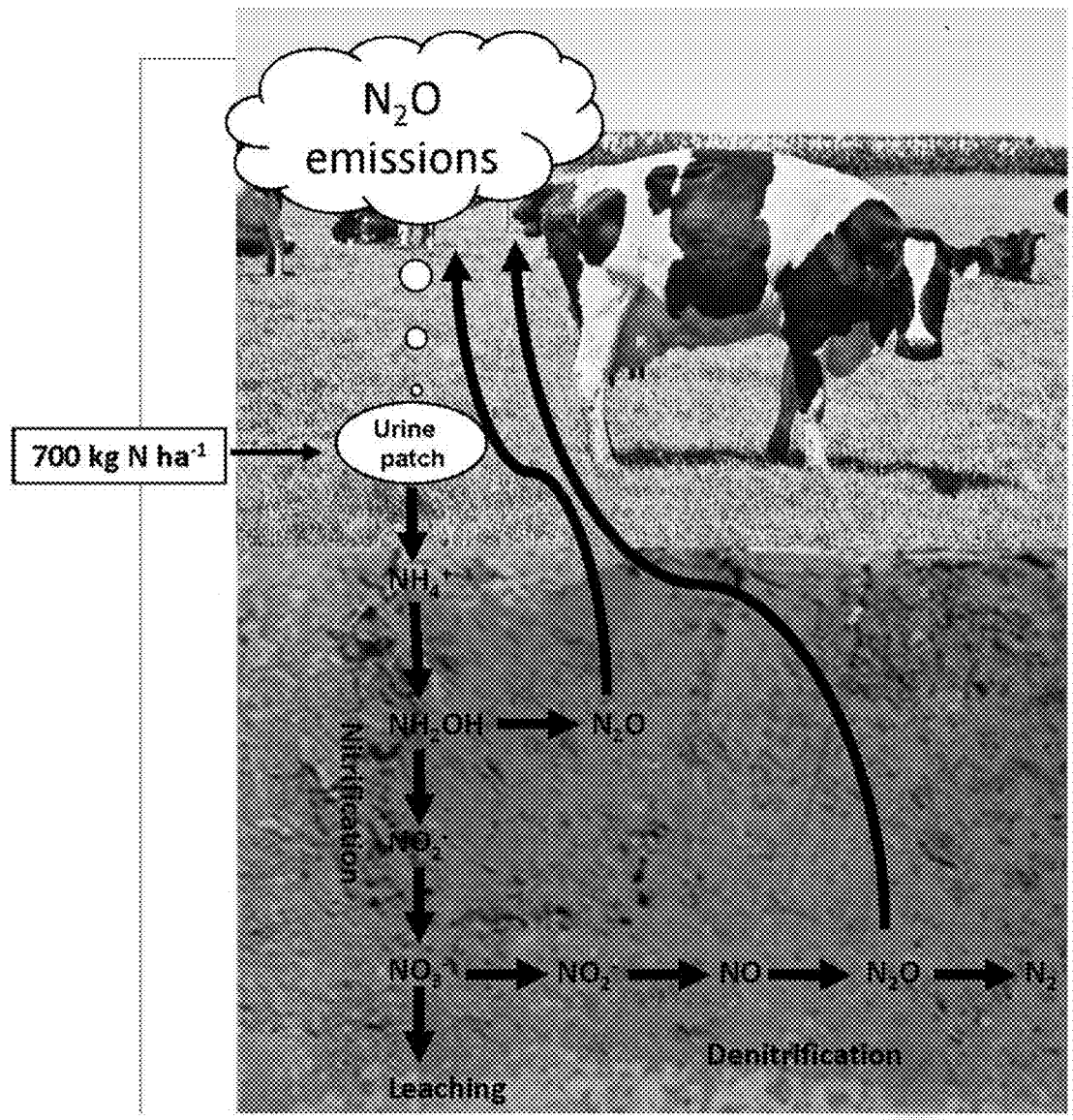
FIG. 1. (A) is a diagram illustrating the nitrification process and how nitrate leaching and the greenhouse gas $N_2O$ is formed in soil, and how nitrification inhibition by a nitrification inhibitor can reduce both nitrate leaching and nitrous oxide emissions (Di and Cameron 2016). (B) shows the nitrate-N concentration in the soil at the end of 30 days of incubation, as affected by the application of 2-Ethynyl 1,3 Diazine at 2 kg/ha, illustrating the highly efficient inhibition of nitrification by 2-Ethynyl 1,3 Diazine, as shown by the lower nitrate-N concentrations in the urine+2-Ethynyl 1,3 Diazine treated soil compared with the urine alone or urine+dimethyl sulfoxide (DMSO) control treatments. The error bars represent one standard error of the mean (SEM). (C) shows the nitrate-N concentration in the soil at the end of 30 days of incubation, as affected by the application of 2-Ethynyl 1,3 Diazine at 1 kg/ha, illustrating the highly efficient inhibition of nitrification by 2-Ethynyl 1,3 Diazine, as shown by the lower nitrate-N concentrations in the urine+2-Ethynyl 1,3 Diazine treated soil compared with the urine alone or urine+DMSO control treatments. The error bars represent one standard error of the mean (SEM). (D) shows the nitrate-N concentration in the soil at the end of 30 days of incubation, as affected by the application of 2-Ethynyl 1,3 Diazine at 0.5 kg/ha, illustrating the highly efficient inhibition of nitrification by 2-Ethynyl 1,3 Diazine, as shown by the lower nitrate-N concentrations in the urine+2-Ethynyl 1,3 Diazine treated soil compared with the urine alone or urine+DMSO control treatments. The error bars represent one standard error of the mean (SEM). (E) shows the effectiveness of 2-Ethynyl 1,3 Diazine in reducing $N_2O$—N emissions when 2-Ethynyl 1,3 Diazine was sprayed to soil surface with pasture in the field which had received animal urine. $N_2O$—N emissions in the urine+2-Ethynyl 1,3 Diazine treated soil were about 96% and 91% lower than that in the urine alone control treatment when 2-Ethynyl 1,3 Diazine was applied at 10 kg/ha and 2 kg/ha, respectively. This shows the efficiency of 2-Ethynyl 1,3 Diazine in reducing $N_2O$ emissions in the soil. The nitrous oxide reductions by 2-Ethynyl 1,3 Diazine were greater than that by DCD. The error bars in the figure represent one standard error of the mean (SEM).
Figure 1:
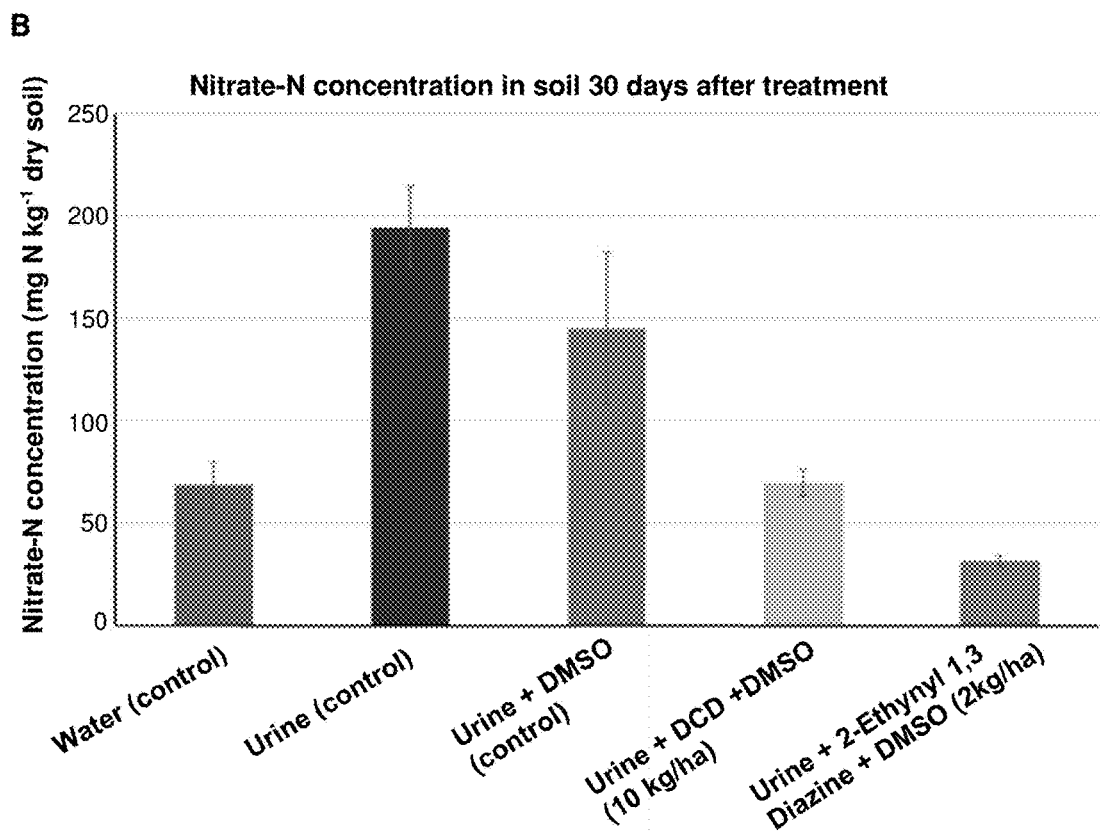
Figure 1:
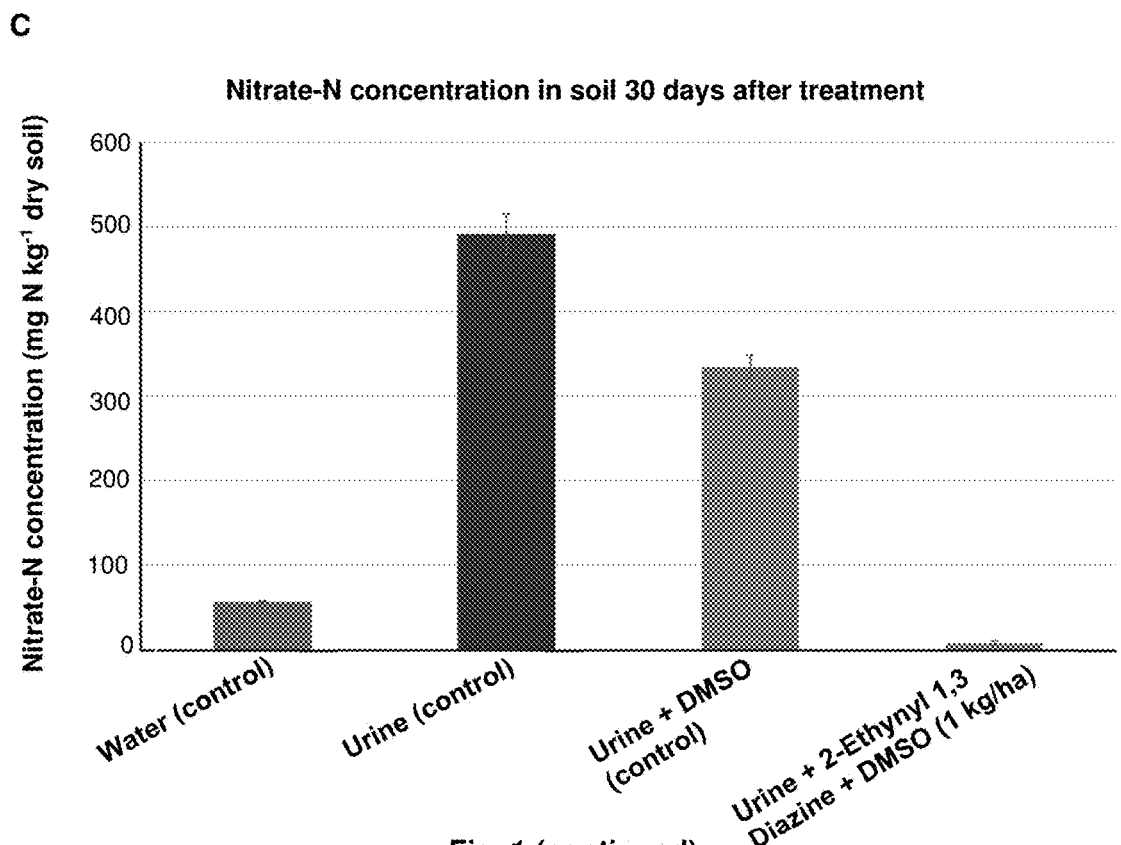
Figure 1:
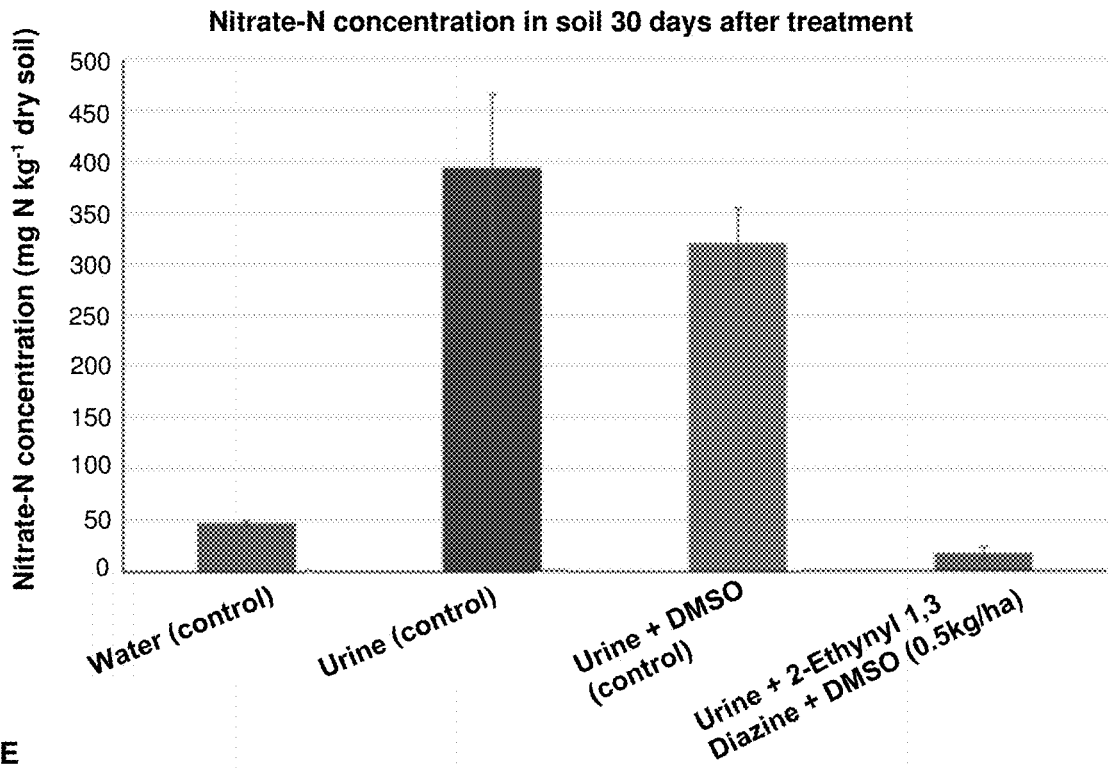
Figure 1:
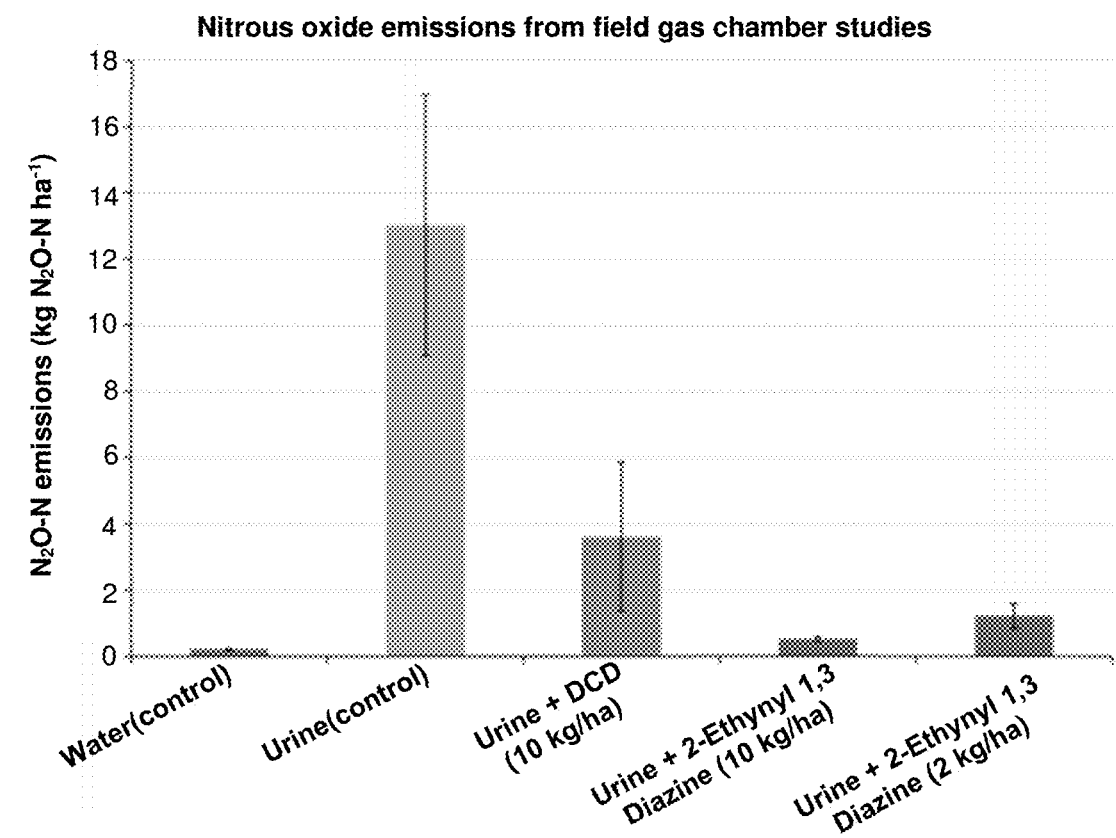

According to a first broad aspect of the present invention there is provided a use of a compound as a nitrification inhibitor selected from the group consisting of:

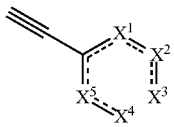

FORMULA 1 and
Pyrimidines
  wherein $X^1$ and $X^5$=N, $X^2$ and $X^4$=CH, and $X^3$=C—R; where R may be selected from H and OMe; or
  wherein $X^1$ and $X^5$=CH, $X^2$ and $X^4$=N, and $X^3$=C—R; where R may be selected from H and OMe; or
  wherein $X^1$ and $X^3$=N, and $X^2$, $X^4$ and $X^5$=CH;
or
Pyridines
  wherein $X^1$, $X^4$, and $X^5$=CH, $X^2$ may be selected from N and N=O, and $X^3$=C—R;
  where R may be selected from H and OMe; or
  wherein $X^1$=N, $X^2$, $X^4$ and $X^5$=CH, and $X^3$=C—R; where R may be selected from OMe and C≡CH;
or
Pyridazines
  wherein $X^1$ and $X^2$=N, $X^3$=C—R, and $X^4$ and $X^5$=CH; where R may be selected from H and OMe;
or
Pyrazine
  wherein $X^1$ and $X^4$=N, $X^2$ and $X^5$=CH, and $X^3$=C—R; where R may be selected from H and OMe;
or
Benzenes
  wherein $X^1$, $X^2$, $X^4$ and $X^5$=CH, $X^3$=C—R; where R may be selected from OMe, OEt, and C≡CH.

According to a second broad aspect of the present invention there is provided a method for reducing the nitrification rate in agricultural soils characterized by the steps of:

a) using at least one compound selected from the group consisting of:

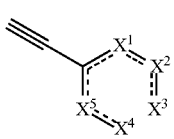

Formula 1 and
Pyrimidines
  wherein $X^1$ and $X^5$=N; $X^2$ and $X^4$=CH; and $X^3$=C—R; where R may be selected from H and OMe; or
  wherein $X^1$ and $X^5$=CH; $X^2$ and $X^4$=N; and $X^3$=C—R; where R may be selected from H and OMe; or
  wherein $X^1$ and $X^3$=N; and $X^2$, $X^4$ and $X^5$=CH;
or
Pyridines
  wherein $X^1$, $X^4$, and $X^5$=CH; $X^2$ may be selected from N and N=O; and $X^3$=C—R;
  where R may be selected from H and OMe; or
  wherein $X^1$=N; $X^2$, $X^4$ and $X^5$=CH; and $X^3$=C—R; where R may be selected from OMe and C≡CH;
or
Pyradazines
  wherein $X^1$ and $X^2$=N; $X^3$=C—R; and $X^4$ and $X^5$=CH; where R may be selected from H and OMe;
or
Pyrazines
  wherein $X^1$ and $X^4$=N; $X^2$ and $X^5$=CH; and $X^3$=C—R; where R may be selected from H and OMe;
or
Benzenes
  wherein $X^1$, $X^2$, $X^4$ and $X^5$=CH; $X^3$=C—R; where R may be selected from OMe, OEt, and C≡CH;
as a nitrification inhibitor, or for manufacture of a nitrification inhibitor, for directly or indirectly applying to the soil.

Preferably, indirect application to the soil involves the compound being applied to the soil via a carrier.

Preferably, the carrier may be water or effluent.

Preferably, the carrier may be a fertiliser granule.

Preferably, the fertiliser granule may be urea.

A method substantially as described above which can reduce nitrate leaching or nitrous oxide emissions.

A method substantially as described above which can also increase pasture or crop production.

A use, or method, substantially as described above wherein the compound is selected from the group consisting of:
2-Ethynyl 1,3 Diazine;
3-Ethynyl 1,5 Diazine;
4-Ethynylpyrimidine;
2-Ethynyl-5-methoxypyrimidine;
5-Ethynyl-2-methoxypyrimidine;
2-ethynyl-5-methoxypyridine;
5-ethynyl-2-methoxypyridine;
3-ethynylpyridine 1-oxide;
2,5-diethynylpyridine
3-Ethynylpyridazine;
3-Ethynyl-6-methoxypyridazine;
2-ethynylpyrazine;
2-Ethynyl-5-methoxypyrazine;
4-Ethynylanisole;
1-ethoxy-4-ethynylbenzene;
1,4-diethynylbenzene;
and has a dosage rate between substantially 1 kg/ha to 9 kg/ha.

A use, or method, wherein the compound has a dosage rate of substantially 2 kg/ha.

A use, or method, substantially as described above wherein the compound is selected from the group consisting of:
2-Ethynyl 1,3 Diazine;
3-Ethynyl 1,5 Diazine;
4-Ethynylpyrimidine;
2-Ethynyl-5-methoxypyrimidine;
5-Ethynyl-2-methoxypyrimidine;
2-ethynyl-5-methoxypyridine;
3-ethynylpyridine 1-oxide;
3-Ethynylpyridazine;

3-Ethynyl-6-methoxypyridazine;
2-Ethynyl-5-methoxypyrazine;
4-Ethynylanisole;
and has a dosage rate of substantially 1 kg/ha.

A use, or method, substantially as described above wherein the compound is selected from the group consisting of:
2-Ethynyl 1,3 Diazine;
3-Ethynyl 1,5 Diazine;
2-ethynyl-5-methoxypyridine;
3-ethynylpyridine 1-oxide;
3-Ethynylpyridazine;
and has a dosage rate of substantially 0.5 kg/ha.

According to a third broad aspect there is provided the use of a compound substantially as described above to treat a urine patch.

Preferably, the compound may be applied to the urine patch via an agricultural spray vehicle or autonomous robot.

Preferably, the agricultural spray vehicle or autonomous robot has apparatus thereon for detecting urine patches.

First Set of Aspects of the Invention: 2-Ethynyl 1,3 Diazine (Aka 2-Ethynylpyrimidine) (CAS 37972-24-0)

The present invention in one set of aspects relates to a new surprising use of a pyrimidine 2-Ethynyl 1,3 Diazine having a structure the same as, or substantially similar to, that indicated in the formula below:

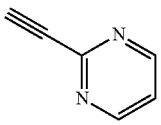

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the first aspect of the present invention there is provided the use of 2-Ethynyl 1,3 Diazine as a nitrification inhibitor.

Preferably, there is a use of 2 Ethynyl 1,3 Diazine substantially as described above wherein the effective application rate in kg/ha is significantly less than that of DCD.

According to a second part of the first aspect of the present invention there is provided the use of 2-Ethynyl 1,3 Diazine as an active ingredient in a nitrification inhibitor formulation.

According to a third part of the first aspect of the present invention there is provided the use of 2-Ethynyl 1,3 Diazine in the manufacture of a nitrification inhibitor.

According to a fourth part of the first aspect of the present invention there is provided the vending of 2-Ethynyl 1,3 Diazine, as a nitrification inhibitor, or for use in the manufacture of a nitrification inhibitor.

Preferably, the vending may be in a dosage quantity or multiple thereof.

According to a fifth part of the first aspect of the present invention there is provided the use of 2-Ethynyl 1,3 Diazine in the manufacture and/or vending of a soil treatment to effect nitrification inhibition and associated effects.

Preferably, a soil treatment to reduce nitrification and/or increase nitrogen use efficiency by plants.

According to a sixth part of the first aspect of the present invention there is provided the use substantially as described above wherein the nitrification inhibition reduces one or more of:
nitrous oxide emissions;
nitrate leaching; or
a combination thereof;
from soil.

According to a seventh part of the first aspect of the present invention there is provided the treatment of soil to effect nitrification inhibition and associated effects using 2-Ethynyl 1,3 Diazine.

According to an eighth part of the first aspect of the present invention there is provided the treatment of soil substantially as described above wherein 2-Ethynyl 1,3 Diazine is co-applied with urea granules or other nitrogen containing fertiliser granules.

According to a ninth part of the first aspect of the present invention there is provided the use of 2-Ethynyl 1,3 Diazine to coat urea fertiliser granules, or other nitrogen fertiliser granules.

According to a 10th part of the first aspect of the present invention there is provided a nitrogen fertiliser granule which is coated with 2-Ethynyl 1,3 Diazine.

Preferably, the nitrogen fertiliser granule may be urea (or other ammonium forms of nitrogen or a nitrogen fertiliser that releases ammonium in soil).

According to a $11^{th}$ part of the first aspect of the present invention there is provided the use of 2-Ethynyl 1,3 Diazine as an additive to nitrogen containing liquid fertilisers.

According to an $12^{th}$ part of the first aspect of the present invention there is provided the use of 2-Ethynyl 1,3 Diazine in a particulate and/or liquid form as a soil treatment.

According to a $13^{th}$ part of the first aspect of the present invention there is provided the manufacture and/or vending of 2-Ethynyl 1,3 Diazine to coat nitrogen fertilisers.

According to a $14^{th}$ part of the first aspect of the present invention there is provided the use of 2-Ethynyl 1,3 Diazine to increase nitrogen use efficiency in crop/pasture systems, or to increase nitrogen use efficiency of fertilisers.

According to a $15^{th}$ part of the first aspect of the present invention there is provided the use of 2-Ethynyl 1,3 Diazine to interrupt a soil microbial nitrification process.

According to an $16^{th}$ part of the first aspect of the present invention there is provided the use of 2-Ethynyl 1,3 Diazine to improve pasture/plant growth.

According to a $17^{th}$ part of the first aspect of the present invention there is provided the use of 2-Ethynyl 1,3 Diazine as a treatment for urine patch areas in a pasture.

According to a $18^{th}$ part of the first aspect of the present invention there is provided the use of co-application of 2-Ethynyl 1,3 Diazine and a source of nitrogen to crops or pasture.

According to a $19^{th}$ part of the first aspect of the present invention there is provided the vending of 2-Ethynyl 1,3 Diazine for a use substantially as described above in relation to the $6^{th}$, $7^{th}$ $9^{th}$, $11^{th}$, $12^{th}$, $14^{th}$, $15^{th}$, $16^{th}$, $17^{th}$, and $18^{th}$ parts of the first aspect of the present invention.

According to a $20^{th}$ part of the first aspect of the present invention there is provided a method of treating agricultural land or other land with nitrate leaching or nitrous oxide emission issues comprising the application of 2-Ethynyl 1,3 Diazine directly or indirectly thereto.

According to a 21$^{st}$ part of the first aspect of the present invention there is provided the co-application of 2-Ethynyl 1,3 Diazine with a nitrogen fertilizer to inhibit nitrification in soil.

According to a 22$^{nd}$ part of the first aspect of the present invention there is provided a method of treating animal urine patches by applying 2-Ethynyl 1,3 Diazine thereto either before, at the same time, or after, urine has been deposited.

According to a 23$^{rd}$ part of the first aspect of the present invention there is provided a method of treating soil by applying 2-Ethynyl 1,3 Diazine to areas of soil which will be, or have been, subjected to urea, fertiliser, effluent, or other nitrogen source.

According to a 24$^{th}$ part of the first aspect of the present invention there is provided the application of 2-Ethynyl 1,3 Diazine to soil, cropped land, or pasture.

According to a 25$^{th}$ part of the first aspect of the present invention there is provided the use of 2-Ethynyl 1,3 Diazine substantially as described above wherein the dosage rate is selected from 0.5 kg/ha to 9 kg/ha.

According to a 26$^{th}$ part of the first aspect of the present invention there is provided the use of 2-Ethynyl 1,3 Diazine substantially as described above wherein the dosage rate is 0.5 kg/ha.

According to a 27$^{th}$ part of the first aspect of the present invention there is provided the use of 2-Ethynyl 1,3 Diazine to retard corrosion of building stones or stone statues.

According to a 28$^{th}$ part of the first aspect of the present invention there is provided a method of treating agricultural land or urban land comprising the vending of 2-Ethynyl 1,3 Diazine in a manner selected from one or more of:
  dosage quantity;
  formulation type;
  co-delivery with a source of nitrogen; or
  a combination thereof,
which makes 2-Ethynyl 1,3 Diazine suitable for treating land to reduce the environmental impacts of: animal urine; nitrogen fertilisers; animal manures; or effluent.

More information on 2-Ethynyl 1,3 Diazine including chemical vendors can be found on the World-Wide Web at: sigmaaldrich.com/catalog/product/aldrich/802956.

Second Set of Aspects of the Invention: 3-Ethynyl 1,5 Diazine (Aka 5-Ethynylpyrimidine) (CAS 153286-94-3)

The present invention also in a second set of aspects relates to a new surprising use of a pyrimidine 3-Ethynyl 1,5 Diazine having a structure the same as, or substantially similar to, that indicated in the formula below:

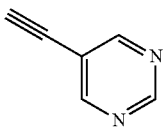

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the second aspect of the present invention there is provided the use of 3-Ethynyl 1,5 Diazine as a nitrification inhibitor.

Preferably, there is a use of 3-Ethynyl 1,5 Diazine substantially as described above wherein the effective application rate in kg/ha is significantly less than that of DCD.

According to a second part of the second aspect of the present invention there is provided the use of 3-Ethynyl 1,5 Diazine as an active ingredient in a nitrification inhibitor formulation.

According to a third part of the second aspect of the present invention there is provided the use of 3-Ethynyl 1,5 Diazine in the manufacture of a nitrification inhibitor.

According to a fourth part of the second aspect of the present invention there is provided the vending of 3-Ethynyl 1,5 Diazine, as a nitrification inhibitor, or for use in the manufacture of a nitrification inhibitor.

Preferably, the vending may be in a dosage quantity or multiple thereof.

According to a fifth part of the second aspect of the present invention there is provided the use of 3-Ethynyl 1,5 Diazine in the manufacture and/or vending of a soil treatment to effect nitrification inhibition and associated effects.

Preferably, a soil treatment to reduce nitrification and/or increase nitrogen use efficiency by plants.

According to a sixth part of the second aspect of the present invention there is provided the use substantially as described above wherein the nitrification inhibition reduces one or more of:
  nitrous oxide emissions;
  nitrate leaching; or
  a combination thereof;
from soil.

According to a seventh part of the second aspect of the present invention there is provided the treatment to effect nitrification and associated effects using 3-Ethynyl 1,5 Diazine.

According to an eighth part of the second aspect of the present invention there is provided the treatment of soil substantially as described above wherein 3-Ethynyl 1,5 Diazine is co-applied with urea granules or other nitrogen containing fertiliser granules.

According to a ninth part of the second aspect of the present invention there is provided the use of 3-Ethynyl 1,5 Diazine to coat urea fertiliser granules, or other nitrogen fertiliser granules.

According to a 10$^{th}$ part of the second aspect of the present invention there is provided a nitrogen fertiliser granule which is coated with 3-Ethynyl 1,5 Diazine.

Preferably, the nitrogen fertiliser granule may be urea (or other ammonium forms of nitrogen or a nitrogen fertiliser that releases ammonium in soil).

According to a 11$^{th}$ part of the second aspect of the present invention there is provided the use of 3-Ethynyl 1,5 Diazine as an additive to nitrogen containing liquid fertilisers.

According to an 12$^{th}$ part of the second aspect of the present invention there is provided the use of 3-Ethynyl 1,5 Diazine in a particulate and/or liquid form as a soil treatment.

According to a 13$^{th}$ part of the second aspect of the present invention there is provided the manufacture and/or vending of 3-Ethynyl 1,5 Diazine to coat nitrogen fertilisers.

According to a 14$^{th}$ part of the second aspect of the present invention there is provided the use of 3-Ethynyl 1,5 Diazine to increase nitrogen use efficiency in crop/pasture systems, or to increase nitrogen use efficiency of fertilisers.

According to a 15$^{th}$ part of the second aspect of the present invention there is provided the use of 3-Ethynyl 1,5 Diazine to interrupt a soil microbial nitrification process.

According to an 16th part of the second aspect of the present invention there is provided the use of 3-Ethynyl 1,5 Diazine to improve pasture/plant growth.

According to a 17th part of the second aspect of the present invention there is provided the use of 3-Ethynyl 1,5 Diazine as a treatment for urine patch areas in a pasture.

According to a 18th part of the second aspect of the present invention there is provided the use of co-application of 3-Ethynyl 1,5 Diazine and a source of nitrogen to crops or pasture.

According to a 19th part of the second aspect of the present invention there is provided the vending of 3-Ethynyl 1,5 Diazine for a use substantially as described above in relation to the 6th, 7th 9th, 11th, 12th, 14th, 15th, 16th, 17th, and 18th parts of the second aspect of the present invention.

According to a 20th part of the second aspect of the present invention there is provided a method of treating agricultural land or other land with nitrate leaching or nitrous oxide emission issues comprising the application of 3-Ethynyl 1,5 Diazine directly or indirectly thereto.

According to a 21st part of the second aspect of the present invention there is provided the co-application of 3-Ethynyl 1,5 Diazine with a nitrogen fertilizer to inhibit nitrification in soil.

According to a 22nd part of the second aspect of the present invention there is provided a method of treating animal urine patches by applying 3-Ethynyl 1,5 Diazine thereto either before, at the same time, or after, urine has been deposited.

According to a 23rd part of the second aspect of the present invention there is provided a method of treating soil by applying 3-Ethynyl 1,5 Diazine to areas of soil which will be, or have been, subjected to urea, fertiliser, effluent, or other nitrogen source.

According to a 24th part of the second aspect of the present invention there is provided the application of 3-Ethynyl 1,5 Diazine to soil, cropped land, or pasture.

According to a 25th part of the second aspect of the present invention there is provided the use of 3-Ethynyl 1,5 Diazine substantially as described above wherein the dosage rate is selected from 0.5 kg/ha to 9 kg/ha.

According to a 26th part of the second aspect of the present invention there is provided the use of 3-Ethynyl 1,5 Diazine substantially as described above wherein the dosage rate is 0.5 kg/ha.

According to a 27th part of the second aspect of the present invention there is provided the use of 3-Ethynyl 1,5 Diazine to retard corrosion of building stones or stone statues.

According to a 28th part of the second aspect of the present invention there is provided a method of treating agricultural land or urban land comprising the vending of 3-Ethynyl 1,5 Diazine in a manner selected from one or more of:
  dosage quantity;
  formulation type;
  co-delivery with a source of nitrogen; or
  a combination thereof,
which makes 3-Ethynyl 1,5 Diazine suitable for treating land to reduce the environmental impacts of: animal urine; nitrogen fertilisers; animal manures; or effluent.

More information on 3-Ethynyl 1,5 Diazine including chemical vendors can be found on the World-Wide-Web at: sigmaaldrich.com/catalog/product/aldrich/802980.

Third Set of Aspects of the Invention: 4-Ethynylpyrimidine (CAS 1196146-58-3)

The present invention also in a third set of aspects relates to a new surprising use of a 4-Ethynylpyrimidine having a structure the same as, or substantially similar to, that indicated in the formula below:

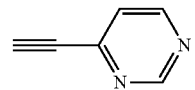

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the third aspect of the present invention there is provided the use of 4-Ethynylpyrimidine as a nitrification inhibitor.

Preferably, there is a use of 4-Ethynylpyrimidine substantially as described above wherein the effective application rate in kg/ha is significantly less than that of DCD.

According to a second part of the third aspect of the present invention there is provided the use of 4-Ethynylpyrimidine as an active ingredient in a nitrification inhibitor formulation.

According to a third part of the third aspect of the present invention there is provided the use of 4-Ethynylpyrimidine in the manufacture of a nitrification inhibitor.

According to a fourth part of the third aspect of the present invention there is provided the vending of 4-Ethynylpyrimidine, as a nitrification inhibitor, or for use in the manufacture of a nitrification inhibitor.

Preferably, the vending may be in a dosage quantity or multiple thereof.

According to a fifth part of the third aspect of the present invention there is provided the use of 4-Ethynylpyrimidine in the manufacture and/or vending of a soil treatment to effect nitrification inhibition and associated effects.

Preferably, a soil treatment to reduce nitrification and/or increase nitrogen use efficiency by plants.

According to a sixth part of the third aspect of the present invention there is provided the use substantially as described above wherein the nitrification inhibition reduces one or more of:
  nitrous oxide emissions;
  nitrate leaching; or
  a combination thereof;
from soil.

According to a seventh aspect of the present invention there is provided the treatment to effect nitrification and associated effects using 4-Ethynylpyrimidine.

According to an eighth part of the third aspect of the present invention there is provided the treatment of soil substantially as described above wherein 4-Ethynylpyrimidine is co-applied with urea granules or other nitrogen containing fertiliser granules.

According to a ninth part of the third aspect of the present invention there is provided the use of 4-Ethynylpyrimidine to coat urea fertiliser granules, or other nitrogen fertiliser granules.

According to a 10th part of the third aspect of the present invention there is provided a nitrogen fertiliser granule which is coated with 4-Ethynylpyrimidine.

Preferably, the nitrogen fertiliser granule may be urea (or other ammonium forms of nitrogen or a nitrogen fertiliser that releases ammonium in soil).

According to an 11th part of the third aspect of the present invention there is provided the use of 4-Ethynylpyrimidine as an additive to nitrogen containing liquid fertilisers.

According to a 12th part of the third aspect of the present invention there is provided the use of 4-Ethynylpyrimidine in a particulate and/or liquid form as a soil treatment.

According to a 13th part of the third aspect of the present invention there is provided the manufacture and/or vending of 4-Ethynylpyrimidine to coat nitrogen fertilisers.

According to a 14th part of the third aspect of the present invention there is provided the use of 4-Ethynylpyrimidine to increase nitrogen use efficiency in crop/pasture systems, or to increase nitrogen use efficiency of fertilisers.

According to a 15th part of the third aspect of the present invention there is provided the use of 4-Ethynylpyrimidine to interrupt a soil microbial nitrification process.

According to a 16th part of the third aspect of the present invention there is provided the use of 4-Ethynylpyrimidine to improve pasture/plant growth.

According to a 17th part of the third aspect of the present invention there is provided the use of 4-Ethynylpyrimidine as a treatment for urine patch areas in a pasture.

According to an 18th part of the third aspect of the present invention there is provided the use of co-application of 4-Ethynylpyrimidine and a source of nitrogen to crops or pasture.

According to a 19th part of the third aspect of the present invention there is provided the vending of 4-Ethynylpyrimidine for a use substantially as described above in relation to the 6th, 7th 9th, 11th, 12th, 14th, 15th, 16th, 17th, and 18th parts of the third aspect of the present invention.

According to a 20th part of the third aspect of the present invention there is provided a method of treating agricultural land or other land with nitrate leaching or nitrous oxide emission issues comprising the application of 4-Ethynylpyrimidine directly or indirectly thereto.

According to a 21st part of the third aspect of the present invention there is provided the co-application of 4-Ethynylpyrimidine with a nitrogen fertilizer to inhibit nitrification in soil.

According to a 22nd part of the third aspect of the present invention there is provided a method of treating animal urine patches by applying 4-Ethynylpyrimidine thereto either before, at the same time, or after, urine has been deposited.

According to a 23rd part of the third aspect of the present invention there is provided a method of treating soil by applying 4-Ethynylpyrimidine to areas of soil which will be, or have been, subjected to urea, fertiliser, effluent, or other nitrogen source.

According to a 24th part of the third aspect of the present invention there is provided the application of 4-Ethynylpyrimidine to soil, cropped land, or pasture.

According to a 25th part of the third aspect of the present invention there is provided the use of 4-Ethynylpyrimidine substantially as described above wherein the dosage rate is selected from 1 kg/ha to 9 kg/ha.

According to a 26th part of the third aspect of the present invention there is provided the use of 4-Ethynylpyrimidine substantially as described above wherein the dosage rate is 1 kg/ha.

According to a 27th part of the third aspect of the present invention there is provided a method of treating agricultural land or urban land comprising the vending of 4-Ethynylpyrimidine in a manner selected from one or more of:
dosage quantity;
formulation type;
co-delivery with a source of nitrogen; or
a combination thereof, which makes 4-Ethynylpyrimidine suitable for treating land to reduce the environmental impacts of: animal urine; nitrogen fertilisers; animal manures; or effluent.

More information on 4-Ethynylpyrimidine including chemical vendors can be found on the internet at: pubchem.ncbi.nlm.nih.gov/compound/4-Ethynylpyrimidine.

Fourth Set of Aspects of the Invention: 2-Ethynyl-5-Methoxypyrimidine (CAS 2400905-32-8)

The present invention also in a fourth set of aspects relates to a new surprising use of a 2-Ethynyl-5-methoxypyrimidine having a structure the same as, or substantially similar to, that indicated in the formula below:

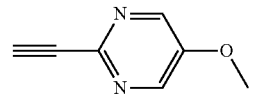

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the fourth aspect of the present invention there is provided the use of 2-Ethynyl-5-methoxypyrimidine as a nitrification inhibitor.

Preferably, there is a use of 2-Ethynyl-5-methoxypyrimidine substantially as described above wherein the effective application rate in kg/ha is significantly less than that of DCD.

According to a second part of the fourth aspect of the present invention there is provided the use of 2-Ethynyl-5-methoxypyrimidine as an active ingredient in a nitrification inhibitor formulation.

According to a third part of the fourth aspect of the present invention there is provided the use of 2-Ethynyl-5-methoxypyrimidine in the manufacture of a nitrification inhibitor.

According to a fourth part of the fourth aspect of the present invention there is provided the vending of 2-Ethynyl-5-methoxypyrimidine, as a nitrification inhibitor, or for use in the manufacture of a nitrification inhibitor.

Preferably, the vending may be in a dosage quantity or multiple thereof.

According to a fifth part of the fourth aspect of the present invention there is provided the use of 2-Ethynyl-5-methoxypyrimidine in the manufacture and/or vending of a soil treatment to effect nitrification inhibition and associated effects.

Preferably, a soil treatment to reduce nitrification and/or increase nitrogen use efficiency by plants.

According to a sixth part of the fourth aspect of the present invention there is provided the use of 2-Ethynyl-5- methoxypyrimidine substantially as described above wherein the nitrification inhibition reduces one or more of:
nitrous oxide emissions;
nitrate leaching; or a combination thereof;
from soil.

According to a seventh part of the fourth aspect of the present invention there is provided the treatment to effect nitrification and associated effects using 2-Ethynyl-5-methoxypyrimidine.

According to an eighth part of the fourth aspect of the present invention there is provided the treatment of soil substantially as described above wherein 2-Ethynyl-5-methoxy pyrimidine is co-applied with urea granules or other nitrogen containing fertiliser granules.

According to a ninth part of the fourth aspect of the present invention there is provided the use of 2-Ethynyl-5-methoxypyrimidine to coat urea fertiliser granules, or other nitrogen fertiliser granules.

According to a 10$^{th}$ part of the fourth aspect of the present invention there is provided a nitrogen fertiliser granule which is coated with 2-Ethynyl-5-methoxypyrimidine.

Preferably, the nitrogen fertiliser granule may be urea (or other ammonium forms of nitrogen or a nitrogen fertiliser that releases ammonium in soil).

According to an 11$^{th}$ part of the fourth aspect of the present invention there is provided the use of 2-Ethynyl-5-methoxypyrimidine as an additive to nitrogen containing liquid fertilisers.

According to a 12$^{th}$ part of the fourth aspect of the present invention there is provided the use of 2-Ethynyl-5-methoxypyrimidine in a particulate and/or liquid form as a soil treatment.

According to a 13$^{th}$ part of the fourth aspect of the present invention there is provided the manufacture and/or vending of 2-Ethynyl-5-methoxypyrimidine to coat nitrogen fertilisers.

According to a 14$^{th}$ part of the fourth aspect of the present invention there is provided the use of 2-Ethynyl-5-methoxypyrimidine to increase nitrogen use efficiency in crop/pasture systems, or to increase nitrogen use efficiency of fertilisers.

According to a 15$^{th}$ part of the fourth aspect of the present invention there is provided the use of 2-Ethynyl-5-methoxypyrimidine to interrupt a soil microbial nitrification process.

According to a 16$^{th}$ part of the fourth aspect of the present invention there is provided the use of 2-Ethynyl-5-methoxypyrimidine to improve pasture/plant growth.

According to a 17$^{th}$ part of the fourth aspect of the present invention there is provided the use of 2-Ethynyl-5-methoxypyrimidine as a treatment for urine patch areas in a pasture.

According to an 18$^{th}$ part of the fourth aspect of the present invention there is provided the use of co-application of 2-Ethynyl-5-methoxypyrimidine and a source of nitrogen to crops or pasture.

According to a 19$^{th}$ part of the fourth aspect of the present invention there is provided the vending of 2-Ethynyl-5-methoxypyrimidine for a use substantially as described above in relation to the 6$^{th}$, 7$^{th}$ 9$^{th}$, 11$^{th}$, 12$^{th}$,14$^{th}$, 15$^{th}$, 16$^{th}$, 17$^{th}$, and 18$^{th}$ parts of the fourth aspect of the present invention.

According to a 20$^{th}$ part of the fourth aspect of the present invention there is provided a method of treating agricultural land or other land with nitrate leaching or nitrous oxide emission issues comprising the application of 2-Ethynyl-5-methoxypyrimidine directly or indirectly thereto.

According to a 21$^{st}$ part of the fourth aspect of the present invention there is provided the co-application of 2-Ethynyl-5-methoxypyrimidine with a nitrogen fertilizer to inhibit nitrification in soil.

According to a 22$^{nd}$ part of the fourth aspect of the present invention there is provided a method of treating animal urine patches by applying 2-Ethynyl-5-methoxypyrimidine there to either before, at the same time, or after, urine has been deposited.

According to a 23$^{rd}$ part of the fourth aspect of the present invention there is provided a method of treating soil by applying 2-Ethynyl-5-methoxypyrimidine to areas of soil which will be, or have been, subjected to urea, fertiliser, effluent, or other nitrogen source.

According to a 24$^{th}$ part of the fourth aspect of the present invention there is provided the application of 2-Ethynyl-5-methoxypyrimidine to soil, cropped land, or pasture.

According to a 25$^{th}$ part of the fourth aspect of the present invention there is provided the use of 2-Ethynyl-5-methoxypyrimidine substantially as described above wherein the dosage rate is selected from 1 kg/ha to 9 kg/ha.

According to a 26$^{th}$ part of the fourth aspect of the present invention there is provided the use of 2-Ethynyl-5-methoxypyrimidine substantially as described above wherein the dosage rate is 1 kg/ha.

According to a 27$^{th}$ part of the fourth aspect of the present invention there is provided a method of treating agricultural land or urban land comprising the vending of 2-Ethynyl-5-methoxypyrimidine in a manner selected from one or more of:
dosage quantity;
formulation type;
co-delivery with a source of nitrogen; or
a combination thereof,
which makes 2-Ethynyl-5-methoxypyrimidine suitable for treating land to reduce the environmental impacts of: animal urine; nitrogen fertilisers; animal manures; or effluent.

More information on 2-Ethynyl-5-methoxypyrimidine including chemical vendors can be found on the internet at: chem-space.com/search/text/2-Ethynyl-5-methoxypyrimidine/0b84d50603c89ce6fdb0f732e78b0105.

Fifth Set of Aspects of the Invention: 5-Ethynyl-2-Methoxypyrimidine (CAS 1059705-07-5)

The present invention also in a fifth set of aspects relates to a new surprising use of a 5-Ethynyl-2-methoxypyrimidine having a structure the same as, or substantially similar to, that indicated in the formula below:

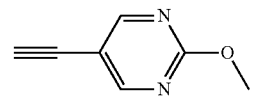

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the fifth aspect of the present invention there is provided the use of 5-Ethynyl-2-methoxypyrimidine as a nitrification inhibitor.

Preferably, there is a use of 5-Ethynyl-2-methoxypyrimidine substantially as described above wherein the effective application rate in kg/ha is significantly less than that of DCD.

According to a second part of the fifth aspect second aspect of the present invention there is provided the use of 5-Ethynyl-2-methoxypyrimidine as an active ingredient in a nitrification inhibitor formulation.

According to a third part of the fifth aspect of the present invention there is provided the use of 5-Ethynyl-2-methoxypyrimidine in the manufacture of a nitrification inhibitor.

According to a fourth part of the fifth aspect of the present invention there is provided the vending of 5-Ethynyl-2-methoxypyrimidine, as a nitrification inhibitor, or for use in the manufacture of a nitrification inhibitor.

Preferably, the vending may be in a dosage quantity or multiple thereof.

According to a fifth part of the fifth aspect of the present invention there is provided the use of 5-Ethynyl-2-methoxypyrimidine in the manufacture and/or vending of a soil treatment to effect nitrification inhibition and associated effects.

Preferably, a soil treatment to reduce nitrification and/or increase nitrogen use efficiency by plants.

According to a sixth part of the fifth aspect of the present invention there is provided the use of 5-Ethynyl-2-methoxypyrimidine substantially as described above wherein the nitrification inhibition reduces one or more of:
  nitrous oxide emissions;
  nitrate leaching; or
  a combination thereof;
from soil.

According to a seventh part of the fifth aspect of the present invention there is provided the treatment to effect nitrification and associated effects using 5-Ethynyl-2-methoxypyrimidine.

According to an eighth part of the fifth aspect of the present invention there is provided the treatment of soil substantially as described above wherein 5-Ethynyl-2-methoxypyrimidine is co-applied with urea granules or other nitrogen containing fertiliser granules.

According to a ninth part of the fifth aspect of the present invention there is provided the use of 5-Ethynyl-2-methoxypyrimidine to coat urea fertiliser granules, or other nitrogen fertiliser granules.

According to a $10^{th}$ part of the fifth aspect of the present invention there is provided a nitrogen fertiliser granule which is coated with 5-Ethynyl-2-methoxypyrimidine.

Preferably, the nitrogen fertiliser granule may be urea (or other ammonium forms of nitrogen or a nitrogen fertiliser that releases ammonium in soil).

According to an $11^{th}$ part of the fifth aspect of the present invention there is provided the use of 5-Ethynyl-2-methoxypyrimidine as an additive to nitrogen containing liquid fertilisers.

According to a $12^{th}$ part of the fifth aspect of the present invention there is provided the use of 5-Ethynyl-2-methoxypyrimidine in a particulate and/or liquid form as a soil treatment.

According to a $13^{th}$ part of the fifth aspect of the present invention there is provided the manufacture and/or vending of 5-Ethynyl-2-methoxypyrimidine to coat nitrogen fertilisers.

According to a $14^{th}$ part of the fifth aspect of the present invention there is provided the use of 5-Ethynyl-2-methoxypyrimidine to increase nitrogen use efficiency in crop/pasture systems, or to increase nitrogen use efficiency of fertilisers.

According to a $15^{th}$ part of the fifth aspect of the present invention there is provided the use of 5-Ethynyl-2-methoxypyrimidine to interrupt a soil microbial nitrification process.

According to a $16^{th}$ part of the fifth aspect of the present invention there is provided the use of 5-Ethynyl-2-methoxypyrimidine to improve pasture/plant growth.

According to a $17^{th}$ part of the fifth aspect of the present invention there is provided the use of 5-Ethynyl-2-methoxypyrimidine as a treatment for urine patch areas in a pasture.

According to an $18^{th}$ part of the fifth aspect of the present invention there is provided the use of co-application of 5-Ethynyl-2-methoxypyrimidine and a source of nitrogen to crops or pasture.

According to a $19^{th}$ part of the fifth aspect of the present invention there is provided the vending of 5-Ethynyl-2-methoxypyrimidine for a use substantially as described above in relation to the $6^{th}$, $7^{th}$ $9^{th}$, $11^{th}$, $12^{th}$,$14^{th}$, $15^{th}$, $16^{th}$, $17^{th}$, and $18^{th}$ parts of the fifth aspect of the present invention.

According to a $20^{th}$ part of the fifth aspect of the present invention there is provided a method of treating agricultural land or other land with nitrate leaching or nitrous oxide emission issues comprising the application of 5-Ethynyl-2-methoxypyrimidine directly or indirectly thereto.

According to a $21^{th}$ part of the fifth aspect of the present invention there is provided the co-application of 5-Ethynyl-2-methoxypyrimidine with a nitrogen fertilizer to inhibit nitrification in soil.

According to a $22^{nd}$ part of the fifth aspect of the present invention there is provided a method of treating animal urine patches by applying 5-Ethynyl-2-methoxypyrimidine there to either before, at the same time, or after, urine has been deposited.

According to a $23^{rd}$ part of the fifth aspect of the present invention there is provided a method of treating soil by applying 5-Ethynyl-2-methoxypyrimidine to areas of soil which will be, or have been, subjected to urea, fertiliser, effluent, or other nitrogen source.

According to a $24^{th}$ part of the fifth aspect of the present invention there is provided the application of 5-Ethynyl-2-methoxypyrimidine to soil, cropped land, or pasture.

According to a $25^{th}$ part of the fifth aspect of the present invention there is provided the use of 5-Ethynyl-2-methoxypyrimidine substantially as described above wherein the dosage rate is selected from 1 kg/ha to 9 kg/ha.

According to a $26^{th}$ part of the fifth aspect of the present invention there is provided the use of 5-Ethynyl-2-methoxypyrimidine substantially as described above wherein the dosage rate is 1 kg/ha.

According to a $27^{th}$ part of the fifth aspect of the present invention there is provided a method of treating agricultural land or urban land comprising the vending of 5-Ethynyl-2-methoxypyrimidine in a manner selected from one or more of:
  dosage quantity;
  formulation type;
  co-delivery with a source of nitrogen; or
  a combination thereof,
which makes 5-Ethynyl-2-methoxypyrimidine suitable for treating land to reduce the environmental impacts of: animal urine; nitrogen fertilisers; animal manures; or effluent.

More information on 5-Ethynyl-2-methoxypyrimidine including chemical vendors can be found on the World-Wide Web at: achemblock.com/5-ethynyl-2-methoxypyrimidine.html.

Sixth Set of Aspects of the Invention: 2-Ethynyl-5-Methoxypyridine (CAS 1196155-18-6)

The present invention also in a sixth set of aspects relates to a new surprising use of a 2-ethynyl-5-methoxypyridine having a structure the same as, or substantially similar to, that indicated in the formula below:

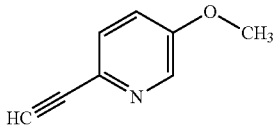

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the sixth aspect of the present invention there is provided the use of 2-ethynyl-5-methoxypyridine as a nitrification inhibitor.

Preferably, there is a use of 2-ethynyl-5-methoxypyridine substantially as described above wherein the effective application rate in kg/ha is significantly less than that of DCD.

According to a second part of the sixth aspect of the present invention there is provided the use of 2-ethynyl-5-methoxypyridine as an active ingredient in a nitrification inhibitor formulation.

According to a third part of the sixth aspect of the present invention there is provided the use of 2-ethynyl-5-methoxypyridine in the manufacture of a nitrification inhibitor.

According to a fourth part of the sixth aspect of the present invention there is provided the vending of 2-ethynyl-5-methoxypyridine, as a nitrification inhibitor, or for use in the manufacture of a nitrification inhibitor.

Preferably, the vending may be in a dosage quantity or multiple thereof.

According to a fifth part of the sixth aspect of the present invention there is provided the use of 2-ethynyl-5-methoxypyridine in the manufacture and/or vending of a soil treatment to effect nitrification inhibition and associated effects.

Preferably, a soil treatment to reduce nitrification and/or increase nitrogen use efficiency by plants.

According to a sixth part of the sixth aspect of the present invention there is provided the use substantially as described above wherein the nitrification inhibition reduces one or more of:
nitrous oxide emissions;
nitrate leaching; or
a combination thereof;
from soil.

According to a seventh part of the sixth aspect of the present invention there is provided a treatment to effect nitrification and associated effects using 2-ethynyl-5-methoxypyridine.

According to an eighth part of the sixth aspect of the present invention there is provided the treatment of soil substantially as described above wherein 2-ethynyl-5-methoxypyridine is co-applied with urea granules or other nitrogen containing fertiliser granules.

According to a ninth part of the sixth aspect of the present invention there is provided the use of 2-ethynyl-5-methoxypyridine to coat urea fertiliser granules, or other nitrogen fertiliser granules.

According to a $10^{th}$ part of the sixth aspect of the present invention there is provided a nitrogen fertiliser granule which is coated with 2-ethynyl-5-methoxypyridine.

Preferably, the nitrogen fertiliser granule may be urea (or other ammonium forms of nitrogen or a nitrogen fertiliser that releases ammonium in soil).

According to an $11^{th}$ part of the sixth aspect of the present invention there is provided the use of 2-ethynyl-5-methoxypyridine as an additive to nitrogen containing liquid fertilisers.

According to a $12^{th}$ part of the sixth aspect of the present invention there is provided the use of 2-ethynyl-5-methoxypyridine in a particulate and/or liquid form as a soil treatment.

According to a $13^{th}$ part of the sixth aspect of the present invention there is provided the manufacture and/or vending of 2-ethynyl-5-methoxypyridine to coat nitrogen fertilisers.

According to a $14^{th}$ part of the sixth aspect of the present invention there is provided the use of 2-ethynyl-5-methoxypyridine to increase nitrogen use efficiency in crop/pasture systems, or to increase nitrogen use efficiency of fertilisers.

According to a $15^{th}$ part of the sixth aspect of the present invention there is provided the use of 2-ethynyl-5-methoxypyridine to interrupt a soil microbial nitrification process.

According to a $16^{th}$ part of the sixth aspect of the present invention there is provided the use of 2-ethynyl-5-methoxypyridine to improve pasture/plant growth.

According to a $17^{th}$ part of the sixth aspect of the present invention there is provided the use of 2-ethynyl-5-methoxypyridine as a treatment for urine patch areas in a pasture.

According to an $18^{th}$ part of the sixth aspect of the present invention there is provided the use of co-application of 2-ethynyl-5-methoxypyridine and a source of nitrogen to crops or pasture.

According to a $19^{th}$ part of the sixth aspect of the present invention there is provided the vending of 2-ethynyl-5-methoxypyridine for a use substantially as described above in relation to the $6^{th}$, $7^{th}$ $9^{th}$, $11^{th}$, $12^{th}$, $14^{th}$, $15^{th}$, $16^{th}$, $17^{th}$, and $18^{th}$ parts of the sixth aspect of the present invention.

According to a $20^{th}$ part of the sixth aspect of the present invention there is provided a method of treating agricultural land or other land with nitrate leaching or nitrous oxide emission issues comprising the application of 2-ethynyl-5-methoxypyridine directly or indirectly thereto.

According to a $21^{st}$ part of the sixth aspect of the present invention there is provided the co-application of 2-ethynyl-5-methoxypyridine with a nitrogen fertilizer to inhibit nitrification in soil.

According to a $22^{nd}$ part of the sixth aspect of the present invention there is provided a method of treating animal urine patches by applying 2-ethynyl-5-methoxypyridine thereto either before, at the same time, or after, urine has been deposited.

According to a $23^{rd}$ part of the sixth aspect of the present invention there is provided a method of treating soil by applying 2-ethynyl-5-methoxypyridine to areas of soil which will be, or have been, subjected to urea, fertiliser, effluent, or other nitrogen source.

According to a 24th aspect of the sixth aspect of the present invention there is provided the application of 2-ethynyl-5-methoxypyridine to soil, cropped land, or pasture.

According to a 25th part of the sixth aspect of the present invention there is provided the use of 2-ethynyl-5-methoxypyridine substantially as described above wherein the dosage rate is selected from 0.5 kg/ha to 9 kg/ha.

According to a 26th part of the sixth aspect of the present invention there is provided the use of 2-ethynyl-5-methoxypyridine substantially as described above wherein the dosage rate is 0.5 kg/ha.

According to a 27th part of the sixth aspect of the present invention there is provided a method of treating agricultural land or urban land comprising the vending of 2-ethynyl-5-methoxypyridine in a manner selected from one or more of:
  dosage quantity;
  formulation type;
  co-delivery with a source of nitrogen; or
  a combination thereof,
which makes 2-ethynyl-5-methoxypyridine suitable for treating land to reduce the environmental impacts of: animal urine; nitrogen fertilisers; animal manures; or effluent.

More information on 2-ethynyl-5-methoxypyridine including chemical vendors can be found on the World-Wide-Web at: sigmaaldrich.com/catalog/product/aldrich/cds023940.

Seventh Set of Aspects of the Invention: 5-Ethynyl-2-Methoxypyridine (CAS 663955-59-7)

The present invention also in a seventh set of aspects relates to a new surprising use of a 5-ethynyl-2-methoxypyridine having a structure the same as, or substantially similar to, that indicated in the formula below:

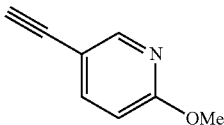

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the seventh aspect of the present invention there is provided the use of 5-ethynyl-2-methoxypyridine as a nitrification inhibitor.

Preferably, there is a use of 5-ethynyl-2-methoxypyridine substantially as described above wherein the effective application rate in kg/ha is significantly less than that of DCD.

According to a second part of the seventh aspect of the present invention there is provided the use of 5-ethynyl-2-methoxypyridine as an active ingredient in a nitrification inhibitor formulation.

According to a third part of the seventh aspect of the present invention there is provided the use of 5-ethynyl-2-methoxypyridine in the manufacture of a nitrification inhibitor.

According to a fourth part of the seventh aspect of the present invention there is provided the vending of 5-ethynyl-2-methoxypyridine, as a nitrification inhibitor, or for use in the manufacture of a nitrification inhibitor.

Preferably, the vending may be in a dosage quantity or multiple thereof.

According to a fifth part of the seventh aspect of the present invention there is provided the use of 5-ethynyl-2-methoxypyridine in the manufacture and/or vending of a soil treatment to effect nitrification inhibition and associated effects.

Preferably, a soil treatment to reduce nitrification and/or increase nitrogen use efficiency by plants.

According to a sixth part of the seventh aspect of the present invention there is provided the use substantially as described above wherein the nitrification inhibition reduces one or more of:
  nitrous oxide emissions;
  nitrate leaching; or
  a combination thereof;
from soil.

According to a seventh part of the seventh aspect of the present invention there is provided a treatment to effect nitrification and associated effects using 5-ethynyl-2-methoxypyridine.

According to an eighth part of the seventh aspect of the present invention there is provided the treatment of soil substantially as described above wherein 5-ethynyl-2-methoxypyridine is co-applied with urea granules or other nitrogen containing fertiliser granules.

According to a ninth part of the seventh aspect of the present invention there is provided the use of 5-ethynyl-2-methoxypyridine to coat urea fertiliser granules, or other nitrogen fertiliser granules.

According to a 10th part of the seventh aspect of the present invention there is provided a nitrogen fertiliser granule which is coated with 5-ethynyl-2-methoxypyridine.

Preferably, the nitrogen fertiliser granule may be urea (or other ammonium forms of nitrogen or a nitrogen fertiliser that releases ammonium in soil).

According to an 11th part of the seventh aspect of the present invention there is provided the use of 5-ethynyl-2-methoxypyridine as an additive to nitrogen containing liquid fertilisers.

According to a 12th part of the seventh aspect of the present invention there is provided the use of 5-ethynyl-2-methoxypyridine in a particulate and/or liquid form as a soil treatment.

According to a 13th part of the seventh aspect of the present invention there is provided the manufacture and/or vending of 5-ethynyl-2-methoxypyridine to coat nitrogen fertilisers.

According to a 14th part of the seventh aspect of the present invention there is provided the use of 5-ethynyl-2-methoxypyridine to increase nitrogen use efficiency in crop/pasture systems, or to increase nitrogen use efficiency of fertilisers.

According to a 15th part of the seventh aspect of the present invention there is provided the use of 5-ethynyl-2-methoxypyridine to interrupt a soil microbial nitrification process.

According to a 16th part of the seventh aspect of the present invention there is provided the use of 5-ethynyl-2-methoxypyridine to improve pasture/plant growth.

According to a 17th part of the seventh aspect of the present invention there is provided the use of 5-ethynyl-2-methoxypyridine as a treatment for urine patch areas in a pasture.

According to an 18th part of the seventh aspect of the present invention there is provided the use of co-application of 5-ethynyl-2-methoxypyridine and a source of nitrogen to crops or pasture.

According to a 19th part of the seventh aspect of the present invention there is provided the vending of 5-ethynyl-2-methoxypyridine for a use substantially as described above in relation to the 6th, 7th 9th, 11th, 12th, 14th, 15th, 16th, 17th, and 18th parts of the seventh aspect of the present invention.

According to a 20th part of the seventh aspect of the present invention there is provided a method of treating agricultural land or other land with nitrate leaching or nitrous oxide emission issues comprising the application of 5-ethynyl-2-methoxypyridine directly or indirectly thereto.

According to a 21st part of the seventh aspect of the present invention there is provided the co-application 5-ethynyl-2-methoxypyridine with a nitrogen fertilizer to inhibit nitrification in soil.

According to a 22nd part of the seventh aspect of the present invention there is provided a method of treating animal urine patches by applying 2-ethynyl-5-methoxypyridine thereto either before, at the same time, or after, urine has been deposited.

According to a 23rd part of the seventh aspect of the present invention there is provided a method of treating soil by applying 5-ethynyl-2-methoxypyridine to areas of soil which will be, or have been, subjected to urea, fertiliser, effluent, or other nitrogen source.

According to a 24th part of the seventh aspect of the present invention there is provided the application of 5-ethynyl-2-methoxypyridine to soil, cropped land, or pasture.

According to a 25th part of the seventh aspect of the present invention there is provided the use of 5-ethynyl-2-methoxypyridine substantially as described above wherein the dosage rate is selected from 2 kg/ha to 9 kg/ha.

According to a 26th part of the seventh aspect of the present invention there is provided the use of 5-ethynyl-2-methoxypyridine substantially as described above wherein the dosage rate is 2 kg/ha.

According to a 27th part of the seventh aspect of the present invention there is provided a method of treating agricultural land or urban land comprising the vending of 5-ethynyl-2-methoxypyridine in a manner selected from one or more of:

dosage quantity;

formulation type;

co-delivery with a source of nitrogen; or a combination thereof, which makes 5-ethynyl-2-methoxypyridine suitable for treating land to reduce the environmental impacts of: animal urine; nitrogen fertilisers; animal manures; or effluent.

More information on 5-ethynyl-2-methoxypyridine including chemical vendors can be found on the World-Wide-Web at: sigmaaldrich.com/catalog/product/aldrich/rni00198.

NIC 142

8th Set of Aspects of the Invention: 3-Ethynylpyridine 1-Oxide (CAS 49836-11-5)

The present invention also in an 8th set of aspects relates to a new surprising use of a 3-ethynylpyridine 1-oxide having a structure the same as, or substantially similar to, that indicated in the formula below:

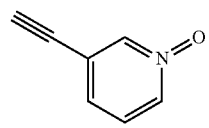

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

Aspects of the Invention

According to a first part of the 8th aspect of the present invention there is provided the use of 3-ethynylpyridine 1-oxide as a nitrification inhibitor.

Preferably, there is a use of 3-ethynylpyridine 1-oxide substantially as described above wherein the effective application rate in kg/ha is significantly less than that of DCD.

According to a second part of the 8th aspect of the present invention there is provided the use of 3-ethynylpyridine 1-oxide as an active ingredient in a nitrification inhibitor formulation.

According to a third part of the 8th aspect of the present invention there is provided the use of 3-ethynylpyridine 1-oxide in the manufacture of a nitrification inhibitor.

According to a fourth part of the 8th aspect of the present invention there is provided the vending of 3-ethynylpyridine 1-oxide, as a nitrification inhibitor, or for use in the manufacture of a nitrification inhibitor.

Preferably, the vending may be in a dosage quantity or multiple thereof.

According to a fifth part of the 8th aspect of the present invention there is provided the use of 3-ethynylpyridine 1-oxide in the manufacture and/or vending of a soil treatment to effect nitrification inhibition and associated effects.

Preferably, a soil treatment to reduce nitrification and/or increase nitrogen use efficiency by plants.

According to a sixth part of the 8th aspect of the present invention there is provided the use substantially as described above wherein the nitrification inhibition reduces one or more of:

nitrous oxide emissions;

nitrate leaching; or a combination thereof;

from soil.

According to a seventh part of the 8th aspect of the present invention there is provided the treatment to effect nitrification and associated effects using 3-ethynylpyridine 1-oxide.

According to an eighth part of the 8th aspect of the present invention there is provided the treatment of soil substantially as described above wherein 3-ethynylpyridine 1-oxide is co-applied with urea granules or other nitrogen containing fertiliser granules.

According to a ninth part of the 8th aspect of the present invention there is provided the use of 3-ethynylpyridine 1-oxide to coat urea fertiliser granules, or other nitrogen fertiliser granules.

According to a 10th part of the 8th aspect of the present invention there is provided a nitrogen fertiliser granule which is coated with 3-ethynylpyridine 1-oxide.

Preferably, the nitrogen fertiliser granule may be urea (or other ammonium forms of nitrogen or a nitrogen fertiliser that releases ammonium in soil).

According to an 11th part of the 8th aspect of the present invention there is provided the use of 3-ethynylpyridine 1-oxide as an additive to nitrogen containing liquid fertilisers.

According to a 12th part of the 8th aspect of the present invention there is provided the use of 3-ethynylpyridine 1-oxide in a particulate and/or liquid form as a soil treatment.

According to a 13th part of the 8th aspect of the present invention there is provided the manufacture and/or vending of 3-ethynylpyridine 1-oxide to coat nitrogen fertilisers.

According to a 14th part of the 8th aspect of the present invention there is provided the use of 3-ethynylpyridine 1-oxide to increase nitrogen use efficiency in crop/pasture systems, or to increase nitrogen use efficiency of fertilisers.

According to a 15th part of the 8th aspect of the present invention there is provided the use of 3-ethynylpyridine 1-oxide to interrupt a soil microbial nitrification process.

According to a 16th part of the 8th aspect of the present invention there is provided the use of 3-ethynylpyridine 1-oxide to improve pasture/plant growth.

According to a 17th part of the 8th aspect of the present invention there is provided the use of 3-ethynylpyridine 1-oxide as a treatment for urine patch areas in a pasture.

According to an 18th part of the 8th aspect of the present invention there is provided the use of co-application of 3-ethynylpyridine 1-oxide and a source of nitrogen to crops or pasture.

According to a 19th part of the 8th aspect of the present invention there is provided the vending of 3-ethynylpyridine 1-oxide for a use substantially as described above in relation to the 6th, 7th 9th, 11th, 12th,14[th], 15th, 16th, 17th, and 18th parts of the 8th aspect of the present invention.

According to a 20th part of the 8th aspect of the present invention there is provided a method of treating agricultural land or other land with nitrate leaching or nitrous oxide emission issues comprising the application of 3-ethynylpyridine 1-oxide directly or indirectly thereto.

According to a 21st part of the 8th aspect of the present invention there is provided the co-application of 3-ethynylpyridine 1-oxide with a nitrogen fertilizer to inhibit nitrification in soil.

According to a 22nd part of the 8th aspect of the present invention there is provided a method of treating animal urine patches by applying 3-ethynylpyridine 1-oxide thereto either before, at the same time, or after, urine has been deposited.

According to a 23rd part of the 8th aspect of the present invention there is provided a method of treating soil by applying 3-ethynylpyridine 1-oxide to areas of soil which will be, or have been, subjected to urea, fertiliser, effluent, or other nitrogen source.

According to a 24th part of the 8th aspect of the present invention there is provided the application of 3-ethynylpyridine 1-oxide to soil, cropped land, or pasture.

According to a 25th part of the 8th aspect of the present invention there is provided the use of 3-ethynylpyridine 1-oxide substantially as described above wherein the dosage rate is selected from 0.5 kg/ha to 9 kg/ha.

According to a 26th part of the 8th aspect of the present invention there is provided the use of 3-ethynylpyridine 1-oxide substantially as described above wherein the dosage rate is 0.5 kg/ha.

According to a 27th part of the 8th aspect of the present invention there is provided a method of treating agricultural land or urban land comprising the vending of 3-ethynylpyridine 1-oxide in a manner selected from one or more of:
    dosage quantity;
    formulation type;
    co-delivery with a source of nitrogen; or
    a combination thereof,
which makes 3-ethynylpyridine 1-oxide suitable for treating land to reduce the environmental impacts of: animal urine; nitrogen fertilisers; animal manures; or effluent.

More information on 3-ethynylpyridine 1-oxide including chemical vendors can be found on the internet at: pubchem.ncbi.nlm.nih.gov/compound/3-Ethynyl-pyridine-1-oxide.

9th Set of Aspects of the Invention: 2,5-Diethynylpyridine (CAS 137000-75-0)

The present invention also in a 9th set of aspects relates to a new surprising use of a 2,5-diethynylpyridine having a structure the same as, or substantially similar to, that indicated in the formula below:

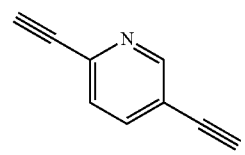

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the 9th aspect of the present invention there is provided the use of 2,5-diethynylpyridine as a nitrification inhibitor.

Preferably, there is a use of 2,5-diethynylpyridine substantially as described above wherein the effective application rate in kg/ha is significantly less than that of DCD.

According to a second part of the 9th aspect of the present invention there is provided the use of 2,5-diethynylpyridine as an active ingredient in a nitrification inhibitor formulation.

According to a third part of the 9th aspect of the present invention there is provided the use of 2,5-diethynylpyridine in the manufacture of a nitrification inhibitor.

According to a fourth part of the 9th aspect of the present invention there is provided the vending of 2,5-diethynylpyridine, as a nitrification inhibitor, or for use in the manufacture of a nitrification inhibitor.

Preferably, the vending may be in a dosage quantity or multiple thereof.

According to a fifth part of the 9th aspect of the present invention there is provided the use of 2,5-diethynylpyridine in the manufacture and/or vending of a soil treatment to effect nitrification inhibition and associated effects.

Preferably, a soil treatment to reduce nitrification and/or increase nitrogen use efficiency by plants.

According to a sixth part of the 9th aspect of the present invention there is provided the use substantially as described above wherein the nitrification inhibition reduces one or more of:

nitrous oxide emissions;
nitrate leaching; or
a combination thereof;
from soil.

According to a seventh part of the 9th aspect of the present invention there is provided a treatment to effect nitrification and associated effects using 2,5-diethynylpyridine.

According to an eighth part of the 9th aspect of the present invention there is provided the treatment of soil substantially as described above wherein 2,5-diethynylpyridine is co-applied with urea granules or other nitrogen containing fertiliser granules.

According to a ninth part of the 9th aspect of the present invention there is provided the use of 2,5-diethynylpyridine to coat urea fertiliser granules, or other nitrogen fertiliser granules.

According to a 10th part of the 9th aspect of the present invention there is provided a nitrogen fertiliser granule which is coated with 2,5-diethynylpyridine.

Preferably, the nitrogen fertiliser granule may be urea (or other ammonium forms of nitrogen or a nitrogen fertiliser that releases ammonium in soil).

According to an 11th part of the 9th aspect of the present invention there is provided the use of 2,5-diethynylpyridine as an additive to nitrogen containing liquid fertilisers.

According to a 12th part of the 9th aspect of the present invention there is provided the use of 2,5-diethynylpyridine in a particulate and/or liquid form as a soil treatment.

According to a 13th part of the 9th aspect of the present invention there is provided the manufacture and/or vending of 2,5-diethynylpyridine to coat nitrogen fertilisers.

According to a 14th part of the 9th aspect of the present invention there is provided the use of 2,5-diethynylpyridine to increase nitrogen use efficiency in crop/pasture systems, or to increase nitrogen use efficiency of fertilisers.

According to a 15th part of the 9th aspect of the present invention there is provided the use of 2,5-diethynylpyridine to interrupt a soil microbial nitrification process.

According to a 16th part of the 9th aspect of the present invention there is provided the use of 2,5-diethynylpyridine to improve pasture/plant growth.

According to a 17th part of the 9th aspect of the present invention there is provided the use of 2,5-diethynylpyridine as a treatment for urine patch areas in a pasture.

According to an 18th part of the 9th aspect of the present invention there is provided the use of co-application of 2,5-diethynylpyridine and a source of nitrogen to crops or pasture.

According to a 19th part of the 9th aspect of the present invention there is provided the vending of 2,5-diethynylpyridine for a use substantially as described above in relation to the 6th, 7th 9th, 11th, 12th, 14th, 15th, 16th, 17th, and 18th parts of the 9th aspect of the present invention.

According to a 20th part of the 9th aspect of the present invention there is provided a method of treating agricultural land or other land with nitrate leaching or nitrous oxide emission issues comprising the application of 2,5-diethynylpyridine directly or indirectly thereto.

According to a 21st part of the 9th aspect of the present invention there is provided the co-application 2,5-diethynylpyridine with a nitrogen fertilizer to inhibit nitrification in soil.

According to a 22nd part of the 9th aspect of the present invention there is provided a method of treating animal urine patches by applying 2,5-diethynylpyridine thereto either before, at the same time, or after, urine has been deposited.

According to a 23rd part of the 9th aspect of the present invention there is provided a method of treating soil by applying 2,5-diethynylpyridine to areas of soil which will be, or have been, subjected to urea, fertiliser, effluent, or other nitrogen source.

According to a 24th part of the 9th aspect of the present invention there is provided the application of 2,5-diethynylpyridine to soil, cropped land, or pasture.

According to a 25th part of the 9th aspect of the present invention there is provided the use of 2,5-diethynylpyridine substantially as described above wherein the dosage rate is selected from 2 kg/ha to 9 kg/ha.

According to a 26th part of the 9th aspect of the present invention there is provided the use of 2,5-diethynylpyridine substantially as described above wherein the dosage rate is 2 kg/ha.

According to a 27th part of the 9th aspect of the present invention there is provided a method of treating agricultural land or urban land comprising the vending of 2,5-diethynylpyridine in a manner selected from one or more of:
dosage quantity;
formulation type;
co-delivery with a source of nitrogen; or
a combination thereof,
which makes 2,5-diethynylpyridine suitable for treating land to reduce the environmental impacts of: animal urine; nitrogen fertilisers; animal manures; or effluent.

More information on 2,5-diethynylpyridine including chemical vendors can be found on the World-Wide-Web at: chemspider.com/Chemical-Structure.23500007.html.

10th Set of Aspects of the Invention: 3-Ethynylpyridazine (CAS 1017793-08-6)

The present invention also in an 11th set of aspects relates to a new surprising use of a 3-Ethynylpyridazine having a structure the same as, or substantially similar to, that indicated in the formula below:

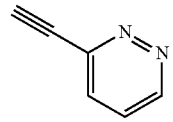

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

Aspects of the Invention

According to a first part of the 10th aspect of the present invention there is provided the use of 3-Ethynylpyridazine as a nitrification inhibitor.

Preferably, there is a use of 3-Ethynylpyridazine substantially as described above wherein the effective application rate in kg/ha is significantly less than that of DCD.

According to a second part of the 10th aspect of the present invention there is provided the use of 3-Ethynylpyridazine as an active ingredient in a nitrification inhibitor formulation.

According to a third part of the 10th aspect of the present invention there is provided the use of 3-Ethynylpyridazine in the manufacture of a nitrification inhibitor.

According to a fourth part of the 10th aspect of the present invention there is provided the vending of 3-Ethynylpyridazine, as a nitrification inhibitor, or for use in the manufacture of a nitrification inhibitor.

Preferably, the vending may be in a dosage quantity or multiple thereof.

According to a fifth part of the 10th aspect of the present invention there is provided the use of 3-Ethynylpyridazine in the manufacture and/or vending of a soil treatment to effect nitrification inhibition and associated effects.

Preferably, a soil treatment to reduce nitrification and/or increase nitrogen use efficiency by plants.

According to a sixth part of the 10th aspect of the present invention there is provided the use substantially as described above wherein the nitrification inhibition reduces one or more of:
nitrous oxide emissions;
nitrate leaching; or
a combination thereof;
from soil.

According to a seventh part of the 10th aspect of the present invention there is provided the treatment to effect nitrification and associated effects using 3-Ethynylpyridazine.

According to an eighth part of the 10th aspect of the present invention there is provided the treatment of soil substantially as described above wherein 3-Ethynylpyridazine is co-applied with urea granules or other nitrogen containing fertiliser granules.

According to a ninth part of the 10th aspect of the present invention there is provided the use of 3-Ethynylpyridazine to coat urea fertiliser granules, or other nitrogen fertiliser granules.

According to a 10th part of the 10th aspect of the present invention there is provided a nitrogen fertiliser granule which is coated with 3-Ethynylpyridazine.

Preferably, the nitrogen fertiliser granule may be urea (or other ammonium forms of nitrogen or a nitrogen fertiliser that releases ammonium in soil).

According to an 11th part of the 10th aspect of the present invention there is provided the use of 3-Ethynylpyridazine as an additive to nitrogen containing liquid fertilisers.

According to a 12th part of the 10th aspect of the present invention there is provided the use of 3-Ethynylpyridazine in a particulate and/or liquid form as a soil treatment.

According to a 13th part of the 10th aspect of the present invention there is provided the manufacture and/or vending of 3-Ethynylpyridazine to coat nitrogen fertilisers.

According to a 14th part of the 10th aspect of the present invention there is provided the use of 3-Ethynylpyridazine to increase nitrogen use efficiency in crop/pasture systems, or to increase nitrogen use efficiency of fertilisers.

According to a 15th part of the 10th aspect of the present invention there is provided the use of 3-Ethynylpyridazine to interrupt a soil microbial nitrification process.

According to a 16th part of the 10th aspect of the present invention there is provided the use of 3-Ethynylpyridazine to improve pasture/plant growth.

According to a 17th part of the 10th aspect of the present invention there is provided the use of 3-Ethynylpyridazine as a treatment for urine patch areas in a pasture.

According to an 18th part of the 10th aspect of the present invention there is provided the use of co-application of 3-Ethynylpyridazine and a source of nitrogen to crops or pasture.

According to a 19th part of the 10th aspect of the present invention there is provided the vending of 3-Ethynylpyridazine for a use substantially as described above in relation to the 6th, 7th 9th, 11th, 12th,14th, 15th, 16th, 17th, and 18th parts of the 10th aspect of the present invention.

According to a 20th part of the 10th aspect of the present invention there is provided a method of treating agricultural land or other land with nitrate leaching or nitrous oxide emission issues comprising the application of 3-Ethynylpyridazine directly or indirectly thereto.

According to a 21st part of the 10th aspect of the present invention there is provided the co-application of 3-Ethynylpyridazine with a nitrogen fertilizer to inhibit nitrification in soil.

According to a 22nd part of the 10th aspect of the present invention there is provided a method of treating animal urine patches by applying 3-Ethynylpyridazine thereto either before, at the same time, or after, urine has been deposited.

According to a 23rd part of the 10th aspect of the present invention there is provided a method of treating soil by applying 3-Ethynylpyridazine to areas of soil which will be, or have been, subjected to urea, fertiliser, effluent, or other nitrogen source.

According to a 24th part of the 10th aspect of the present invention there is provided the application of 3-Ethynylpyridazine to soil, cropped land, or pasture.

According to a 25th part of the 10th aspect of the present invention there is provided the use of 3-Ethynylpyridazine substantially as described above wherein the dosage rate is selected from 0.5 kg/ha to 9 kg/ha.

According to a 26th part of the 10th aspect of the present invention there is provided the use of 3-Ethynylpyridazine substantially as described above wherein the dosage rate is 0.5 kg/ha.

According to a 27th part of the 10th aspect of the present invention there is provided the use of 3-Ethynylpyridazine to retard corrosion of building stones or stone statues.

According to a 28th part of the 10th aspect of the present invention there is provided a method of treating agricultural land or urban land comprising the vending of 3-Ethynylpyridazine in a manner selected from one or more of:
dosage quantity;
formulation type;
co-delivery with a source of nitrogen; or
a combination thereof,
which makes 3-Ethynylpyridazine suitable for treating land to reduce the environmental impacts of: animal urine; nitrogen fertilisers; animal manures; or effluent.

More information on 3-Ethynylpyridazine including chemical vendors can be found on the World-Wide Web at: achemblock.com/3-ethynyl-pyridazine.html.

11th Set of Aspects of the Invention: 3-Ethynyl-6-Methoxypyridazine (CAS 1019331-16-8)

The present invention also in an 11th set of aspects relates to a new surprising use of a 3-Ethynyl-6-methoxypyridazine having a structure the same as, or substantially similar to, that indicated in the formula below:

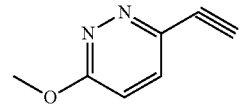

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

Aspects of the Invention

According to a first part of the 11$^{th}$ aspect of the present invention there is provided the use of 3-Ethynyl-6-methoxypyridazine as a nitrification inhibitor.

Preferably, there is a use of 3-Ethynyl-6-methoxypyridazine substantially as described above wherein the effective application rate in kg/ha is significantly less than that of DCD.

According to a second part of the 11$^{th}$ aspect of the present invention there is provided the use of 3-Ethynyl-6-methoxypyridazine as an active ingredient in a nitrification inhibitor formulation.

According to a third part of the 11$^{th}$ aspect of the present invention there is provided the use of 3-Ethynyl-6-methoxypyridazine in the manufacture of a nitrification inhibitor.

According to a fourth part of the 11$^{th}$ aspect of the present invention there is provided the vending 3-Ethynyl-6-methoxypyridazine, as a nitrification inhibitor, or for use in the manufacture of a nitrification inhibitor.

Preferably, the vending may be in a dosage quantity or multiple thereof.

According to a fifth part of the 11$^{th}$ aspect of the present invention there is provided the use of 3-Ethynyl-6-methoxypyridazine in the manufacture and/or vending of a soil treatment to effect nitrification inhibition and associated effects.

Preferably, a soil treatment to reduce nitrification and/or increase nitrogen use efficiency by plants.

According to a sixth part of the 11$^{th}$ aspect of the present invention there is provided the use substantially as described above wherein the nitrification inhibition reduces one or more of:

nitrous oxide emissions;
nitrate leaching; or a combination thereof;
from soil.

According to a seventh part of the 11$^{th}$ aspect of the present invention there is provided the treatment to effect nitrification and associated effects using 3-Ethynyl-6-methoxypyridazine.

According to an eighth part of the 11$^{th}$ aspect of the present invention there is provided the treatment of soil substantially as described above wherein 3-Ethynyl-6-methoxypyridazine is co-applied with urea granules or other nitrogen containing fertiliser granules.

According to a ninth part of the 11$^{th}$ aspect of the present invention there is provided the use of 3-Ethynyl-6-methoxypyridazine to coat urea fertiliser granules, or other nitrogen fertiliser granules.

According to a 10$^{th}$ part of the 11$^{th}$ aspect of the present invention there is provided a nitrogen fertiliser granule which is coated with 3-Ethynyl-6-methoxypyridazine.

Preferably, the nitrogen fertiliser granule may be urea (or other ammonium forms of nitrogen or a nitrogen fertiliser that releases ammonium in soil).

According to an 11$^{th}$ part of the 11$^{th}$ aspect of the present invention there is provided the use of 3-Ethynyl-6-methoxypyridazine as an additive to nitrogen containing liquid fertilisers.

According to a 12$^{th}$ part of the 11$^{th}$ aspect of the present invention there is provided the use of 3-Ethynyl-6-methoxypyridazine in a particulate and/or liquid form as a soil treatment.

According to a 13$^{th}$ part of the 11$^{th}$ aspect of the present invention there is provided the manufacture and/or vending of 3-Ethynyl-6-methoxypyridazine to coat nitrogen fertilisers.

According to a 14$^{th}$ part of the 11$^{th}$ aspect of the present invention there is provided the use of 3-Ethynyl-6-methoxypyridazine to increase nitrogen use efficiency in crop/pasture systems, or to increase nitrogen use efficiency of fertilisers.

According to a 15$^{th}$ part of the 11$^{th}$ aspect of the present invention there is provided the use of 3-Ethynyl-6-methoxypyridazine to interrupt a soil microbial nitrification process.

According to a 16$^{th}$ part of the 11$^{th}$ aspect of the present invention there is provided the use of 3-Ethynyl-6-methoxypyridazine to improve pasture/plant growth.

According to a 17$^{th}$ part of the 11$^{th}$ aspect of the present invention there is provided the use of 3-Ethynyl-6-methoxypyridazine as a treatment for urine patch areas in a pasture.

According to an 18$^{th}$ part of the 11$^{th}$ aspect of the present invention there is provided the use of co-application of 3-Ethynyl-6-methoxypyridazine and a source of nitrogen to crops or pasture.

According to a 19$^{th}$ part of the 11$^{th}$ aspect of the present invention there is provided the vending of 3-Ethynyl-6-methoxypyridazine for a use substantially as described above in relation to the 6$^{th}$, 7$^{th}$ 9$^{th}$, 11$^{th}$, 12$^{th}$,14$^{th}$, 15$^{th}$, 16$^{th}$, 17$^{th}$, and 18$^{th}$ parts of the 11$^{th}$ aspect of the present invention.

According to a 20$^{th}$ part of the 11$^{th}$ aspect of the present invention there is provided a method of treating agricultural land or other land with nitrate leaching or nitrous oxide emission issues comprising the application of 3-Ethynyl-6-methoxypyridazine directly or indirectly thereto.

According to a 21$^{st}$ part of the 11$^{th}$ aspect of the present invention there is provided the co-application of 3-Ethynyl-6-methoxypyridazine with a nitrogen fertilizer to inhibit nitrification in soil.

According to a 22$^{nd}$ part of the 11$^{th}$ aspect of the present invention there is provided a method of treating animal urine patches by applying 3-Ethynyl-6-methoxypyridazine thereto either before, at the same time, or after, urine has been deposited.

According to a 23$^{rd}$ part of the 11$^{th}$ aspect of the present invention there is provided a method of treating soil by applying 3-Ethynyl-6-methoxypyridazine to areas of soil which will be, or have been, subjected to urea, fertiliser, effluent, or other nitrogen source.

According to a 24$^{th}$ part of the 11$^{th}$ aspect of the present invention there is provided the application of 3-Ethynyl-6-methoxypyridazine to soil, cropped land, or pasture.

According to a 25$^{th}$ part of the 11$^{th}$ aspect of the present invention there is provided the use of 3-Ethynyl-6-methoxypyridazine substantially as described above wherein the dosage rate is selected from 2 kg/ha to 10 kg/ha.

According to a 26$^{th}$ part of the 11$^{th}$ aspect of the present invention there is provided the use of 3-Ethynyl-6-methoxypyridazine substantially as described above wherein the dosage rate is 2 kg/ha.

According to a 27$^{th}$ part of the 11$^{th}$ aspect of the present invention there is provided the use of 3-Ethynyl-6-methoxypyridazine to retard corrosion of building stones or stone statues.

According to a 28$^{th}$ part of the 11$^{th}$ aspect of the present invention there is provided a method of treating agricultural land or urban land comprising the vending of 3-Ethynyl-6-methoxypyridazine in a manner selected from one or more of:

dosage quantity;
formulation type;
co-delivery with a source of nitrogen; or
a combination thereof,
which makes 3-Ethynyl-6-methoxypyridazine suitable for treating land to reduce the environmental impacts of: animal urine; nitrogen fertilisers; animal manures; or effluent.

More information on 3-Ethynyl-6-methoxypyridazine including chemical vendors can be found on the internet at: chem-space.com/CSSB00011011728-FA5855.

12th Set of Aspects of the Invention: 2-Ethynylpyrazine (CAS 153800-11-4)

The present invention also in a 12th set of aspects relates to a new surprising use of 2-ethynylpyrazine having a structure the same as, or substantially similar to, that indicated in the formula below:

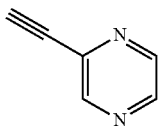

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the 12th aspect of the present invention there is provided the use of 2-ethynylpyrazine as a nitrification inhibitor.

Preferably, there is a use of 2-ethynylpyrazine substantially as described above wherein the effective application rate in kg/ha is significantly less than that of DCD.

According to a second part of the 12th aspect of the present invention there is provided the use of 2-ethynylpyrazine as an active ingredient in a nitrification inhibitor formulation.

According to a third part of the 12th aspect of the present invention there is provided the use of 2-ethynylpyrazine in the manufacture of a nitrification inhibitor.

According to a fourth part of the 12th aspect of the present invention there is provided the vending of 2-ethynylpyrazine, as a nitrification inhibitor, or for use in the manufacture of a nitrification inhibitor.

Preferably, the vending may be in a dosage quantity or multiple thereof.

According to a fifth part of the 12th aspect of the present invention there is provided the use of 2-ethynylpyrazine in the manufacture and/or vending of a soil treatment to effect nitrification inhibition and associated effects.

Preferably, a soil treatment to reduce nitrification and/or increase nitrogen use efficiency by plants.

According to a sixth part of the 12th aspect of the present invention there is provided the use of 2-ethynylpyrazine substantially as described above wherein the nitrification inhibition reduces one or more of:
nitrous oxide emissions;
nitrate leaching; or
a combination thereof;
from soil.

According to a seventh part of the 12th aspect of the present invention there is provided a treatment to effect nitrification and associated effects using 2-ethynylpyrazine.

According to an eighth part of the 12th aspect of the present invention there is provided the treatment of soil substantially as described above wherein 2-ethynylpyrazine is co-applied with urea granules or other nitrogen containing fertiliser granules.

According to a ninth part of the 12th aspect of the present invention there is provided the use of 2-ethynylpyrazine to coat urea fertiliser granules, or other nitrogen fertiliser granules.

According to a 10th part of the 12th aspect of the present invention there is provided a nitrogen fertiliser granule which is coated with 2-ethynylpyrazine.

Preferably, the nitrogen fertiliser granule may be urea (or other ammonium forms of nitrogen or a nitrogen fertiliser that releases ammonium in soil).

According to an 11th part of the 12th aspect of the present invention there is provided the use of 2-ethynylpyrazine as an additive to nitrogen containing liquid fertilisers.

According to a 12th part of the 12th aspect of the present invention there is provided the use of 2-ethynylpyrazine in a particulate and/or liquid form as a soil treatment.

According to a 13th part of the 12th aspect of the present invention there is provided the manufacture and/or vending of 2-ethynylpyrazine to coat nitrogen fertilisers.

According to a 14th part of the 12th aspect of the present invention there is provided the use of 2-ethynylpyrazine to increase nitrogen use efficiency in crop/pasture systems, or to increase nitrogen use efficiency of fertilisers.

According to a 15th part of the 12th aspect of the present invention there is provided the use of 2-ethynylpyrazine to interrupt a soil microbial nitrification process.

According to a 16th part of the 12th aspect of the present invention there is provided the use of 2-ethynylpyrazine to improve pasture/plant growth.

According to a 17th part of the 12th aspect of the present invention there is provided the use of 2-ethynylpyrazine as a treatment for urine patch areas in a pasture.

According to an 18th part of the 12th aspect of the present invention there is provided the use of co-application of 2-ethynylpyrazine and a source of nitrogen to crops or pasture.

According to a 19th part of the 12th aspect of the present invention there is provided the vending of 2-ethynylpyrazine for a use substantially as described above in relation to the 6th, 7th 9th, 11th, 12th,14th, 15th, 16th, 17th, and 18th parts of the 12th aspect of the present invention.

According to a 20th part of the 12th aspect of the present invention there is provided a method of treating agricultural land or other land with nitrate leaching or nitrous oxide emission issues comprising the application of 2-ethynylpyrazine directly or indirectly thereto.

According to a 21st part of the 12th aspect of the present invention there is provided the co-application of 2-ethynylpyrazine with a nitrogen fertilizer to inhibit nitrification in soil.

According to a 22nd part of the 12th aspect of the present invention there is provided a method of treating animal urine patches by applying 2-ethynylpyrazine there to either before, at the same time, or after, urine has been deposited.

According to a 23rd part of the 12th aspect of the present invention there is provided a method of treating soil by applying 2-ethynylpyrazine to areas of soil which will be, or have been, subjected to urea, fertiliser, effluent, or other nitrogen source.

According to a 24th part of the 12th aspect of the present invention there is provided the application of 2-ethynylpyrazine to soil, cropped land, or pasture.

According to a 25th part of the 12th aspect of the present invention there is provided the use of 2-ethynylpyrazine substantially as described above as wherein the dosage rate is selected from 2 kg/ha to 9 kg/ha.

According to a 26th part of the 12th aspect of the present invention there is provided the use of 2-ethynylpyrazine substantially as described above wherein the dosage rate is 2 kg/ha.

According to a 27th part of the 12th aspect of the present invention there is provided a method of treating agricultural land or urban land comprising the vending of 2-ethynylpyrazine in a manner selected from one or more of:
  dosage quantity;
  formulation type;
  co-delivery with a source of nitrogen; or
  a combination thereof,
which makes 2-ethynylpyrazine suitable for treating land to reduce the environmental impacts of: animal urine; nitrogen fertilisers; animal manures; or effluent.

More information on 2-ethynylpyrazine including chemical vendors can be found on the internet at: pubchem.ncbi.nlm.nih.gov/compound/15639205.

13th Set of Aspects of the Invention: 2-Ethynyl-5-Methoxypyrazine (CAS 1374115-62-4)

The present invention also in a 13th set of aspects relates to a new surprising use of 2-Ethynyl-5-methoxypyrazine having a structure the same as, or substantially similar to, that indicated in the formula below:

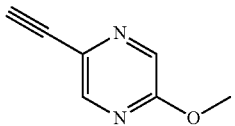

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the 13th aspect of the present invention there is provided the use of 2-Ethynyl-5-methoxypyrazine as a nitrification inhibitor.

Preferably, there is a use of 2-Ethynyl-5-methoxypyrazine substantially as described above wherein the effective application rate in kg/ha is significantly less than that of DCD.

According to a second part of the 13th aspect of the present invention there is provided the use of 2-Ethynyl-5-methoxypyrazine as an active ingredient in a nitrification inhibitor formulation.

According to a third part of the 13th aspect of the present invention there is provided the use of 2-Ethynyl-5-methoxypyrazine in the manufacture of a nitrification inhibitor.

According to a fourth part of the 13th aspect of the present invention there is provided the vending of 2-Ethynyl-5-methoxypyrazine, as a nitrification inhibitor, or for use in the manufacture of a nitrification inhibitor.

Preferably, the vending may be in a dosage quantity or multiple thereof.

According to a fifth part of the 13th aspect of the present invention there is provided the use of 2-Ethynyl-5-methoxypyrazine in the manufacture and/or vending of a soil treatment to effect nitrification inhibition and associated effects.

Preferably, a soil treatment to reduce nitrification and/or increase nitrogen use efficiency by plants.

According to a sixth part of the 13th aspect of the present invention there is provided the use of 2-Ethynyl-5-methoxypyrazine substantially as described above wherein the nitrification inhibition reduces one or more of:
  nitrous oxide emissions;
  nitrate leaching; or
  a combination thereof;
from soil.

According to a seventh part of the 13th aspect of the present invention there is provided the treatment to effect nitrification inhibition and associated effects using 2-Ethynyl-5-methoxypyrazine.

According to an eighth part of the 13th aspect of the present invention there is provided the treatment of soil substantially as described above wherein 2-Ethynyl-5-methoxypyrazine is co-applied with urea granules or other nitrogen containing fertiliser granules.

According to a ninth part of the 13th aspect of the present invention there is provided the use of 2-Ethynyl-5-methoxypyrazine to coat urea fertiliser granules, or other nitrogen fertiliser granules.

According to a 10th part of the 13th aspect of the present invention there is provided a nitrogen fertiliser granule which is coated with 2-Ethynyl-5-methoxypyrazine.

Preferably, the nitrogen fertiliser granule may be urea (or other ammonium forms of nitrogen or a nitrogen fertiliser that releases ammonium in soil).

According to an 11th part of the 13th aspect of the present invention there is provided the use of 2-Ethynyl-5-methoxypyrazine as an additive to nitrogen containing liquid fertilisers.

According to a 12th part of the 13th aspect of the present invention there is provided the use of 2-Ethynyl-5-methoxypyrazine in a particulate and/or liquid form as a soil treatment.

According to a 13th part of the 13th aspect of the present invention there is provided the manufacture and/or vending of 2-Ethynyl-5-methoxypyrazine to coat nitrogen fertilisers.

According to a 14th part of the 13th aspect of the present invention there is provided the use of 2-Ethynyl-5-methoxypyrazine to increase nitrogen use efficiency in crop/pasture systems, or to increase nitrogen use efficiency of fertilisers.

According to a 15th part of the 13th aspect of the present invention there is provided the use of 2-Ethynyl-5-methoxypyrazine to interrupt a soil microbial nitrification process.

According to a 16th part of the 13th aspect of the present invention there is provided the use of 2-Ethynyl-5-methoxypyrazine to improve pasture/plant growth.

According to a 17th part of the 13th aspect of the present invention there is provided the use of 2-Ethynyl-5-methoxypyrazine as a treatment for urine patch areas in a pasture.

According to an 18th part of the 13th aspect of the present invention there is provided the use of co-application of 2-Ethynyl-5-methoxypyrazine and a source of nitrogen to crops or pasture.

According to a 19th part of the 13th aspect of the present invention there is provided the vending of 2-Ethynyl-5-methoxypyrazine for a use substantially as described above in relation to the 6th, 7th 9th, 11th, 12th,14th, 15th, 16th, 17th, and 18th parts of the 13th aspect of the present invention.

According to a 20th part of the 13th aspect of the present invention there is provided a method of treating agricultural land or other land with nitrate leaching or nitrous oxide emission issues comprising the application of 2-Ethynyl-5-methoxypyrazine directly or indirectly thereto.

According to a 21st part of the 14th aspect of the present invention there is provided the co-application of 2-Ethynyl-5-methoxypyrazine with a nitrogen fertilizer to inhibit nitrification in soil.

According to a 22nd part of the 13th aspect of the present invention there is provided a method of treating animal urine patches by applying 2-Ethynyl-5-methoxypyrazine there to either before, at the same time, or after, urine has been deposited.

According to a 23rd part of the 13th aspect of the present invention there is provided a method of treating soil by applying 2-Ethynyl-5-methoxypyrazine to areas of soil which will be, or have been, subjected to urea, fertiliser, effluent, or other nitrogen source.

According to a 24th part of the 13th aspect of the present invention there is provided the application of 2-Ethynyl-5-methoxypyrazine to soil, cropped land, or pasture.

According to a 25th part of the 13th aspect of the present invention there is provided the use of 2-Ethynyl-5-methoxypyrazine substantially as described above wherein the dosage rate is selected from 2 kg/ha to 10 kg/ha.

According to a 26th part of the 14th aspect of the present invention there is provided the use of 2-Ethynyl-5-methoxypyrazine substantially as described above wherein the dosage rate is 2 kg/ha.

According to a 27th part of the 13th aspect of the present invention there is provided a method of treating agricultural land or urban land comprising the vending of 2-Ethynyl-5-methoxypyrazine in a manner selected from one or more of:
  dosage quantity;
  formulation type;
  co-delivery with a source of nitrogen; or
  a combination thereof,
which makes 2-Ethynyl-5-methoxypyrazine suitable for treating land to reduce the environmental impacts of: animal urine; nitrogen fertilisers; animal manures; or effluent.

More information on 2-Ethynyl-5-methoxypyrazine including chemical vendors can be found on the internet at: chem-space.com/CSSB00010369260-B1A2BE.

14th Set of Aspects of the Invention: 4-Ethynylanisole (CAS 768-60-5)

The present invention in a 14th of aspects relates to a new surprising use of 4-Ethynylanisole (aka 1-ethynyl-4-methoxybenzene) having a structure the same as, or substantially similar to, that indicated in the formula below:

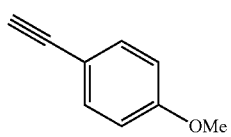

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the 14th aspect of the present invention there is provided the use of 4-Ethynylanisole as a nitrification inhibitor.

Preferably, there is a use of 4-Ethynylanisole substantially as described above wherein the effective application rate in kg/ha is significantly less than that of DCD.

According to a second part of the 14th aspect of the present invention there is provided the use of 4-Ethynylanisole as an active ingredient in a nitrification inhibitor formulation.

According to a third part of the 14th aspect of the present invention there is provided the use of 4-Ethynylanisole in the manufacture of a nitrification inhibitor.

According to a fourth part of the 14th aspect of the present invention there is provided the vending of 4-Ethynylanisole, as a nitrification inhibitor, or for use in the manufacture of a nitrification inhibitor.

Preferably, the vending may be in a dosage quantity or multiple thereof.

According to a fifth part of the 14th aspect of the present invention there is provided the use of 2-4-Ethynylanisole in the manufacture and/or vending of a soil treatment to effect nitrification inhibition and associated effects.

Preferably, a soil treatment to reduce nitrification and/or increase nitrogen use efficiency by plants.

According to a sixth part of the 14th aspect of the present invention there is provided the use substantially as described above wherein the nitrification inhibition reduces one or more of:
  nitrous oxide emissions;
  nitrate leaching; or
  a combination thereof;
from soil.

According to a seventh part of the 14th aspect of the present invention there is provided the treatment of soil to effect nitrification inhibition and associated effects using 4-Ethynylanisole.

According to an eighth part of the 14th aspect of the present invention there is provided the treatment of soil substantially as described above wherein 4-Ethynylanisole is co-applied with urea granules or other nitrogen containing fertiliser granules.

According to a ninth part of the 14th aspect of the present invention there is provided the use of 4-Ethynylanisole to coat urea fertiliser granules, or other nitrogen fertiliser granules.

According to a 10th part of the 14th aspect of the present invention there is provided a nitrogen fertiliser granule which is coated with 4-Ethynylanisole.

Preferably, the nitrogen fertiliser granule may be urea (or other ammonium forms of nitrogen or a nitrogen fertiliser that releases ammonium in soil).

According to a 11th part of the 14th aspect of the present invention there is provided the use of 4-Ethynylanisole as an additive to nitrogen containing liquid fertilisers.

According to an 12th part of the 14th aspect of the present invention there is provided the use of 4-Ethynylanisole in a particulate and/or liquid form as a soil treatment.

According to a 13th part of the 14th aspect of the present invention there is provided the manufacture and/or vending of 4-Ethynylanisole to coat nitrogen fertilisers.

According to a 14th part of the 14th aspect of the present invention there is provided the use of 4-Ethynylanisole to increase nitrogen use efficiency in crop/pasture systems, or to increase nitrogen use efficiency of fertilisers.

According to a 15th part of the 14th aspect of the present invention there is provided the use of 4-Ethynylanisole to interrupt a soil microbial nitrification process.

According to an 16th part of the 14th aspect of the present invention there is provided the use of 4-Ethynylanisole to improve pasture/plant growth.

According to a 17th part of the 14th aspect of the present invention there is provided the use of 4-Ethynylanisole as a treatment for urine patch areas in a pasture.

According to a 18th part of the 14th aspect of the present invention there is provided the use of co-application of 4-Ethynylanisole and a source of nitrogen to crops or pasture.

According to a 19th part of the 14th aspect of the present invention there is provided the vending of 4-Ethynylanisole for a use substantially as described above in relation to the 6th, 7th 9th, 11th, 12th, 14th, 15th, 16th, 17th, and 18th parts of the 14th aspect of the present invention.

According to a 20th part of the 14th aspect of the present invention there is provided a method of treating agricultural land or other land with nitrate leaching or nitrous oxide emission issues comprising the application of 4-Ethynylanisole directly or indirectly thereto.

According to a 21st part of the 14th aspect of the present invention there is provided the co-application of 4-Ethynylanisole with a nitrogen fertilizer to inhibit nitrification in soil.

According to a 22nd part of the 14th aspect of the present invention there is provided a method of treating animal urine patches by applying 4-Ethynylanisole thereto either before, at the same time, or after, urine has been deposited.

According to a 23rd part of the 14th aspect of the present invention there is provided a method of treating soil by applying 4-Ethynylanisole to areas of soil which will be, or have been, subjected to urea, fertiliser, effluent, or other nitrogen source.

According to a 24th part of the 14th aspect of the present invention there is provided the application of 4-Ethynylanisole to soil, cropped land, or pasture.

According to a 25th part of the 14th aspect of the present invention there is provided the use of 4-Ethynylanisole substantially as described above wherein the dosage rate is selected from 1 kg/ha to 9 kg/ha.

According to a 26th part of the 14th aspect of the present invention there is provided the use of 4-Ethynylanisole substantially as described above wherein the dosage rate is 1 kg/ha.

According to a 27th part of the 14th aspect of the present invention there is provided the use of 4-Ethynylanisole to retard corrosion of building stones or stone statues.

According to a 28th part of the 14th aspect of the present invention there is provided a method of treating agricultural land or urban land comprising the vending of 4-Ethynylanisole a manner selected from one or more of:
  dosage quantity;
  formulation type;
  co-delivery with a source of nitrogen; or
  a combination thereof,
which makes 4-Ethynylanisole suitable for treating land to reduce the environmental impacts of: animal urine; nitrogen fertilisers; animal manures; or effluent.

More information on 4-Ethynylanisole including chemical vendors can be found on the World-Wide-Web at: sigmaaldrich.com/catalog/product/aldrich/206490.

15th Set of Aspects of the Invention: 1-Ethoxy-4-Ethynylbenzene (CAS 79887-14-2)

The present invention also in a 15th set of aspects relates to a new surprising use of 1-ethoxy-4-ethynylbenzene having a structure the same as, or substantially similar to, that indicated in the formula below:

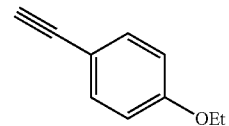

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the 15th aspect of the present invention there is provided the use of 1-ethoxy-4-ethynylbenzene as a nitrification inhibitor.

Preferably, there is a use of 1-ethoxy-4-ethynylbenzene substantially as described above wherein the effective application rate in kg/ha is significantly less than that of DCD.

According to a second part of the 15th aspect of the present invention there is provided the use of 1-ethoxy-4-ethynylbenzene as an active ingredient in a nitrification inhibitor formulation.

According to a third part of the 15th aspect of the present invention there is provided the use of 1-ethoxy-4-ethynylbenzene in the manufacture of a nitrification inhibitor.

According to a fourth part of the 15th aspect of the present invention there is provided the vending of 1-ethoxy-4-ethynylbenzene, as a nitrification inhibitor, or for use in the manufacture of a nitrification inhibitor.

Preferably, the vending may be in a dosage quantity or multiple thereof.

According to a fifth part of the 15th aspect of the present invention there is provided the use of 1-ethoxy-4-ethynylbenzene in the manufacture and/or vending of a soil treatment to effect nitrification inhibition and associated effects.

Preferably, a soil treatment to reduce nitrification and/or increase nitrogen use efficiency by plants.

According to a sixth part of the 15th aspect of the present invention there is provided the use of 1-ethoxy-4-ethynylbenzene substantially as described above wherein the nitrification inhibition reduces one or more of:
  nitrous oxide emissions;
  nitrate leaching; or
  a combination thereof;
from soil.

According to a seventh part of the 15th aspect of the present invention there is provided the treatment to effect nitrification inhibition and associated effects using 1-ethoxy-4-ethynylbenzene.

According to an eighth part of the 15th aspect of the present invention there is provided the treatment of soil substantially as described above wherein 1-ethoxy-4-ethynylbenzene is co-applied with urea granules or other nitrogen containing fertiliser granules.

According to a ninth part of the 15th aspect of the present invention there is provided the use of 1-ethoxy-4-ethynylbenzene to coat urea fertiliser granules, or other nitrogen fertiliser granules.

According to a 10th part of the 15th aspect of the present invention there is provided a nitrogen fertiliser granule which is coated with 1-ethoxy-4-ethynylbenzene.

Preferably, the nitrogen fertiliser granule may be urea (or other ammonium forms of nitrogen or a nitrogen fertiliser that releases ammonium in soil).

According to an 11th part of the 15th aspect of the present invention there is provided the use of 1-ethoxy-4-ethynylbenzene as an additive to nitrogen containing liquid fertilisers.

According to a 12th part of the 15th aspect of the present invention there is provided the use of 1-ethoxy-4-ethynylbenzene in a particulate and/or liquid form as a soil treatment.

According to a 13th part of the 15th aspect of the present invention there is provided the manufacture and/or vending of 1-ethoxy-4-ethynylbenzene to coat nitrogen fertilisers.

According to a 14th part of the 15th aspect of the present invention there is provided the use of 1-ethoxy-4-ethynylbenzene to increase nitrogen use efficiency in crop/pasture systems, or to increase nitrogen use efficiency of fertilisers.

According to a 15th part of the 15th aspect of the present invention there is provided the use of 1-ethoxy-4-ethynylbenzene to interrupt a soil microbial nitrification process.

According to a 16th part of the 15th aspect of the present invention there is provided the use of 1-ethoxy-4-ethynylbenzene to improve pasture/plant growth.

According to a 17th part of the 15th aspect of the present invention there is provided the use of 1-ethoxy-4-ethynylbenzene as a treatment for urine patch areas in a pasture.

According to an 18th part of the 15th aspect of the present invention there is provided the use of co-application of 1-ethoxy-4-ethynylbenzene and a source of nitrogen to crops or pasture.

According to a 19th part of the 15th aspect of the present invention there is provided the vending of 1-ethoxy-4-ethynylbenzene for a use substantially as described above in relation to the 6th, 7th 9th, 11th, 12th,14th, 15th, 16th, 17th, and 18th parts of the 15th aspect of the present invention.

According to a 20th part of the 15th aspect of the present invention there is provided a method of treating agricultural land or other land with nitrate leaching or nitrous oxide emission issues comprising the application of 1-ethoxy-4-ethynylbenzene directly or indirectly thereto.

According to a 21st part of the 15th aspect of the present invention there is provided the co-application of 1-ethoxy-4-ethynylbenzene with a nitrogen fertilizer to inhibit nitrification in soil.

According to a 22nd part of the 15th aspect of the present invention there is provided a method of treating animal urine patches by applying 1-ethoxy-4-ethynylbenzene there to either before, at the same time, or after, urine has been deposited.

According to a 23rd part of the 15th aspect of the present invention there is provided a method of treating soil by applying 1-ethoxy-4-ethynylbenzene to areas of soil which will be, or have been, subjected to urea, fertiliser, effluent, or other nitrogen source.

According to a 24th part of the 15th aspect of the present invention there is provided the application of 1-ethoxy-4-ethynylbenzene to soil, cropped land, or pasture.

According to a 25th part of the 15th aspect of the present invention there is provided the use of 1-ethoxy-4-ethynylbenzene substantially as described above wherein the dosage rate is selected from 2 kg/ha to 9 kg/ha.

According to a 26th part of the 15th aspect of the present invention there is provided the use of 1-ethoxy-4-ethynylbenzene substantially as described above wherein the dosage rate is 2 kg/ha.

According to a 27th part of the 15th aspect of the present invention there is provided a method of treating agricultural land or urban land comprising the vending of 1-ethoxy-4-ethynylbenzene in a manner selected from one or more of:
 dosage quantity;
 formulation type;
 co-delivery with a source of nitrogen; or
 a combination thereof,
which makes 1-ethoxy-4-ethynylbenzene suitable for treating land to reduce the environmental impacts of: animal urine; nitrogen fertilisers; animal manures; or effluent.

More information on 1-ethoxy-4-ethynylbenzene including chemical vendors can be found on the internet at: pubchem.ncbi.nlm.nih.gov/compound/4-Ethoxyphenylacetylene.

16th Set of Aspects of the Invention: 1,4-Diethynylbenzene (CAS 935-14-8)

The present invention also in a 16th set of aspects relates to a new surprising use of 1,4-diethynylbenzene having a structure the same as, or substantially similar to, that indicated in the formula below:

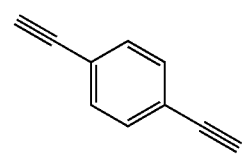

in relation to its applicability in reducing $NO_3^-$ leaching and $N_2O$ emissions by preventing/inhibiting soil microbes from converting ammonia to nitrate. The relationship between the inhibition of nitrification in the soil and the reduction in nitrate leaching and nitrous oxide emissions is illustrated in FIG. 1(A) (Di and Cameron 2016). It has been shown conclusively that both nitrate leaching and $N_2O$ emissions can be reduced by inhibiting the nitrification process with a nitrification inhibitor (Di and Cameron, 2016).

According to a first part of the 16th aspect of the present invention there is provided the use of 1,4-diethynylbenzene as a nitrification inhibitor.

Preferably, there is a use of 1,4-diethynylbenzene substantially as described above wherein the effective application rate in kg/ha is significantly less than that of DCD.

According to a second part of the 16th aspect of the present invention there is provided the use of 1,4-diethynylbenzene as an active ingredient in a nitrification inhibitor formulation.

According to a third part of the 16th aspect of the present invention there is provided the use of 1,4-diethynylbenzene in the manufacture of a nitrification inhibitor.

According to a fourth part of the 16th aspect of the present invention there is provided the vending of 1,4-diethynylbenzene, as a nitrification inhibitor, or for use in the manufacture of a nitrification inhibitor.

Preferably, the vending may be in a dosage quantity or multiple thereof.

According to a fifth part of the 16th aspect of the present invention there is provided the use of 1,4-diethynylbenzene in the manufacture and/or vending of a soil treatment to effect nitrification inhibition and associated effects.

Preferably, a soil treatment to reduce nitrification and/or increase nitrogen use efficiency by plants.

According to a sixth part of the $16^{th}$ aspect of the present invention there is provided the use of 1,4-diethynylbenzene substantially as described above wherein the nitrification inhibition reduces one or more of:
nitrous oxide emissions;
nitrate leaching; or
a combination thereof;
from soil.

According to a seventh part of the $16^{th}$ aspect of the present invention there is provided the treatment to effect nitrification inhibition and associated effects using 1,4-diethynylbenzene.

According to an eighth part of the $16^{th}$ aspect of the present invention there is provided the treatment of soil substantially as described above wherein 1,4-diethynylbenzene is co-applied with urea granules or other nitrogen containing fertiliser granules.

According to a ninth part of the $16^{th}$ aspect of the present invention there is provided the use of 1,4-diethynylbenzene to coat urea fertiliser granules, or other nitrogen fertiliser granules.

According to a $10^{th}$ part of the $17^{th}$ aspect of the present invention there is provided a nitrogen fertiliser granule which is coated with 1,4-diethynylbenzene.

Preferably, the nitrogen fertiliser granule may be urea (or other ammonium forms of nitrogen or a nitrogen fertiliser that releases ammonium in soil).

According to an $11^{th}$ part of the $16^{th}$ aspect of the present invention there is provided the use of 1,4-diethynylbenzene as an additive to nitrogen containing liquid fertilisers.

According to a $12^{th}$ part of the $16^{th}$ aspect of the present invention there is provided the use of 1,4-diethynylbenzene in a particulate and/or liquid form as a soil treatment.

According to a $13^{th}$ part of the $16^{th}$ aspect of the present invention there is provided the manufacture and/or vending of 1,4-diethynylbenzene to coat nitrogen fertilisers.

According to a $14^{th}$ part of the $16^{th}$ aspect of the present invention there is provided the use of 1,4-diethynylbenzene to increase nitrogen use efficiency in crop/pasture systems, or to increase nitrogen use efficiency of fertilisers.

According to a $15^{th}$ part of the $16^{th}$ aspect of the present invention there is provided the use of 1,4-diethynylbenzene to interrupt a soil microbial nitrification process.

According to a $16^{th}$ part of the $16^{th}$ aspect of the present invention there is provided the use of 1,4-diethynylbenzene to improve pasture/plant growth.

According to a $17^{th}$ part of the $16^{th}$ aspect of the present invention there is provided the use of 1,4-diethynylbenzene as a treatment for urine patch areas in a pasture.

According to an $18^{th}$ part of the $16^{th}$ aspect of the present invention there is provided the use of co-application of 1,4-diethynylbenzene and a source of nitrogen to crops or pasture.

According to a $19^{th}$ part of the $16^{th}$ aspect of the present invention there is provided the vending of 1,4-diethynylbenzene for a use substantially as described above in relation to the $6^{th}$, $7^{th}$ $9^{th}$, $11^{th}$, $12^{th}$, $14^{th}$, $15^{th}$, $16^{th}$, $17^{th}$, and $18^{th}$ parts of the $16^{th}$ aspect of the present invention.

According to a $20^{th}$ part of the $16^{th}$ aspect of the present invention there is provided a method of treating agricultural land or other land with nitrate leaching or nitrous oxide emission issues comprising the application of 1,4-diethynylbenzene directly or indirectly thereto.

According to a $21^{st}$ part of the $16^{th}$ aspect of the present invention there is provided the co-application of 1,4-diethynylbenzene with a nitrogen fertilizer to inhibit nitrification in soil.

According to a $22^{nd}$ part of the second aspect of the present invention there is provided a method of treating animal urine patches by applying 1,4-diethynylbenzene there to either before, at the same time, or after, urine has been deposited.

According to a $23^{rd}$ part of the $16^{th}$ aspect of the present invention there is provided a method of treating soil by applying 1,4-diethynylbenzene to areas of soil which will be, or have been, subjected to urea, fertiliser, effluent, or other nitrogen source.

According to a $24^{th}$ part of the $16^{th}$ aspect of the present invention there is provided the application of 1,4-diethynylbenzene to soil, cropped land, or pasture.

According to a $25^{th}$ part of the $16^{th}$ aspect of the present invention there is provided the use of 1,4-diethynylbenzene substantially as described above wherein the dosage rate is selected from 2 kg/ha to 9 kg/ha.

According to a $26^{th}$ part of the $16^{th}$ aspect of the present invention there is provided the use of 1,4-diethynylbenzene substantially as described above wherein the dosage rate is 2 kg/ha.

According to a $27^{th}$ part of the $16^{th}$ aspect of the present invention there is provided a method of treating agricultural land or urban land comprising the vending of 1,4-diethynylbenzene in a manner selected from one or more of:
dosage quantity;
formulation type;
co-delivery with a source of nitrogen; or
a combination thereof,
which makes 1,4-diethynylbenzene suitable for treating land to reduce the environmental impacts of: animal urine; nitrogen fertilisers; animal manures; or effluent.

More information on 1,4-diethynylbenzene including chemical vendors can be found on the World-Wide-Web at: sigmaaldrich.com/catalog/product/aldrich/632090.

BEST MODES FOR CARRYING OUT THE INVENTION

FIG. 1(A) is a simplified diagram showing animal urine-N as the main source for $N_2O$ emissions and $NO_3^-$ leaching losses in a grazed grassland and the point of intervention by nitrification inhibitor. If nitrogen fertilisers are applied to the soil rather than animal urine, such as urea or other fertilisers that release ammonium in the soil, then similar reactions can take place as shown in the diagram. Animal urine N is used as an example to illustrate the nitrification process, sources for nitrate leaching and nitrous oxide emissions, and the point of intervention using nitrification inhibitors to treat the soil which has been, or will be, or substantially at the same time, subjected to animal urine, nitrogen fertilizer or animal effluent.

The problem to be solved by the present invention was to find new nitrification inhibitors—which have the desired characteristics enabling said inhibitors to be used in farming applications in place of DCD to redress the aforementioned problems associated with nitrogen.

The inventors in their quest to solve the problem screened over 25,000 compounds by in silico screening against a modelled ammonia monooxygenase enzyme structure.

From this, about 5000 compounds were then screened in vitro using a high throughput phenotypic screening method that was optimised for the identification of compounds which specifically inhibited the oxidation of ammonium to nitrite. The phenotypic screening involved assessing the nitrification inhibition potency of the selected 5000 compounds against a key ammonia oxidizing bacterium responsible for ammonia oxidation in the soil, *Nitrosomonas europaea*, in 96-well microtiter plates. *N. europaea* cells were grown in the presence of an ammonium source, and the potential of putative nitrification inhibitors to inhibit the production of nitrite ($NO_2$) was measured relative to untreated cells.

Some of the key desired characteristics of the new potential nitrification inhibitor compounds included:
High nitrification inhibition potency at low (i.e. much less than the 10 kg/ha used for DCD) application rates;
Low toxicity;
Otherwise meeting various food and environmental regulatory requirements or standards.

Of the 5000 compounds screened, about 150 showed inhibition properties against *N. europaea* in vitro. The compounds that inhibited nitrification in the phenotypic screening and met these criteria were subsequently selected and tested for their nitrification inhibition efficacy in the critically important soil testing, and about 30 compounds showed sufficient inhibition on nitrification in the soil testing.

The costs for testing potential compounds is not cheap and so far this discovery programme has cost more than $3 million.

A summary of selected compounds initially found to either work or not work as nitrification inhibitors is detailed in Table 1 below.

TABLE 1

| FAMILY | IUPAC name | Structure | Inhib(%) |
|---|---|---|---|
| Benzenes | 1-ethynyl-4-methoxybenzene | 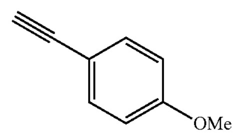 | 100 |
| | 1-ethoxy-4-ethynylbenzene | | 100 |
| | 1,4-diethynylbenzene | | 100 |
| | 4-ethynylphenol | | 0 |
| | 1-ethynyl-4-pentoxybenzene | | 2 |
| | 1-ethynyl-4-(trifluoromethoxy)benzene | | 8 |
| Pyridines (including N-oxide) | 2-ethynyl-5-methoxypyridine | 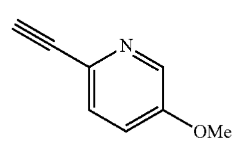 | 100 |
| | 5-ethynyl-2-methoxypyridine | | 100 |

TABLE 1-continued

| FAMILY | IUPAC name | Structure | Inhib(%) |
|---|---|---|---|
| | 2,5-diethynylpyridine | | 100 |
| | 3-ethynylpyridine 1-oxide | | 100 |
| | 4-ethynylpyridine 1-oxide | | 18 |
| | 4-ethynylpiperidine hydrochloride | | 0 |
| | 1-(4-ethynyl-1-piperidinyl)ethanone | | 0 |
| Pyrimidines | 2-ethynylpyrimidine | 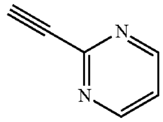 | 94 |
| | 5-ethynyl-1-methyl-1H-imidazole | | 100 |
| | 2,5-diethynylpyrimidine | | 60 |
| | 5-ethynylpyrimidine | | 95 |
| | 5-ethynyl-2-methoxypyrimidine | | 100 |

TABLE 1-continued

| FAMILY | IUPAC name | Structure | Inhib(%) |
|---|---|---|---|
| | 4-ethynylpyrimidine | | 100 |
| | 5-ethynyl-2,4(1H,3H)-pyrimidinedione | | 0 |

Testing 2-Ethynyl 1,3 Diazine

Study 1-1

Laboratory incubation studies were conducted to determine the efficacy of 2-Ethynyl 1,3 Diazine in inhibiting nitrification in the soil. A Templeton sandy loam was used in this experiment. 500 g of soil (dry weight basis) was packed into a pottle. 50 mL of synthetic cow urine with an N concentration of 7 g N/L (comprising about 87% urea-N and 13% glycine-N) was applied to the soil (equivalent to 700 kg N/ha on weight basis, assuming bulk density of 1 g/cm$^3$ in the top 10 cm of soil). The 700 kg N/ha application was used to simulate the urine-N application rate under a typical dairy cow urine patch in a grazed pasture. 5 mg of DCD dissolved in 0.9 mL of DMSO to give a concentration of 10 kg/ha; and 1 mg of 2-Ethynyl 1,3 Diazine dissolved in 0.9 mL DMSO to give a concentration of 2 kg/ha; were added to the urine-applied soil.

Control treatments also added to soil were:
urine alone (50 mL);
DMSO (equivalent to 0.9 mL/500 g soil)+urine (50 mL) to determine the effect of DMSO on nitrification rate;
water alone (50 mL) (simulating areas of the soil where no urine was deposited).

The urine, water, DMSO, DCD and 2-Ethynyl 1,3 Diazine treatments were applied to the surface of the soil and the soil was thoroughly mixed. Pottles were covered with lids with breathing holes to allow for gas exchange during incubation. Pottles were incubated at 12° C. Soil moisture content was maintained at field capacity by adjusting on weight basis twice a week.

Soil samples were collected and were then thoroughly mixed and subsamples were extracted in a potassium chloride solution and analysed for mineral-N. Soil moisture content was also determined. Samples were taken at 30 days after the start of incubation.

FIG. 1(B) shows the nitrate-N concentration in the soil at day 30 of incubation, showing significantly lower nitrate-N concentrations in the urine+(2-Ethynyl 1,3 Diazine dissolved in DMSO) treatment, demonstrating the ability of 2-Ethynyl 1,3 Diazine to inhibit nitrification in the soil at 2 kg/ha. These results show that when 2-Ethynyl 1,3 Diazine is applied to treat urine patches in soil at 2 kg/ha, significant reductions in nitrification rate can be achieved. In particular, 2-Ethynyl 1,3 Diazine at a concentration of only 2 kg/ha was more effective than DCD at a higher concentration of 10 kg/ha at reducing the nitrification rate.

Study 2-1

A second laboratory incubation study was conducted to determine the efficacy of 2-Ethynyl 1,3 Diazine in nitrification inhibition when applied at a lower rate of 1 kg/ha. The experimental procedures are the same as described in Study 1 except that 2-Ethynyl 1,3 Diazine was applied at 1 kg/ha.

FIG. 1(C) shows the nitrate-N concentration in the soil at the end of 30 days of incubation, as affected by the application of 2-Ethynyl 1,3 Diazine at 1 kg/ha to soil, illustrating the highly efficient inhibition of nitrification by 2-Ethynyl 1,3 Diazine, as shown by the lower nitrate-N concentrations in the urine+2-Ethynyl 1,3 Diazine treated soil compared with the urine alone or urine+DMSO control treatments.

Study 3-1

A third laboratory incubation study was conducted to determine the efficacy of 2-Ethynyl 1,3 Diazine in nitrification inhibition when applied at a lower rate of 0.5 kg/ha to soil. The experimental procedures are the same as described in Study 1 except that 2-Ethynyl 1,3 Diazine was applied at 0.5 kg/ha.

FIG. 1(D) shows the nitrate-N concentration in the soil at the end of 30 days of incubation, as affected by the application of 2-Ethynyl 1,3 Diazine at 0.5 kg/ha, illustrating the highly efficient inhibition of nitrification by 2-Ethynyl 1,3 Diazine at this very low application rate, as shown by the lower nitrate-N concentrations in the urine+2-Ethynyl 1,3 Diazine treated soil compared with the urine alone or urine+DMSO control treatments.

Study 4-1

To determine the effect of treating the soil with 2-Ethynyl 1,3 Diazine on nitrous oxide emissions under field soil conditions, a field study was conducted using the static gas chamber method. This study was conducted on the Lincoln University Research Dairy Farm, and the soil was a Templeton sandy loam with established perennial ryegrass (*Lolium perenne*) and white clover (*Trifolium repens.*) pasture. Metal rings (500 mm diameter and 200 mm height) were inserted into the ground. A water trough sitting on top of the metal rings allowed the placement of static chambers sitting on top of the water trough to provide a gas-tight seal to allow $N_2O$ gas sampling.

Synthetic urine with a nitrogen concentration of 7 g N/L was applied to the soil plots confined within the metal rings at the equivalent rate of 700 kg N/ha. 196.25 mg or 39.2 mg of 2-Ethynyl 1,3 Diazine were dissolved in 2 mL DMSO, mixed with 1000 mL of water, and then sprayed on to the mini-plots at the rates of 196.25 mg/plot and 39.2 mg/plot, equivalent to 10 kg/ha and 2 kg/ha, respectively. The plots were irrigated with irrigation water in accordance with local dairy farming practice.

The gas chamber (500 mm diameter and 120 mm height) was constructed of a metal cylinder insulated with 2.5 cm thick polystyrene foam to avoid heating of the atmosphere in the chamber during sampling. During periods of $N_2O$ measurement, the edge of the chamber was placed inside the small water trough which was mounted around the top of each metal ring for gas sampling. At each sampling time, the chamber was placed on top of the soil ring for a total of 40 minutes, and 3 samples, 20 minutes apart, were taken using a syringe through a rubber septum on top of the gas chamber. Samples were taken twice weekly. Each sampling was carried out during the middle of the day between 12:00 h to 14:00 h (Di et al., 2007). The $N_2O$ concentration in the samples was analysed using a gas chromatograph (SRI8610C with an Electron Capture Detector (ECD) (SRI Instruments, USA) linked to a Gilson 222XL autosampler (Gilson, France)

FIG. 1(E) shows the effectiveness of 2-Ethynyl 1,3 Diazine in reducing $N_2O$—N emissions when 2-Ethynyl 1,3 Diazine was sprayed onto soil surface with pasture in the field which had received animal urine. $N_2O$—N emissions in the urine+2-Ethynyl 1,3 Diazine treated soil were about 96% and 91% lower than that in the urine alone control treatment when 2-Ethynyl 1,3 Diazine was applied at 10 kg/ha and 2 kg/ha, respectively. This shows the efficiency of 2-Ethynyl 1,3 Diazine in reducing $N_2O$ emissions in the soil. The nitrous oxide reductions by 2-Ethynyl 1,3 Diazine were greater than that by DCD.

Figure 2:
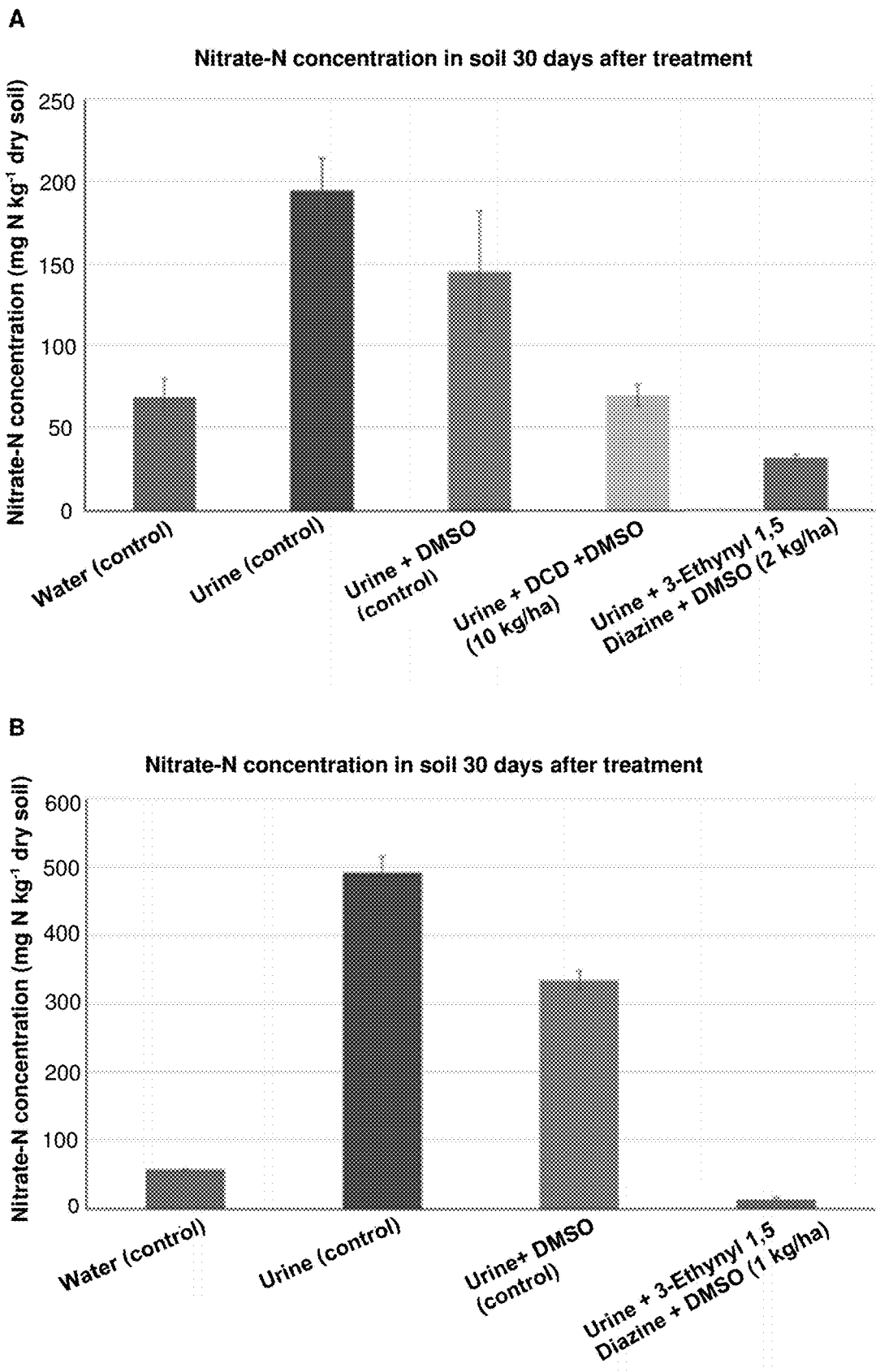
FIG. 2. (A) shows the nitrate-N concentration in the soil at the end of 30 days of incubation, as affected by the application of 3-Ethynyl 1,5 Diazine at 2 kg/ha, illustrating the highly efficient inhibition of nitrification by 3-Ethynyl 1,5 Diazine, as shown by the lower nitrate-N concentrations in the urine+3-Ethynyl 1,5 Diazine treated soil compared with the urine alone or urine+DMSO control treatments. The error bars represent one standard error of the mean (SEM). (B) shows the nitrate-N concentration in the soil at the end of 30 days of incubation, as affected by the application of 3-Ethynyl 1,5 Diazine at 1 kg/ha, illustrating the highly efficient inhibition of nitrification by 3-Ethynyl 1,5 Diazine, as shown by the lower nitrate-N concentrations in the urine+3-Ethynyl 1,5 Diazine treated soil compared with the urine alone or urine+DMSO control treatments. The error bars represent one standard error of the mean (SEM). (C) shows the nitrate-N concentration in the soil at the end of 30 days of incubation, as affected by the application of 3-Ethynyl 1,5 Diazine at 0.5 kg/ha, illustrating the highly efficient inhibition of nitrification by 3-Ethynyl 1,5 Diazine, as shown by the lower nitrate-N concentrations in the urine+3-Ethynyl 1,5 Diazine treated soil compared with the urine alone or urine+DMSO control treatments. The error bars represent one standard error of the mean (SEM). (D) shows the effectiveness of 3-Ethynyl 1,5 Diazine in reducing $N_2O$—N emissions when 3-Ethynyl 1,5 Diazine was sprayed to soil surface with pasture in the field which had received animal urine. $N_2O$—N emissions in the urine+3-Ethynyl 1,5 Diazine treated soil were about 93% lower than that in the urine alone control treatment when 3-Ethynyl 1,5 Diazine was applied at 10 kg/ha or 2 kg/ha. This shows the efficiency of 3-Ethynyl 1,5 Diazine in reducing $N_2O$ emissions in the soil. The nitrous oxide reductions by 3-Ethynyl 1,5 Diazine were greater than that by DCD. The error bars in the figure represent one standard error of the mean (SEM).
Figure 2:
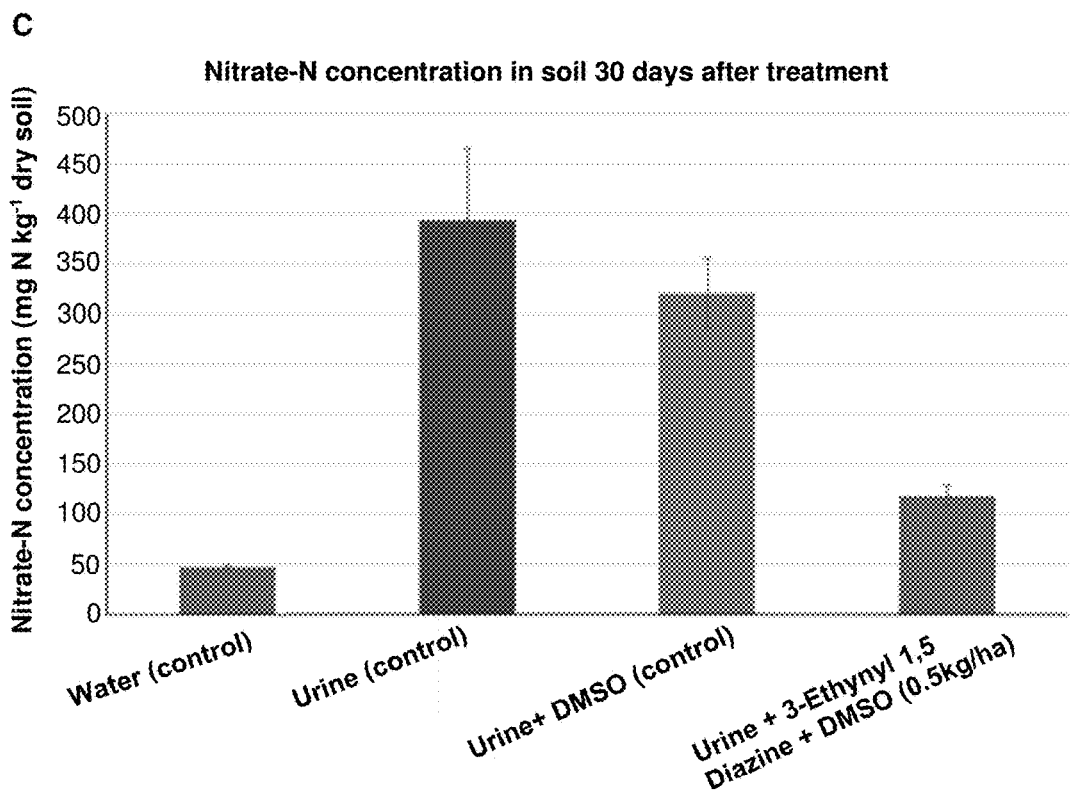
Figure 2:
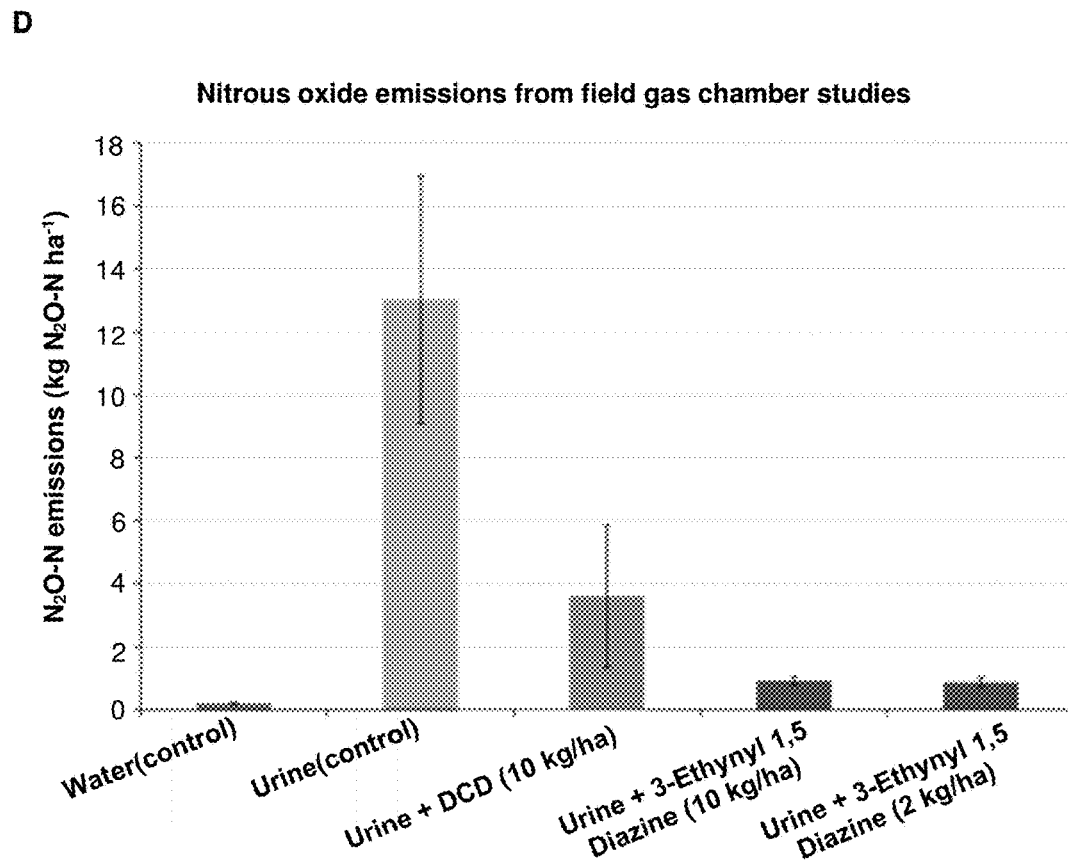

The effect of 2-Ethynyl 1,3 Diazine on nitrate concentrations and nitrous oxide emissions in Studies 1-4 are shown in Table 1-1 below:

FIG. 2(B) shows the nitrate-N concentration in the soil at the end of 30 days of incubation, as affected by the application of 3-Ethynyl 1,5 Diazine at 1 kg/ha to soil, illustrating the highly efficient inhibition of nitrification by 3-Ethynyl 1,5 Diazine, as shown by the lower nitrate-N concentrations in the urine+3-Ethynyl 1,5 Diazine treated soil compared with the urine alone or urine+DMSO control treatments.

Study 3-2

A third laboratory incubation study was conducted to determine the efficacy of 3-Ethynyl 1,5 Diazine in nitrification inhibition when applied at a lower rate of 0.5 kg/ha to soil. The experimental procedures are the same as described in Study 1-1.

FIG. 2(C) shows the nitrate-N concentration in the soil at the end of 30 days of incubation, as affected by the application of 3-Ethynyl 1,5 Diazine at 0.5 kg/ha, illustrating the highly efficient inhibition of nitrification by 3-Ethynyl 1,5 Diazine at this very low application rate, as shown by the lower nitrate-N concentrations in the urine+3-Ethynyl 1,5 Diazine treated soil compared with the urine alone or urine+DMSO control treatments.

Study 4-2

To determine the effect of treating the soil with 3-Ethynyl 1,5 Diazine on nitrous oxide emissions under field soil conditions, a field study was conducted using the static gas chamber method. This study was conducted on the Lincoln University Research Dairy Farm, and the soil was a Templeton sandy loam with established perennial ryegrass (*Lolium perenne*) and white clover (*Trifolium repens.*) pasture. Metal

TABLE 1-1

NIC 93

Effect of new nitrification inhibitors (NI) on nitrate concentration or nitrous oxide emissions % reduction by NI

| Study 1 | | Urine | Urine + 2-Ethynyl 1,3 Diazine (2 kg/ha) | |
|---|---|---|---|---|
| | Nitrate-N (mg N/kg soil) | 194.7 | 31.8 | 84% |
| Study 2 | | Urine | Urine + 2-Ethynyl 1,3 Diazine (1 kg/ha) | |
| | Nitrate-N (mg N/kg soil) | 491.8 | 9.1 | 98% |
| Study 3 | | Urine | Urine + 2-Ethynyl 1,3 Diazine (0.5 kg/ha) | |
| | Nitrate-N (mg N/kg soil) | 393.9 | 17.5 | 96% |
| Study 4 | | Urine | Urine + 2-Ethynyl 1,3 Diazine (10 kg/ha) | |
| | N2O emissions (kg N2O—N/ha) | 13.0 | 0.53 | 96% |
| | | Urine | Urine + 2-Ethynyl 1,3 Diazine (2 kg/ha) | |
| | N2O emissions (kg N2O—N/ha) | 13.0 | 1.2 | 91% |

Testing 3-Ethynyl 1,5 Diazine

Study 1-2

A laboratory incubation study was conducted to determine the efficacy of 3-Ethynyl 1,5 Diazine in nitrification inhibition when applied at a rate of 2 kg/ha. The experimental procedures are the same as described in Study 1-1.

FIG. 2(A) shows the nitrate-N concentration in the soil at day 30 of incubation, showing significantly lower nitrate-N concentrations in the urine+(3-Ethynyl 1,5 Diazine dissolved in DMSO) treatment, demonstrating the ability of 3-Ethynyl 1,5 Diazine to inhibit nitrification in the soil at 2 kg/ha. These results show that when 3-Ethynyl 1,5 Diazine is applied to treat urine patches in soil at 2 kg/ha, significant reductions in nitrification rate can be achieved. In particular, 3-Ethynyl 1,5 Diazine at a concentration of only 2 kg/ha was more effective than DCD at a higher concentration of 10 kg/ha at reducing the nitrification rate.

Study 2-2

A second laboratory incubation study was conducted to determine the efficacy of 3-Ethynyl 1,5 Diazine in nitrification inhibition when applied at a lower rate of 1 kg/ha. The experimental procedures are the same as described in Study 1-1.

rings (500 mm diameter and 200 mm height) were inserted into the ground. A water trough sitting on top of the metal rings allowed the placement of static chambers sitting on top of the water trough to provide a gas-tight seal to allow $N_2O$ gas sampling.

Synthetic urine with a nitrogen concentration of 7 g N/L was applied to the soil plots confined within the metal rings at the equivalent rate of 700 kg N/ha. 196.25 mg or 39.2 mg of 3-Ethynyl 1,5 Diazine were dissolved in 2 mL DMSO, mixed with 1000 mL of water, and then sprayed on to the mini-plots at the rates of 196.25 mg/plot and 39.2 mg/plot, equivalent to 10 kg/ha and 2 kg/ha, respectively. The plots were irrigated with irrigation water in accordance with local dairy farming practice.

The gas chamber (500 mm diameter and 120 mm height) was constructed of a metal cylinder insulated with 2.5 cm thick polystyrene foam to avoid heating of the atmosphere in the chamber during sampling. During periods of $N_2O$ measurement, the edge of the chamber was placed inside the small water trough which was mounted around the top of each metal ring for gas sampling. At each sampling time, the chamber was placed on top of the soil ring for a total of 40 minutes, and 3 samples, 20 minutes apart, were taken using a syringe through a rubber septum on top of the gas chamber. Samples were taken twice weekly. Each sampling was carried out during the middle of the day between 12:00 h to 14:00 h (Di et al., 2007). The $N_2O$ concentration in the samples was analysed using a gas chromatograph (SRI8610C with an Electron Capture Detector (ECD) (SRI Instruments, USA) linked to a Gilson 222XL autosampler (Gilson, France)

FIG. 2(D) shows the effectiveness of 3-Ethynyl 1,5 Diazine in reducing $N_2O$—N emissions when 3-Ethynyl 1,5 Diazine was sprayed onto soil surface with pasture in the field which had received animal urine. $N_2O$—N emissions in the urine+3-Ethynyl 1,5 Diazine treated soil were about 96% and 91% lower than that in the urine alone control treatment when 3-Ethynyl 1,5 Diazine was applied at 10 kg/ha and 2 kg/ha, respectively. This shows the efficiency of 3-Ethynyl 1,5 Diazine in reducing $N_2O$ emissions in the soil. The nitrous oxide reductions by 3-Ethynyl 1,5 Diazine were greater than that by DCD.

The effect of 3-Ethynyl 1,5 Diazine on nitrate concentrations and nitrous oxide emissions in Studies 1-4 are shown in Table 1-2 below:

TABLE 1-2

Effect of new nitrification inhibitors (NI) on nitrate concentration or nitrous oxide emissions % reduction by NI

| Study 1 | | Urine | Urine + 3-Ethynyl 1,5 Diazine (2 kg/ha) | |
|---|---|---|---|---|
| | Nitrate-N (mg N/kg soil) | 194.7 | 31.6 | 84% |
| Study 2 | | Urine | Urine + 3-Ethynyl 1,5 Diazine (1 kg/ha) | |
| | Nitrate-N (mg N/kg soil) | 491.8 | 13.3 | 97% |
| Study 3 | | Urine | Urine + 3-Ethynyl 1,5 Diazine (0.5 kg/ha) | |
| | Nitrate-N (mg N/kg soil) | 393.9 | 118.1 | 70% |
| Study 4 | | Urine | Urine + 3-Ethynyl 1,5 Diazine (10 kg/ha) | |
| | N2O emissions (kg N2O—N/ha) | 13.0 | 0.92 | 93% |
| | | Urine | Urine + 3-Ethynyl 1,5 Diazine (2 kg/ha) | |
| | N2O emissions (kg N2O—N/ha) | 13.0 | 0.89 | 93% |

Testing 4-Ethynylpyrimidine
Study 1-3
A laboratory incubation study was conducted to determine the efficacy of 4-Ethynylpyrimidine in nitrification inhibition when applied at a rate of 2 kg/ha. The experimental procedures are the same as described in Study 1-1.

Figure 3:
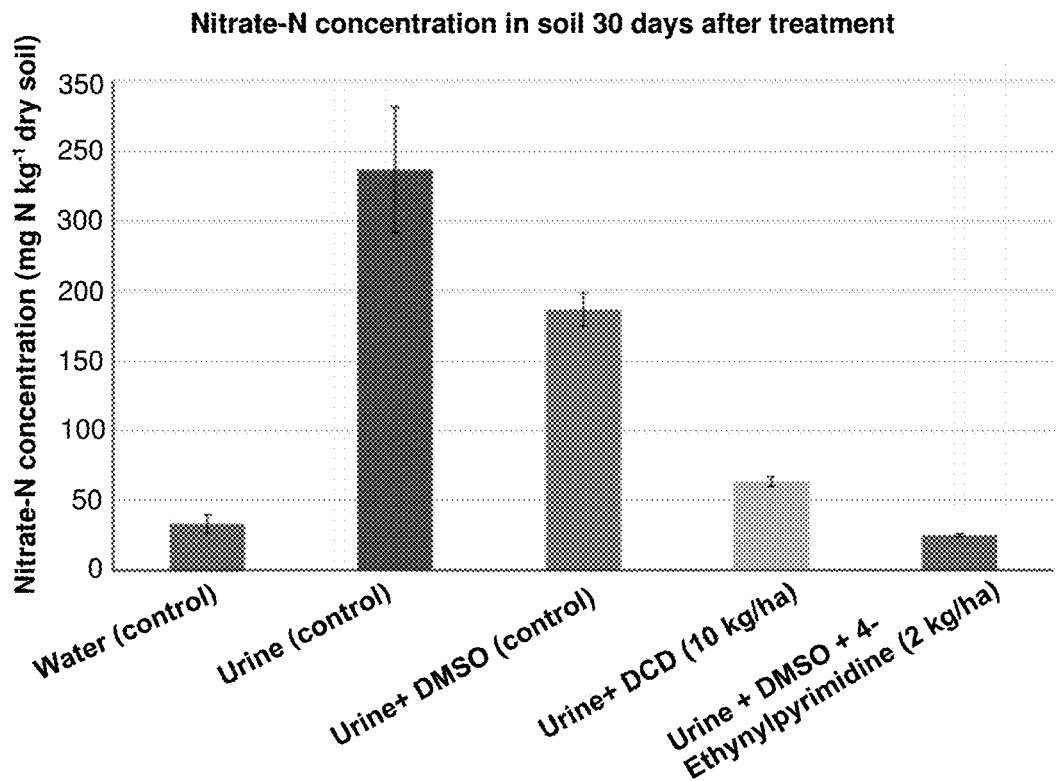
FIG. 3. (A) shows the nitrate-N concentration in the soil at the end of 30 days of incubation, as affected by the application of 4-Ethynylpyrimidine at 2 kg/ha, illustrating the highly efficient inhibition of nitrification by 4-Ethynylpyrimidine, as shown by the lower nitrate-N concentrations in the urine+4-Ethynylpyrimidine treated soil compared with the urine alone or urine+dimethyl sulfoxide (DMSO) control treatments. The error bars represent one standard error of the mean (SEM). (B) shows the nitrate-N concentration in the soil at the end of 30 days of incubation, as affected by the application of 4-Ethynylpyrimidine at 1 kg/ha, illustrating the highly efficient inhibition of nitrification by 4-Ethynylpyrimidine as shown by the lower nitrate-N concentrations in the urine+4-Ethynylpyrimidine treated soil compared with the urine alone or urine+DMSO control treatments. The error bars represent one standard error of the mean (SEM).
Figure 3:
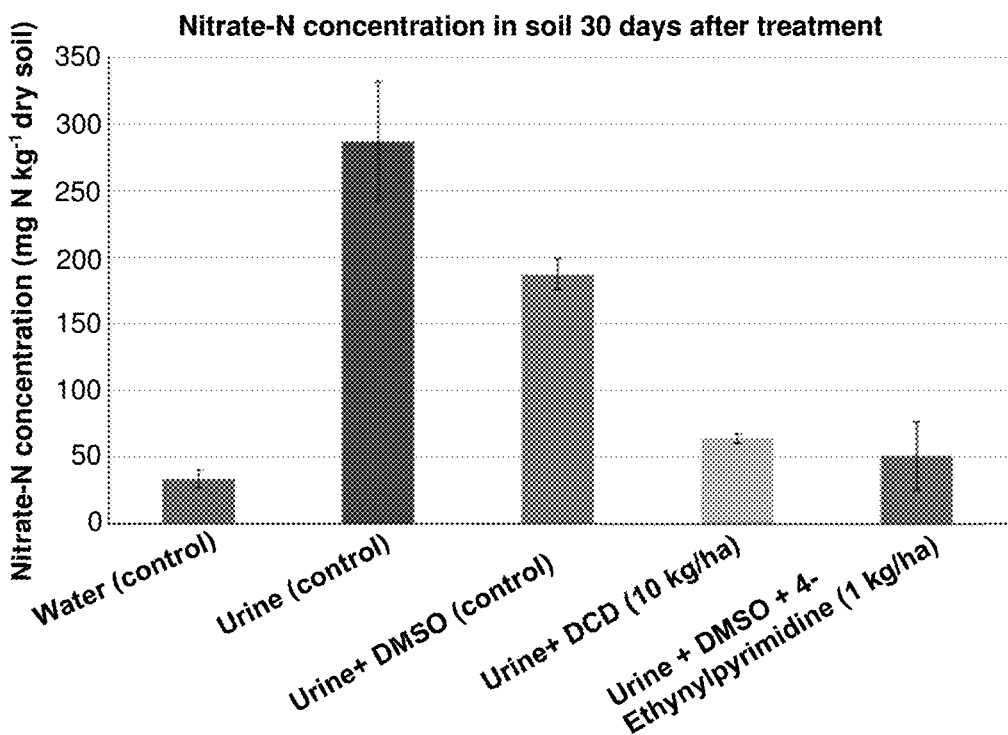

FIG. 3(A) shows the nitrate-N concentration in the soil at day 30 of incubation, showing significantly lower nitrate-N concentrations in the urine+(4-Ethynylpyrimidine dissolved in DMSO) treatment, demonstrating the ability of 4-Ethynylpyrimidine to inhibit nitrification in the soil at 2 kg/ha. These results show that when 4-Ethynylpyrimidine is applied to treat urine patches in soil at 2 kg/ha, significant reductions in nitrification rate can be achieved. In particular, 4-Ethynylpyrimidine at a concentration of only 2 kg/ha was more effective than DCD at a higher concentration of 10 kg/ha at reducing the nitrification rate.

Study 2-3
A second laboratory incubation study was conducted to determine the efficacy of 4-Ethynylpyrimidine in nitrification inhibition when applied at a lower rate of 1 kg/ha. The experimental procedures are the same as described in Study 1-1.

FIG. 3(B) shows the nitrate-N concentration in the soil at the end of 30 days of incubation, as affected by the application of 4-Ethynylpyrimidine at 1 kg/ha to soil, illustrating the highly efficient inhibition of nitrification by 4-Ethynylpyrimidine, as shown by the lower nitrate-N concentrations in the urine+4-Ethynylpyrimidine treated soil compared with the urine alone or urine+DMSO control treatments.

Testing 2-Ethynyl-5-methoxypyrimidine
Study 1-4
A laboratory incubation study was conducted to determine the efficacy of 2-Ethynyl-5-methoxypyrimidine in nitrification inhibition when applied at a rate of 2 kg/ha. The experimental procedures are the same as described in Study 1-1.

Figure 4:
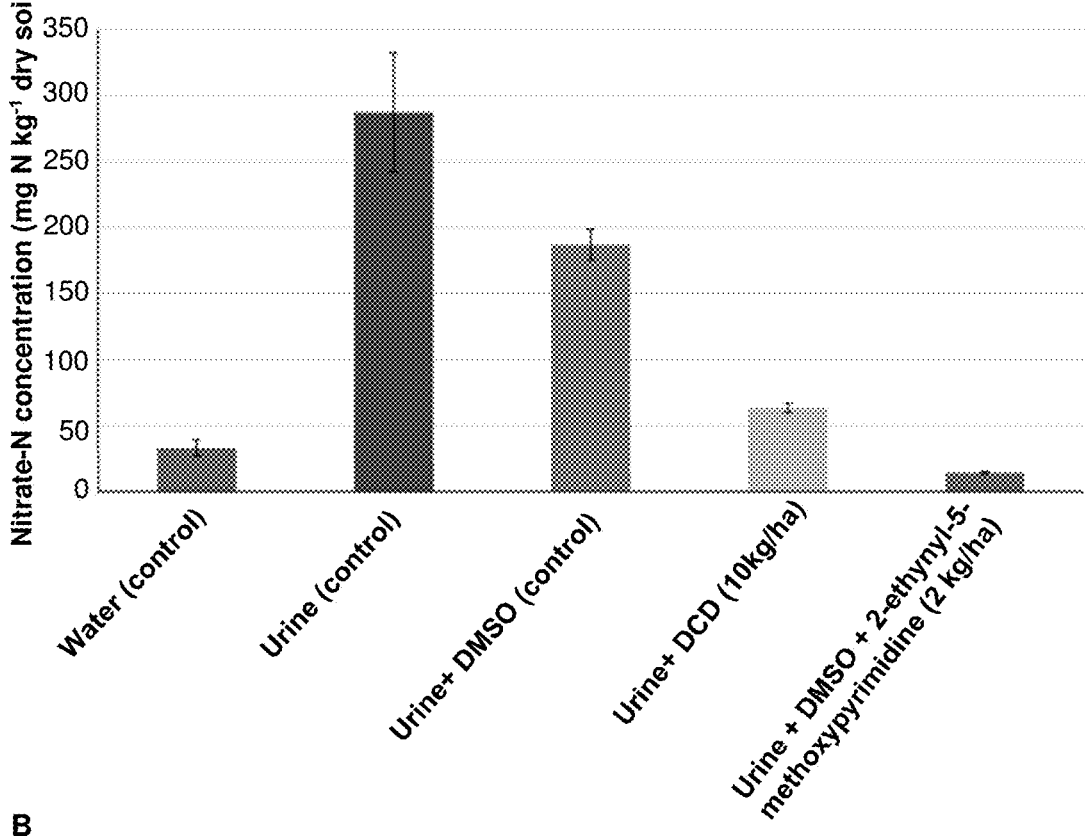
FIG. 4. (A) shows the nitrate-N concentration in the soil at the end of 30 days of incubation, as affected by the application of 2-Ethynyl-5-methoxypyrimidine at 2 kg/ha, illustrating the highly efficient inhibition of nitrification by 2-Ethynyl-5-methoxypyrimidine, as shown by the lower nitrate-N concentrations in the urine+2-Ethynyl-5-methoxypyrimidine treated soil compared with the urine alone or urine+dimethyl sulfoxide (DMSO) control treatments. The error bars represent one standard error of the mean (SEM). (B) shows the nitrate-N concentration in the soil at the end of 30 days of incubation, as affected by the application of 2-Ethynyl-5-methoxypyrimidine at 1 kg/ha, illustrating the highly efficient inhibition of nitrification by 2-Ethynyl-5-methoxypyrimidine as shown by the lower nitrate-N concentrations in the urine+2-Ethynyl-5-methoxypyrimidine treated soil compared with the urine alone or urine+DMSO control treatments. The error bars represent one standard error of the mean (SEM).
Figure 4:
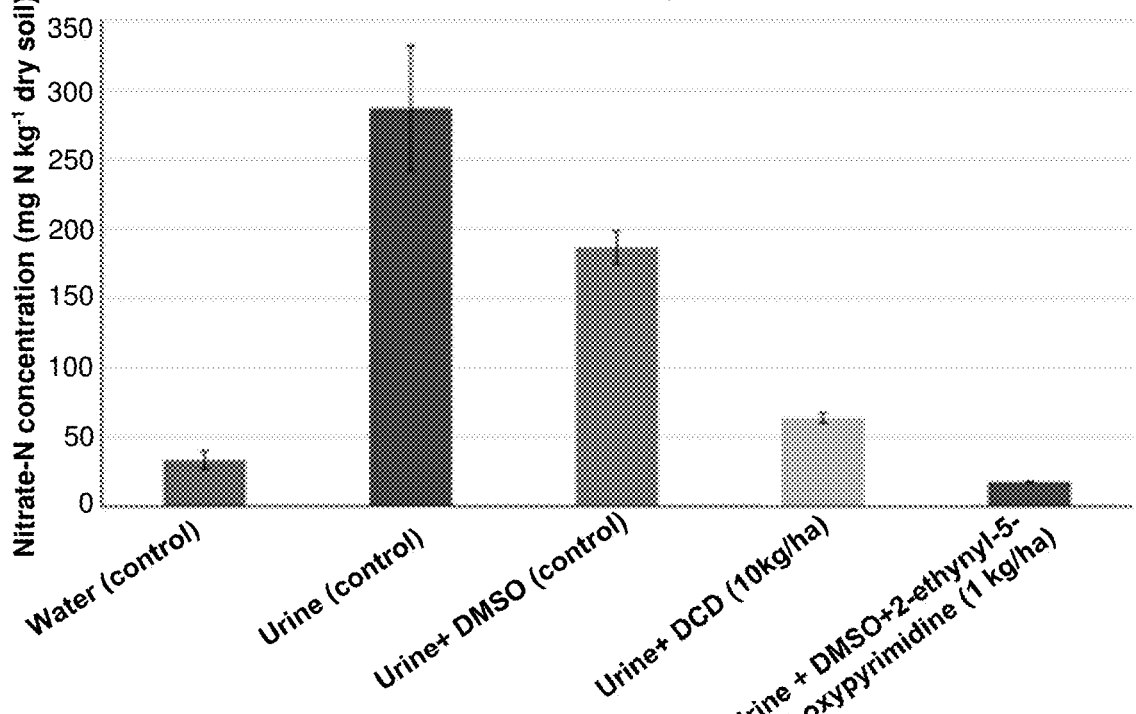

FIG. 4(A) shows the nitrate-N concentration in the soil at day 30 of incubation, showing significantly lower nitrate-N concentrations in the urine+(2-Ethynyl-5-methoxypyrimidine dissolved in DMSO) treatment, demonstrating the ability of 2-Ethynyl-5-methoxypyrimidine to inhibit nitrification in the soil at 2 kg/ha. These results show that when 2-Ethynyl-5-methoxypyrimidine is applied to treat urine patches in soil at 2 kg/ha, significant reductions in nitrification rate can be achieved. In particular, 2-Ethynyl-5-methoxypyrimidine at a concentration of only 2 kg/ha was more effective than DCD at a higher concentration of 10 kg/ha at reducing the nitrification rate.

Study 2-4
A second laboratory incubation study was conducted to determine the efficacy of 2-Ethynyl-5-methoxypyrimidine in nitrification inhibition when applied at a lower rate of 1 kg/ha. The experimental procedures are the same as described in Study 1-1.

FIG. 4(B) shows the nitrate-N concentration in the soil at the end of 30 days of incubation, as affected by the application of 2-Ethynyl-5-methoxypyrimidine at 1 kg/ha to soil, illustrating the highly efficient inhibition of nitrification by 2-Ethynyl-5-methoxypyrimidine, as shown by the lower nitrate-N concentrations in the urine+2-Ethynyl-5-methoxypyrimidine treated soil compared with the urine alone or urine+DMSO control treatments.

Route Towards 2-Ethynyl-5-methoxypyrimidine

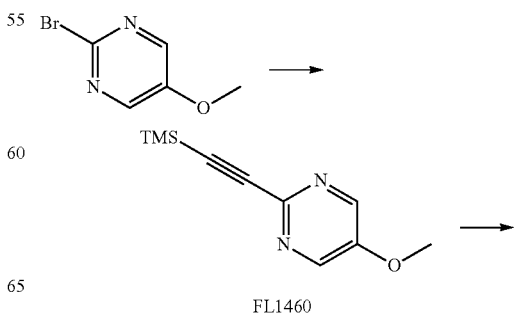

FL1460

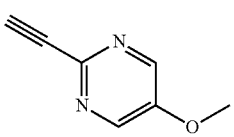

HDDR326/FL1462

A suspension of 2-bromo-5-methoxypyrimidine (1.57 g, 8.3 mmol, 1.0 eqv.), ethynyltrimethylsilane (1.8 mL, 12.5 mmol, 1.5 eqv.), triethylamine (5.8 mL, 41.5 mmol, 5.0 eqv.), bis(triphenylphosphine)palladium(II) dichloride (292 mg, 0.42 mmol, 0.05 eqv.) and copper(I) iodide (158 mg, 0.84 mmol, 0.1 eqv.) in degassed anhydrous tetrahydrofuran (30 mL) was heated at reflux under argon for 15 h.

The mixture was cooled to room temperature, filtered through Celite® and the filtrate was concentrated in vacuo. Purification by column chromatography (petroleum ether/ethyl acetate 19:1) afforded 5-methoxy-2-((trimethylsilyl)ethynyl)pyrimidine (FL1460) as an off-white solid (1.68 g, 98%). 1H NMR (400 MHz, CDCl$_3$) δ 0.27 (9H, s), 3.92 (3H, s), 8.34 (2H, s); 13C NMR (100 MHz, CDCl$_3$) δ −0.3 (CH3), 56.2 (CH3), 92.4 (C), 102.2 (C), 143.6 (CH), 145.3 (C), 152.5 (C).

A mixture of 5-methoxy-2-((trimethylsilyl)ethynyl)pyrimidine (FL1460, 1.27 g, 6.2 mmol, 1.0 eqv.) and potassium hydroxide (345 mg, 6.2 mmol, 1.0 eqv.) in methanol-water (24 mL, 5:1 v/v) was stirred at room temperature for 10 min.

The mixture was then diluted with ethyl acetate (100 mL) and water (100 mL). The separated aqueous layer was further extracted with ethyl acetate (2×50 mL) and the combined organic extracts were washed with brine (100 mL), dried over anhydrous sodium sulfate, filtered and concentrated in vacuo.

Purification by column chromatography (petroleum ether/ethyl acetate 4:1) afforded 2-ethynyl-5-methoxypyrimidine (/HDDR326/FL1462) as an off-white solid (720 mg, 87%). mp 56.2-57.2° C.; 1H NMR (400 MHz, CDCl$_3$) δ 3.01 (1H, s), 3.90 (3H, s), 8.32 (2H, s); 13C NMR (100 MHz, CDCl$_3$) δ 56.2 (CH3), 74.3 (CH), 81.6 (C), 143.6 (CH), 144.6 (C), 152.8 (C); HRMS (ESI+): N/A.

Testing 5-Ethynyl-2-methoxypyrimidine
Study 1-5

A laboratory incubation study was conducted to determine the efficacy of 5-Ethynyl-2-methoxypyrimidine in nitrification inhibition when applied at a rate of 2 kg/ha. The experimental procedures are the same as described in Study 1-1.

Figure 5:
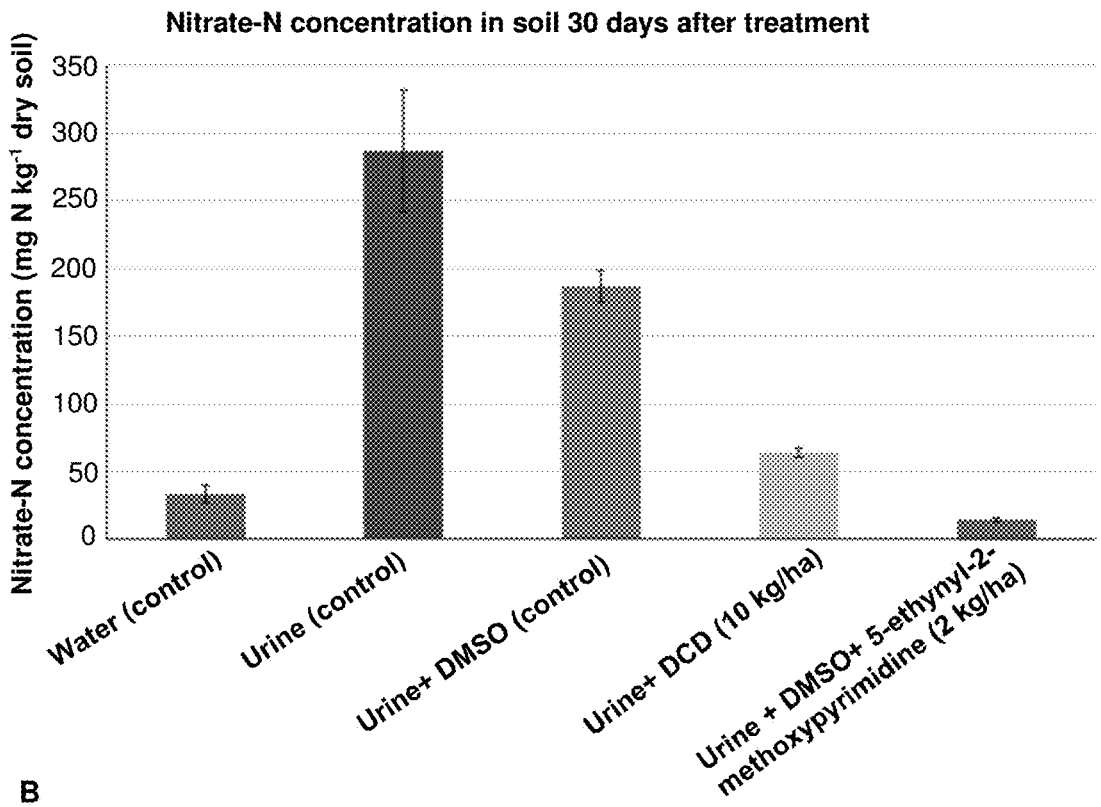
FIG. 5. (A) shows the nitrate-N concentration in the soil at the end of 30 days of incubation, as affected by the application of 5-Ethynyl-2-methoxypyrimidine at 2 kg/ha, illustrating the highly efficient inhibition of nitrification by 5-Ethynyl-2-methoxypyrimidine, as shown by the lower nitrate-N concentrations in the urine+5-Ethynyl-2-methoxypyrimidine treated soil compared with the urine alone or urine+dimethyl sulfoxide (DMSO) control treatments. The error bars represent one standard error of the mean (SEM). (B) shows the nitrate-N concentration in the soil at the end of 30 days of incubation, as affected by the application of 5-Ethynyl-2-methoxypyrimidine at 1 kg/ha, illustrating the highly efficient inhibition of nitrification by 5-Ethynyl-2-methoxypyrimidine, as shown by the lower nitrate-N concentrations in the urine+5-Ethynyl-2-methoxypyrimidine treated soil compared with the urine alone or urine+dimethyl sulfoxide (DMSO) control treatments. The error bars represent one standard error of the mean (SEM).
Figure 5:
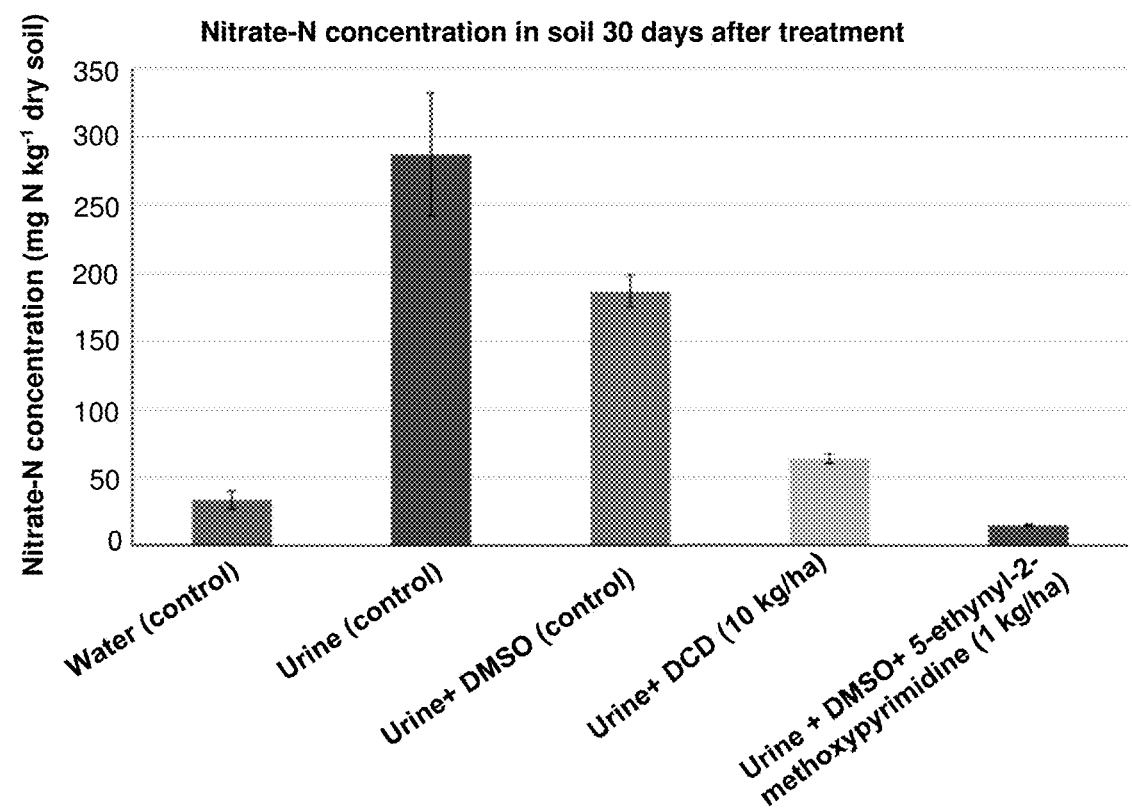

FIG. 5(A) shows the nitrate-N concentration in the soil at the end of 30 days of incubation, as affected by the application of 5-Ethynyl-2-methoxypyrimidine at 2 kg/ha to soil, illustrating the highly efficient inhibition of nitrification by 5-Ethynyl-2-methoxypyrimidine, as shown by the lower nitrate-N concentrations in the urine+5-Ethynyl-2-methoxypyrimidine treated soil compared with the urine alone or urine+DMSO control treatments.

Study 2-5

A second laboratory incubation study was conducted to determine the efficacy of 5-Ethynyl-2-methoxypyrimidine in nitrification inhibition when applied at a lower rate of 1 kg/ha. The experimental procedures are the same as described in Study 1-5.

FIG. 5(B) shows the nitrate-N concentration in the soil at the end of 30 days of incubation, as affected by the application of 5-Ethynyl-2-methoxypyrimidine at 1 kg/ha to soil, illustrating the highly efficient inhibition of nitrification by 5-Ethynyl-2-methoxypyrimidine, as shown by the lower nitrate-N concentrations in the urine+5-Ethynyl-2-methoxypyrimidine treated soil compared with the urine alone or urine+DMSO control treatments.

Route Towards 5-Ethynyl-2-methoxypyrimidine

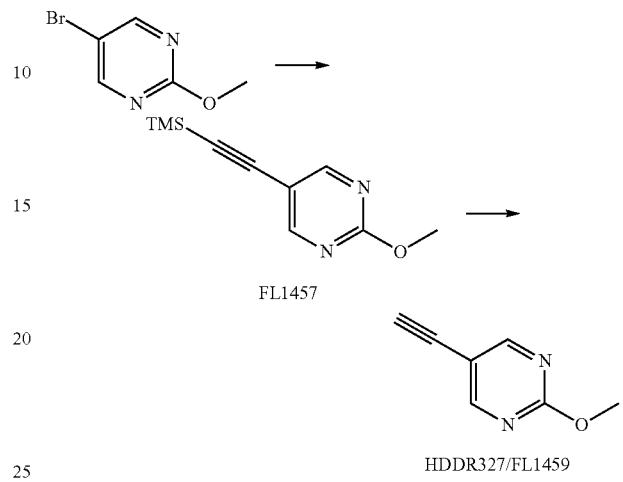

FL1457

HDDR327/FL1459

A suspension of 5-bromo-2-methoxypyrimidine (4.72 g, 23.7 mmol, 1.0 eqv.), ethynyltrimethylsilane (4.9 mL, 35.6 mmol, 1.5 eqv.), triethylamine (16.6 mL, 118.5 mmol, 5.0 eqv.), bis(triphenylphosphine)palladium(II) dichloride (832 mg, 1.2 mmol, 0.05 eqv.) and copper(I) iodide (451 mg, 2.4 mmol, 0.1 eqv.) in degassed anhydrous tetrahydrofuran (75 mL) was heated at reflux under argon for 15 h.

The mixture was cooled to room temperature, filtered through Celite® and the filtrate was concentrated in vacuo. Purification by column chromatography (petroleum ether/ethyl acetate 49:1) afforded 2-methoxy-5-((trimethylsilyl)ethynyl)pyrimidine (FL1457) as an off-white solid (3.97 g, 81%). $^1$H NMR (300 MHz, CDCl$_3$) δ 0.24 (9H, s), 4.01 (3H, s), 8.56 (2H, s); $^{13}$C NMR (75 MHz, CDCl$_3$) δ −0.1 (CH3), 55.3 (CH3), 98.1 (C), 100.1 (C), 113.0 (C), 161.9 (CH), 164.1 (C).

A mixture of 2-methoxy-5-((trimethylsilyl)ethynyl)pyrimidine (FL1457, 3.97 g, 23.5 mmol, 1.0 eqv.) and potassium hydroxide (1.08 g, 23.5 mmol, 1.0 eqv.) in methanol-water (96 mL, 5:1 v/v) was stirred at room temperature for 30 min.

Methanol was removed under reduced pressure and the crude mixture was diluted with ethyl acetate (200 mL) and water (200 mL).

The separated aqueous layer was further extracted with ethyl acetate (2×100 mL) and the combined organic extracts were washed with brine (200 mL), dried over anhydrous sodium sulfate, filtered and concentrated in vacuo.

Purification by column chromatography (petroleum ether/ethyl acetate 9:1) afforded 5-ethynyl-2-methoxypyrimidine (/HDDR327/FL1459) as a white solid (1.07 g, 34%). mp 82.3-83.1° C. (lit.$^3$ mp 82° C.); $^1$H NMR (400 MHz, CDCl$_3$) δ 3.26 (1H, s), 4.01 (3H, s), 8.59 (2H, s); $^{13}$C NMR (100 MHz, CDCl$_3$) δ 55.4 (CH3), 77.2 (C), 82.4 (CH), 111.9 (C), 162.1 (CH), 164.4 (C); HRMS (ESI+): N/A.

Testing 2-ethynyl-5-methoxypyridine 2-ethynyl-5-methoxypyridine is a commercially available compound which can be sourced from many suppliers who can be found online using (1196155-18-6) see for example on the World-Wide Web: sigmaaldrich.com/catalog/product/aldrich/cds023940?lang=en&region=NZ.

Study 1-6

A laboratory incubation study was conducted to determine the efficacy of 2-ethynyl-5-methoxypyridine in nitrification inhibition when applied at a rate of 2 kg/ha. The experimental procedures are the same as described in Study 1-1.

Figure 6:
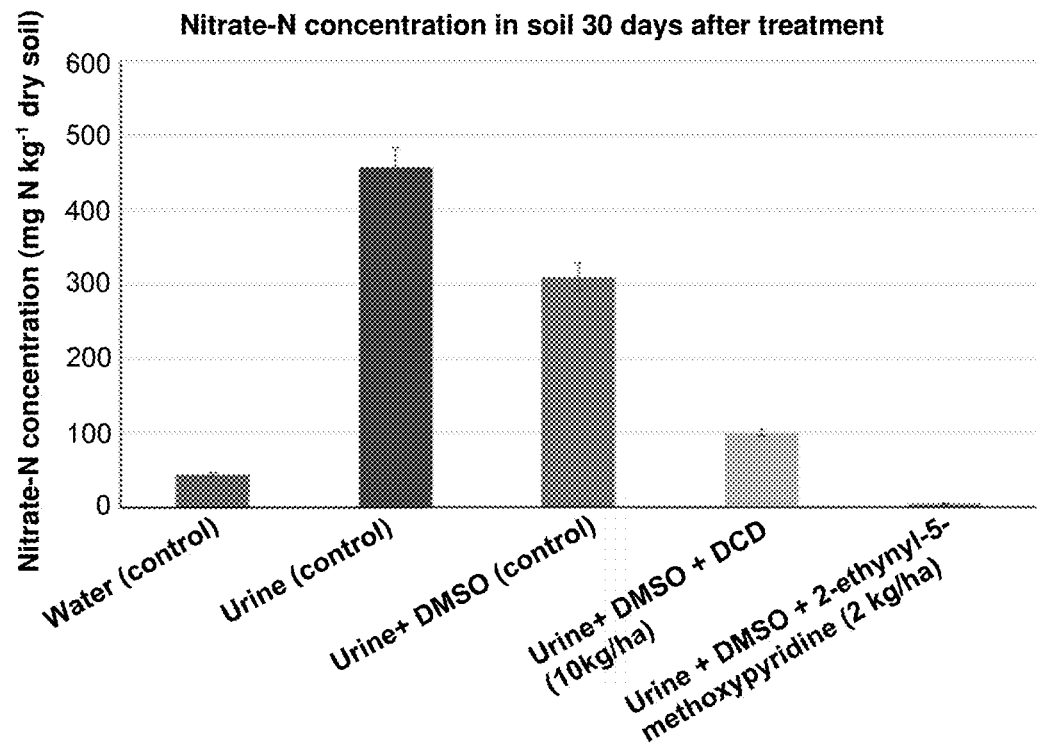
FIG. 6. (A) shows the nitrate-N concentration in the soil at the end of 30 days of incubation, as affected by the application of 2-ethynyl-5-methoxypyridine at 2 kg/ha, illustrating the highly efficient inhibition of nitrification by 2-ethynyl-5-methoxypyridine, as shown by the lower nitrate-N concentrations in the urine+2-ethynyl-5-methoxypyridine treated soil compared with the urine alone or urine+dimethyl sulfoxide (DMSO) control treatments. The error bars represent one standard error of the mean (SEM). (B) shows the nitrate-N concentration in the soil at the end of 30 days of incubation, as affected by the application of 2-ethynyl-5-methoxypyridine at 1 kg/ha, illustrating the highly efficient inhibition of nitrification by 2-ethynyl-5-methoxypyridine, as shown by the lower nitrate-N concentrations in the urine+2-ethynyl-5-methoxypyridine treated soil compared with the urine alone or urine+DMSO control treatments. The error bars represent one standard error of the mean (SEM). (C) shows the nitrate-N concentration in the soil at the end of 30 days of incubation, as affected by the application of 2-ethynyl-5-methoxypyridine at 0.5 kg/ha, illustrating the highly efficient inhibition of nitrification by 2-ethynyl-5-methoxypyridine, as shown by the lower nitrate-N concentrations in the urine+2-ethynyl-5-methoxypyridine treated soil compared with the urine alone or urine+DMSO control treatments. The error bars represent one standard error of the mean (SEM). (D) shows the effectiveness of 2-ethynyl-5-methoxypyridine in reducing $N_2O$—N emissions when 2-ethynyl-5-methoxypyridine was sprayed to soil surface with pasture in the field which had received animal urine. $N_2O$—N emissions in the urine+2-ethynyl-5-methoxypyridine treated soil were about 96% and 91% lower than that in the urine alone control treatment when 2-ethynyl-5-methoxypyridine was applied at 10 kg/ha and 2 kg/ha, respectively. This shows the efficiency of 2-ethynyl-5-methoxypyridine in reducing $N_2O$ emissions in the soil. The nitrous oxide reductions by 2-ethynyl-5-methoxypyridine were greater than that by DCD. The error bars in the figure represent one standard error of the mean (SEM).
Figure 6:
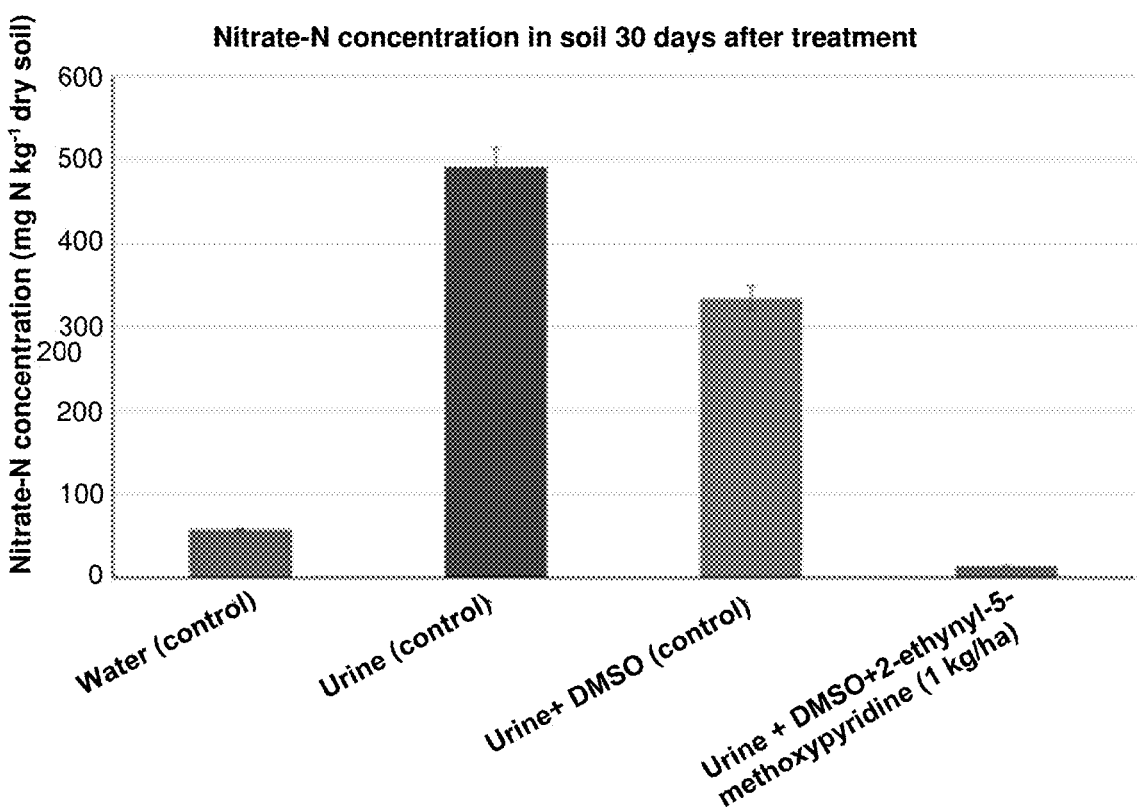
Figure 6:
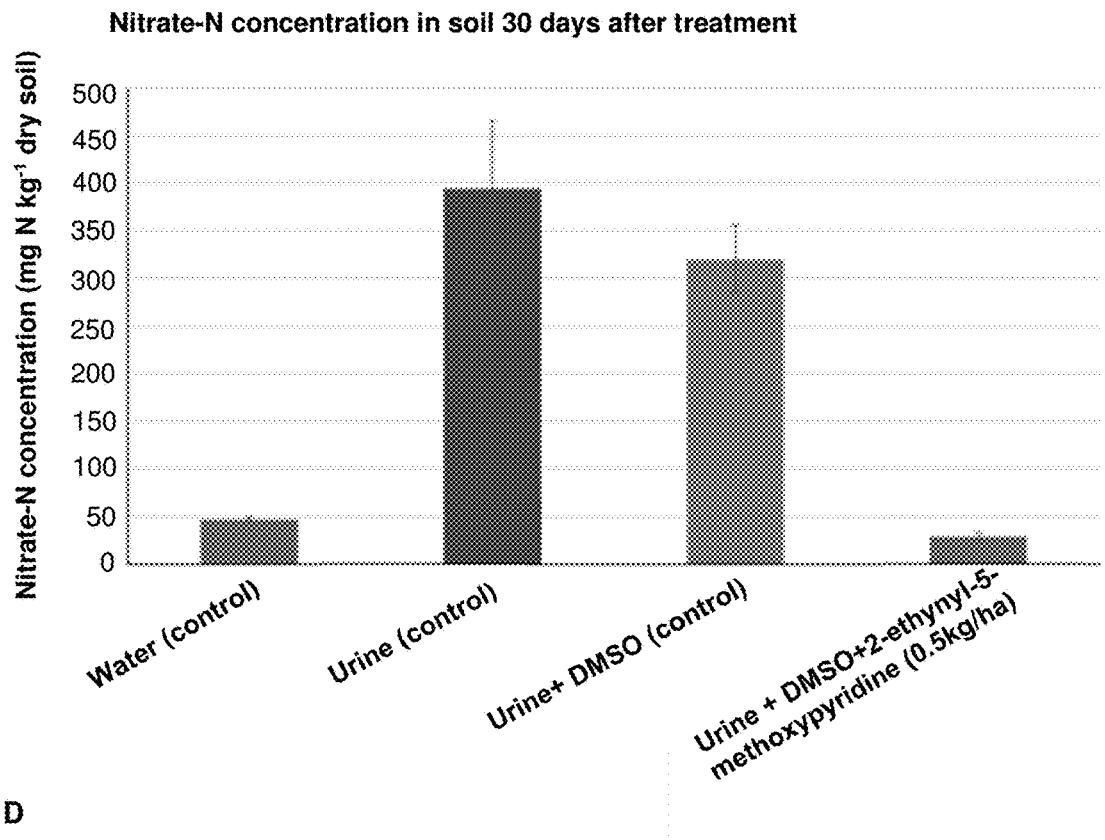
Figure 6:
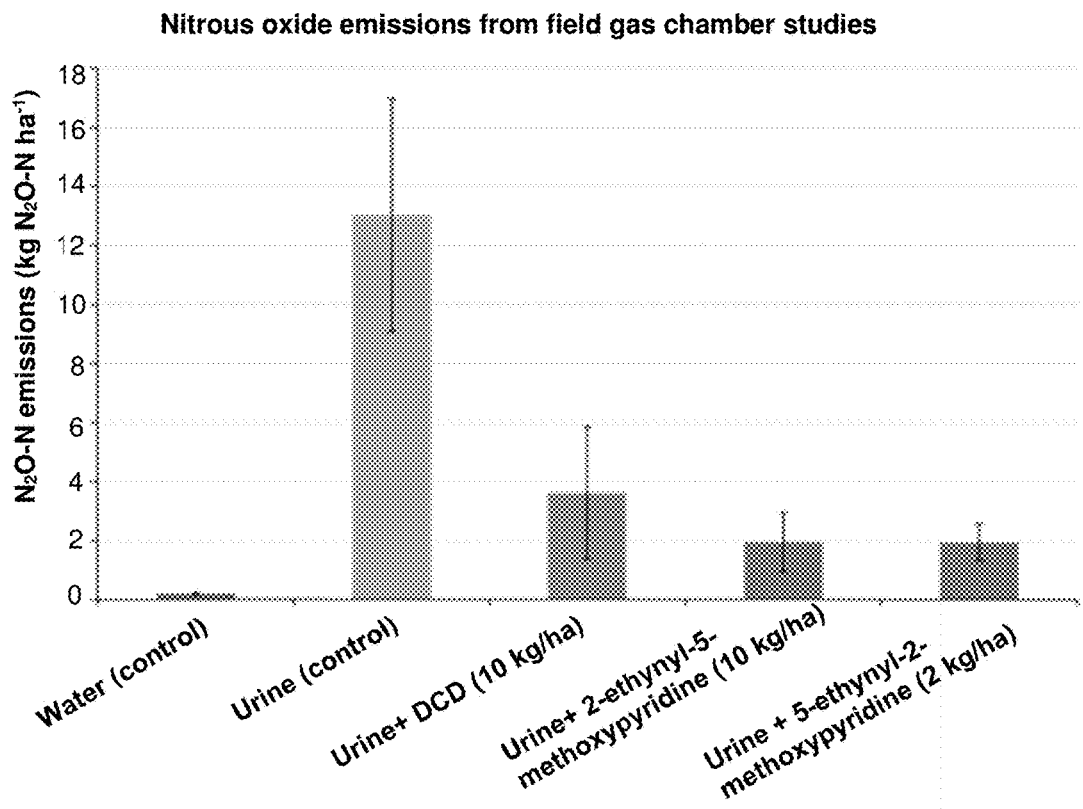

FIG. 6(A) shows the nitrate-N concentration in the soil at day 30 of incubation, showing significantly lower nitrate-N concentrations in the urine+(2-ethynyl-5-methoxypyridine dissolved in DMSO) treatment, demonstrating the ability of 2-ethynyl-5-methoxypyridine to inhibit nitrification in the soil at 2 kg/ha. These results show that when 2-ethynyl-5-methoxypyridine is applied to treat urine patches in soil at 2 kg/ha, significant reductions in nitrification rate can be achieved. In particular, 2-ethynyl-5-methoxypyridine at a concentration of only 2 kg/ha was more effective than DCD at a higher concentration of 10 kg/ha at reducing the nitrification rate.

Study 2-6

A second laboratory incubation study was conducted to determine the efficacy of 2-ethynyl-5-methoxypyridine in nitrification inhibition when applied at a lower rate of 1 kg/ha. The experimental procedures are the same as described in Study 1-1.

FIG. 6(B) shows the nitrate-N concentration in the soil at the end of 30 days of incubation, as affected by the application of 2-ethynyl-5-methoxypyridine at 1 kg/ha to soil, illustrating the highly efficient inhibition of nitrification by 2-ethynyl-5-methoxypyridine, as shown by the lower nitrate-N concentrations in the urine+2-ethynyl-5-methoxypyridine treated soil compared with the urine alone or urine+DMSO control treatments.

Study 3-6

A third laboratory incubation study was conducted to determine the efficacy of 2-ethynyl-5-methoxypyridine in nitrification inhibition when applied at a lower rate of 0.5 kg/ha to soil. The experimental procedures are the same as described in Study 1-1.

FIG. 6(C) shows the nitrate-N concentration in the soil at the end of 30 days of incubation, as affected by the application of 2-ethynyl-5-methoxypyridine at 0.5 kg/ha, illustrating the highly efficient inhibition of nitrification by 2-ethynyl-5-methoxypyridine at this very low application rate, as shown by the lower nitrate-N concentrations in the urine+2-ethynyl-5-methoxypyridine treated soil compared with the urine alone or urine+DMSO control treatments.

Study 4-6

To determine the effect of treating the soil with 2-ethynyl-5-methoxypyridine on nitrous oxide emissions under field soil conditions, a field study was conducted using the static gas chamber method. This study was conducted on the Lincoln University Research Dairy Farm, and the soil was a Templeton sandy loam with established perennial ryegrass (*Lolium perenne*) and white clover (*Trifolium repens.*) pasture. Metal rings (500 mm diameter and 200 mm height) were inserted into the ground. A water trough sitting on top of the metal rings allowed the placement of static chambers sitting on top of the water trough to provide a gas-tight seal to allow $N_2O$ gas sampling.

Synthetic urine with a nitrogen concentration of 7 g N/L was applied to the soil plots confined within the metal rings at the equivalent rate of 700 kg N/ha. 196.25 mg or 39.2 mg of 2-ethynyl-5-methoxypyridine were dissolved in 2 mL DMSO, mixed with 1000 mL of water, and then sprayed on to the mini-plots at the rates of 196.25 mg/plot and 39.2 mg/plot, equivalent to 10 kg/ha and 2 kg/ha, respectively. The plots were irrigated with irrigation water in accordance with local dairy farming practice.

The gas chamber (500 mm diameter and 120 mm height) was constructed of a metal cylinder insulated with 2.5 cm thick polystyrene foam to avoid heating of the atmosphere in the chamber during sampling. During periods of $N_2O$ measurement, the edge of the chamber was placed inside the small water trough which was mounted around the top of each metal ring for gas sampling. At each sampling time, the chamber was placed on top of the soil ring for a total of 40 minutes, and 3 samples, 20 minutes apart, were taken using a syringe through a rubber septum on top of the gas chamber. Samples were taken twice weekly. Each sampling was carried out during the middle of the day between 12:00 h to 14:00 h (Di et al., 2007). The $N_2O$ concentration in the samples was analysed using a gas chromatograph (SRI8610C with an Electron Capture Detector (ECD) (SRI Instruments, USA) linked to a Gilson 222XL autosampler (Gilson, France).

FIG. 6(D) shows the effectiveness of 2-ethynyl-5-methoxypyridine in reducing $N_2O$—N emissions when 2-ethynyl-5-methoxypyridine was sprayed onto soil surface with pasture in the field which had received animal urine. $N_2O$—N emissions in the urine+2-ethynyl-5-methoxypyridine treated soil were about 85% lower than that in the urine alone control treatment when 2-ethynyl-5-methoxypyridine was applied at 10 kg/ha and 2 kg/ha. This shows the efficiency of 2-ethynyl-5-methoxypyridine in reducing $N_2O$ emissions in the soil.

The effect of 2-ethynyl-5-methoxypyridine on nitrate concentrations and nitrous oxide emissions in Studies 1-4 are shown in Table 1-6 below:

TABLE 1-6

| Effect of new nitrification inhibitors (NI) on nitrate concentration or nitrous oxide emissions | | | % reduction by NI |
|---|---|---|---|
| Study 1 | | Urine / Urine + 2-ethynyl-5-methoxypyridine (2 kg/ha) | |
| | Nitrate-N (mg N/kg soil) | 457.8 / 100 | 78% |
| Study 2 | | Urine / Urine + 2-ethynyl-5-methoxypyridine (1 kg/ha) | |
| | Nitrate-N (mg N/kg soil) | 491.8 / 13.8 | 97% |
| Study 3 | | Urine / Urine + 2-ethynyl-5-methoxypyridine (0.5 kg/ha) | |
| | Nitrate-N (mg N/kg soil) | 393.9 / 28.6 | 93% |
| Study 4 | | Urine / Urine + 2-ethynyl-5-methoxypyridine (10 kg/ha) | |
| | N2O emissions (kg N2O—N/ha) | 13.0 / 2 | 85% |
| | | Urine / Urine + 2-ethynyl-5-methoxypyridine (2 kg/ha) | |
| | N2O emissions (kg N2O—N/ha) | 13.0 / 2 | 85% |

Testing 5-ethynyl-2-methoxypyridine

Study 1-7

A laboratory incubation study was conducted to determine the efficacy of 5-ethynyl-2-methoxypyridine in nitrification inhibition when applied at a rate of 2 kg/ha. The experimental procedures are the same as described in Study 1-1.

Figure 7:
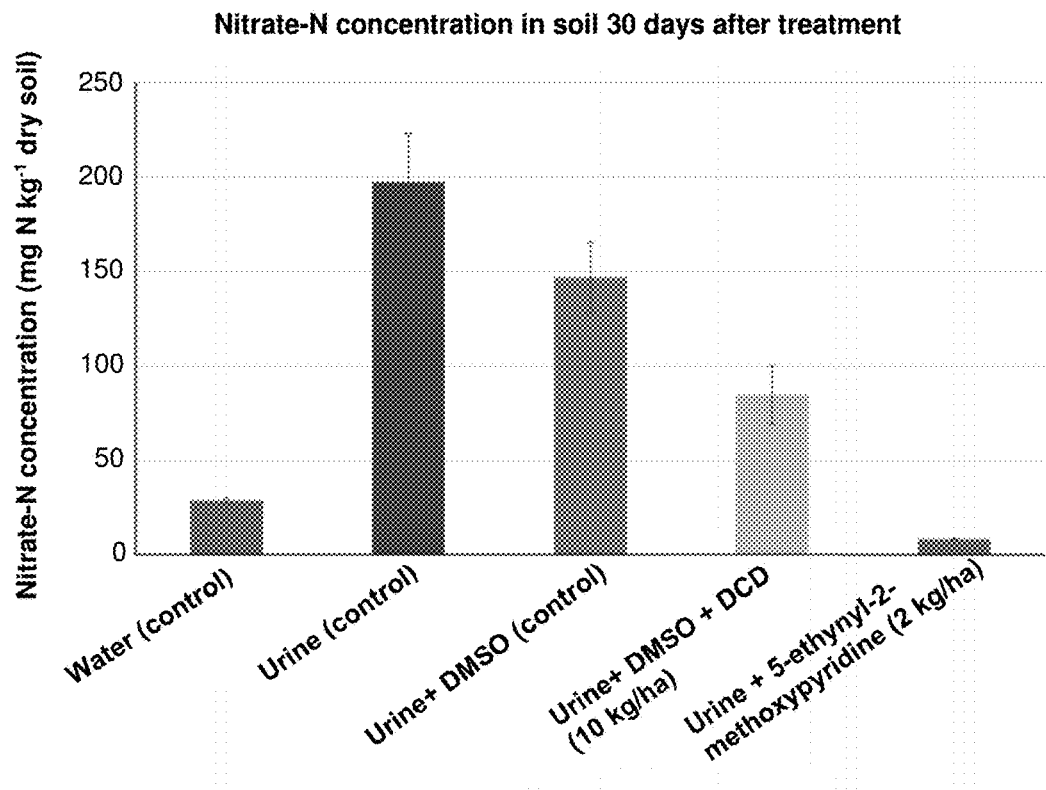
FIG. 7 shows the nitrate-N concentration in the soil at the end of 30 days of incubation, as affected by the application of 5-ethynyl-2-methoxypyridine at 2 kg/ha, illustrating the highly efficient inhibition of nitrification by 5-ethynyl-2-methoxypyridine, as shown by the lower nitrate-N concentrations in the urine+5-ethynyl-2-methoxypyridine treated soil compared with the urine alone or urine+dimethyl sulfoxide (DMSO) control treatments. The error bars represent one standard error of the mean (SEM).

FIG. 7 shows the nitrate-N concentration in the soil at the end of 30 days of incubation, as affected by the application of 5-ethynyl-2-methoxypyridine at 2 kg/ha to soil, illustrating the highly efficient inhibition of nitrification by 5-ethynyl-2-methoxypyridine, as shown by the lower nitrate-N concentrations in the urine+5-ethynyl-2-methoxypyridine treated soil compared with the urine alone or urine+DMSO control treatments.

Testing 3-ethynylpyridine 1-oxide
Study 1-8

A laboratory incubation study was conducted to determine the efficacy of 3-ethynylpyridine 1-oxide in nitrification inhibition when applied at a rate of 2 kg/ha. The experimental procedures are substantially the same as described in Study 1-1.

Figure 8:
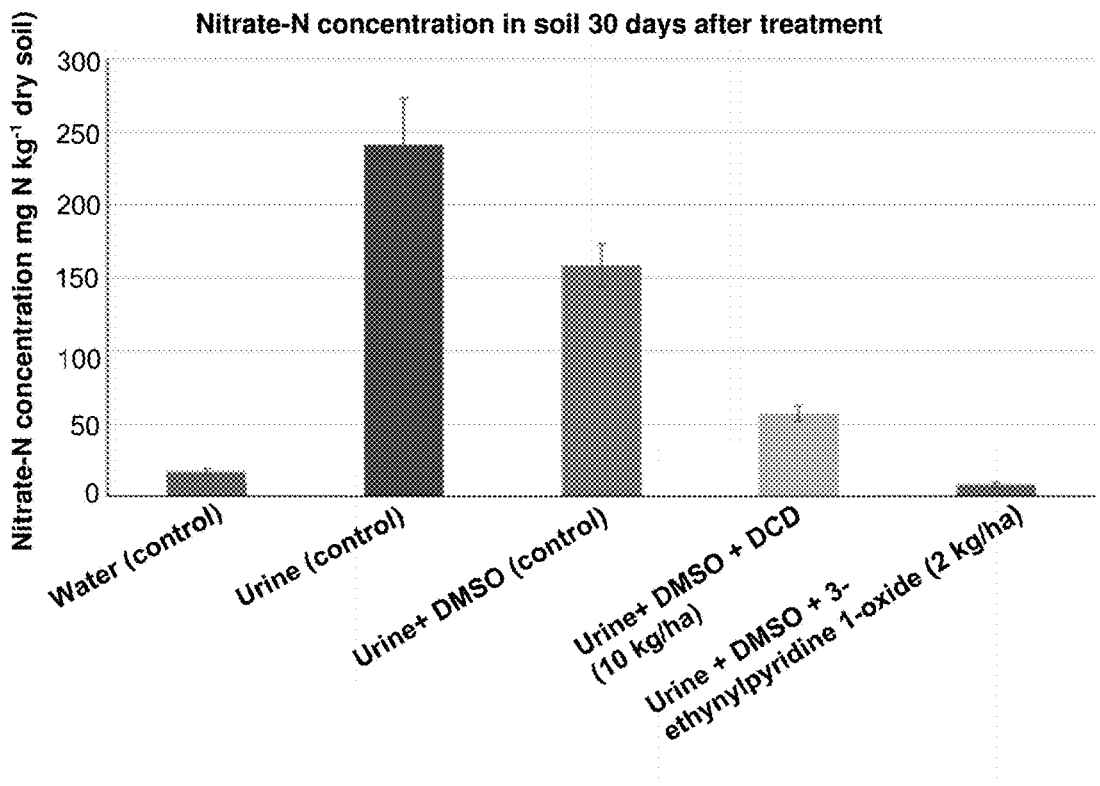
FIG. 8. (A) shows the nitrate-N concentration in the soil at the end of 30 days of incubation, as affected by the application of 3-ethynylpyridine 1-oxide at 2 kg/ha, illustrating the highly efficient inhibition of nitrification by 3-ethynylpyridine 1-oxide, as shown by the lower nitrate-N concentrations in the urine+3-ethynylpyridine 1-oxide treated soil compared with the urine alone or urine+dimethyl sulfoxide (DMSO) control treatments. The error bars represent one standard error of the mean (SEM). (B) shows the nitrate-N concentration in the soil at the end of 30 days of incubation, as affected by the application of 3-ethynylpyridine 1-oxide at 1 kg/ha, illustrating the highly efficient inhibition of nitrification by 3-ethynylpyridine 1-oxide, as shown by the lower nitrate-N concentrations in the urine+3-ethynylpyridine 1-oxide treated soil compared with the urine alone or urine+DMSO control treatments. The error bars represent one standard error of the mean (SEM). (C) shows the nitrate-N concentration in the soil at the end of 30 days of incubation, as affected by the application of 3-ethynylpyridine 1-oxide at 0.5 kg/ha, illustrating the highly efficient inhibition of nitrification 3-ethynylpyridine 1-oxide, as shown by the lower nitrate-N concentrations in the urine+3-ethynylpyridine 1-oxide treated soil compared with the urine alone or urine+DMSO control treatments. The error bars represent one standard error of the mean (SEM). (D) shows the effectiveness of 3-ethynylpyridine 1-oxide in reducing $N_2O$—N emissions when 3-ethynylpyridine 1-oxide was sprayed to soil surface with pasture in the field which had received animal urine. $N_2O$—N emissions in the urine+3-ethynylpyridine 1-oxide treated soil were about 96% and 91% lower than that in the urine alone control treatment when 3-ethynylpyridine 1-oxide was applied at 10 kg/ha and 2 kg/ha, respectively. This shows the efficiency of 3-ethynylpyridine 1-oxide in reducing $N_2O$ emissions in the soil. The nitrous oxide reductions by 3-ethynylpyridine 1-oxide were greater than that by DCD. The error bars in the figure represent one standard error of the mean (SEM).
Figure 8:
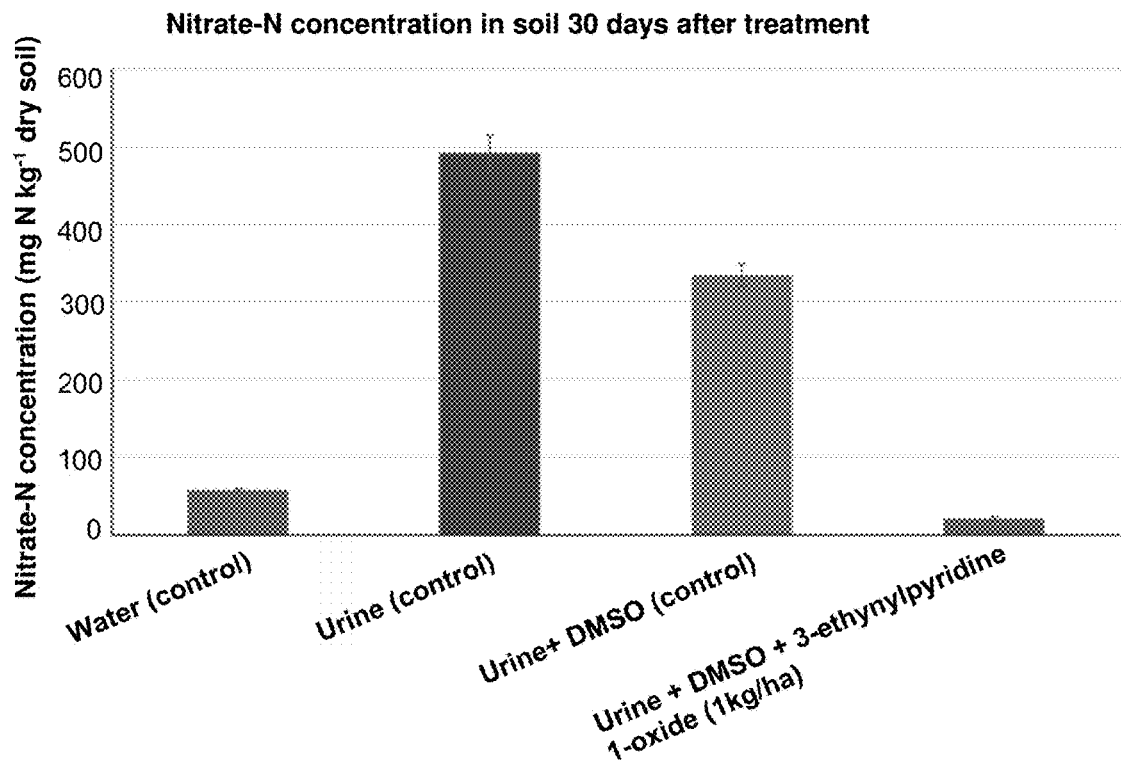
Figure 8:
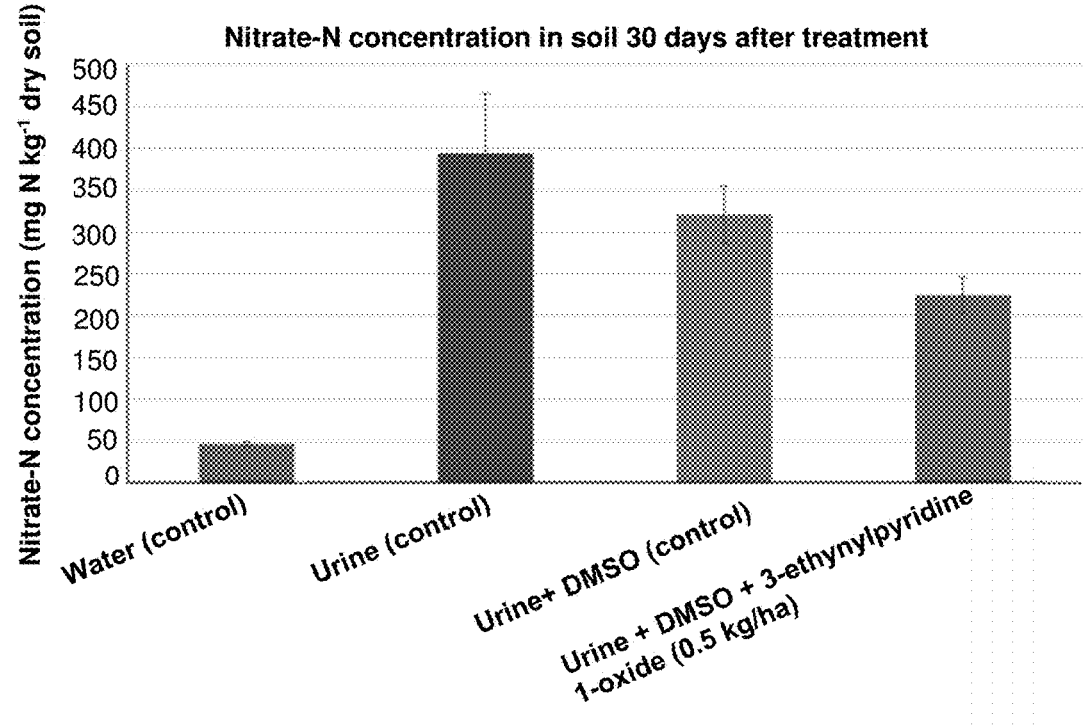
Figure 8:
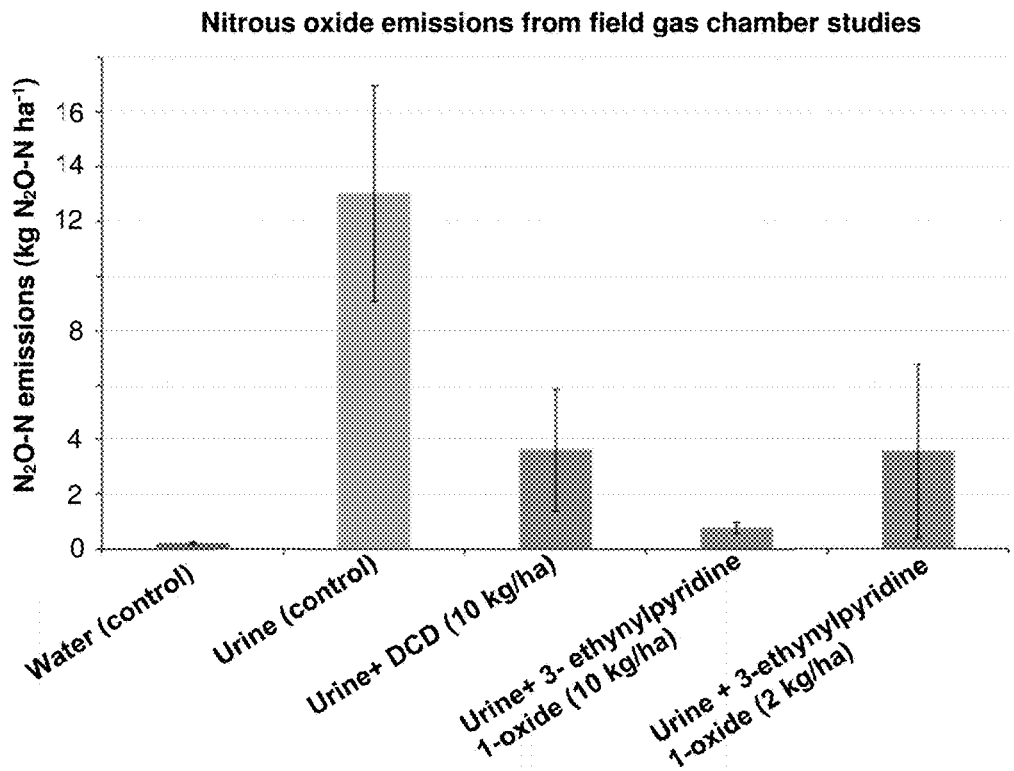

FIG. 8(A) shows the nitrate-N concentration in the soil at day 30 of incubation, showing significantly lower nitrate-N concentrations in the urine+(3-ethynylpyridine 1-oxide dissolved in DMSO) treatment, demonstrating the ability of 3-ethynylpyridine 1-oxide to inhibit nitrification in the soil at 2 kg/ha. These results show that when 3-ethynylpyridine 1-oxide is applied to treat urine patches in soil at 2 kg/ha, significant reductions in nitrification rate can be achieved. In particular, 3-ethynylpyridine 1-oxide at a concentration of only 2 kg/ha was more effective than DCD at a higher concentration of 10 kg/ha at reducing the nitrification rate.

Study 2-8

A second laboratory incubation study was conducted to determine the efficacy of 3-ethynylpyridine 1-oxide in nitrification inhibition when applied at a lower rate of 1 kg/ha. The experimental procedures are the same as described in Study 1-1.

FIG. 8(B) shows the nitrate-N concentration in the soil at the end of 30 days of incubation, as affected by the application of 3-ethynylpyridine 1-oxide at 1 kg/ha to soil, illustrating the highly efficient inhibition of nitrification by 3-ethynylpyridine 1-oxide, as shown by the lower nitrate-N concentrations in the urine+3-ethynylpyridine 1-oxide treated soil compared with the urine alone or urine+DMSO control treatments.

Study 3-8

A third laboratory incubation study was conducted to determine the efficacy of 3-ethynylpyridine 1-oxide in nitrification inhibition when applied at a lower rate of 0.5 kg/ha to soil. The experimental procedures are the same as described in Study 1-1.

FIG. 8(C) shows the nitrate-N concentration in the soil at the end of 30 days of incubation, as affected by the application of 3-ethynylpyridine 1-oxide at 0.5 kg/ha, illustrating inhibition of nitrification by 3-ethynylpyridine 1-oxide at this very low application rate, as shown by the lower nitrate-N concentrations in the urine+3-ethynylpyridine 1-oxide treated soil compared with the urine alone or urine+DMSO control treatments.

Study 4-8

To determine the effect of treating the soil with 3-ethynylpyridine 1-oxide on nitrous oxide emissions under field soil conditions, a field study was conducted using the static gas chamber method. This study was conducted on the Lincoln University Research Dairy Farm, and the soil was a Templeton sandy loam with established perennial ryegrass (*Lolium perenne*) and white clover (*Trifolium repens*.) pasture. Metal rings (500 mm diameter and 200 mm height) were inserted into the ground. A water trough sitting on top of the metal rings allowed the placement of static chambers sitting on top of the water trough to provide a gas-tight seal to allow $N_2O$ gas sampling.

Synthetic urine with a nitrogen concentration of 7 g N/L was applied to the soil plots confined within the metal rings at the equivalent rate of 700 kg N/ha. 196.25 mg or 39.2 mg of 3-ethynylpyridine 1-oxide were dissolved in 2 mL DMSO, mixed with 1000 mL of water, and then sprayed on to the mini-plots at the rates of 196.25 mg/plot and 39.2 mg/plot, equivalent to 10 kg/ha and 2 kg/ha, respectively. The plots were irrigated with irrigation water in accordance with local dairy farming practice.

The gas chamber (500 mm diameter and 120 mm height) was constructed of a metal cylinder insulated with 2.5 cm thick polystyrene foam to avoid heating of the atmosphere in the chamber during sampling. During periods of $N_2O$ measurement, the edge of the chamber was placed inside the small water trough which was mounted around the top of each metal ring for gas sampling. At each sampling time, the chamber was placed on top of the soil ring for a total of 40 minutes, and 3 samples, 20 minutes apart, were taken using a syringe through a rubber septum on top of the gas chamber. Samples were taken twice weekly. Each sampling was carried out during the middle of the day between 12:00 h to 14:00 h (Di et al., 2007). The $N_2O$ concentration in the samples was analysed using a gas chromatograph (SRI8610C with an Electron Capture Detector (ECD) (SRI Instruments, USA) linked to a Gilson 222XL autosampler (Gilson, France).

FIG. 8(D) shows the effectiveness of 3-ethynylpyridine 1-oxide in reducing $N_2O$—N emissions when 3-ethynylpyridine 1-oxide was sprayed to soil surface with pasture in the field which had received animal urine. $N_2O$—N emissions in the urine+3-ethynylpyridine 1-oxide treated soil were about 94% lower than that in the urine alone control treatment when 3-ethynylpyridine 1-oxide was applied at 10 kg/ha, and 72% lower when 3-ethynylpyridine 1-oxide was applied at 2 kg/ha. This shows the efficiency of 3-ethynylpyridine 1-oxide in reducing $N_2O$ emissions in the soil. This shows the efficiency of 3-ethynylpyridine 1-oxide in reducing $N_2O$ emissions in the soil.

The effect of 3-ethynylpyridine 1-oxide on nitrate concentrations and nitrous oxide emissions in Studies 1-4 are shown in Table 1-8 below:

TABLE 1-8

Effect of new nitrification inhibitors (NI) on nitrate concentration or nitrous oxide emissions     % reduction by NI

| Study 1 |  | Urine | Urine + 3-ethynylpyridine 1-oxide (2 kg/ha) |  |
|---|---|---|---|---|
|  | Nitrate-N (mg N/kg soil) | 241.1 | 8.2 | 97% |
| Study 2 |  | Urine | Urine + 3-ethynylpyridine 1-oxide (1 kg/ha) |  |
|  | Nitrate-N (mg N/kg soil) | 491.8 | 20.8 | 96% |
| Study 3 |  | Urine | Urine + 3-ethynylpyridine 1-oxide (0.5 kg/ha) |  |
|  | Nitrate-N (mg N/kg soil) | 393.9 | 224.4 | 43% |

TABLE 1-8-continued

| Effect of new nitrification inhibitors (NI) on nitrate concentration or nitrous oxide emissions | | | % reduction by NI |
|---|---|---|---|
| Study 4 | Urine | Urine + 3-ethynylpyridine 1-oxide (10 kg/ha) | |
| N2O emissions (kg N2O—N/ha) | 13.0 | 0.79 | 94% |
| | Urine | Urine + 3-ethynylpyridine 1-oxide (2 kg/ha) | |
| N2O emissions (kg N2O—N/ha) | 13.0 | 3.6 | 72% |

Testing 2,5-diethynylpyridine
Study 1-9

A laboratory incubation study was conducted to determine the efficacy of 2,5-diethynylpyridine in nitrification inhibition when applied at a rate of 2 kg/ha. The experimental procedures are the same as described in Study 1-1.

Figure 9:
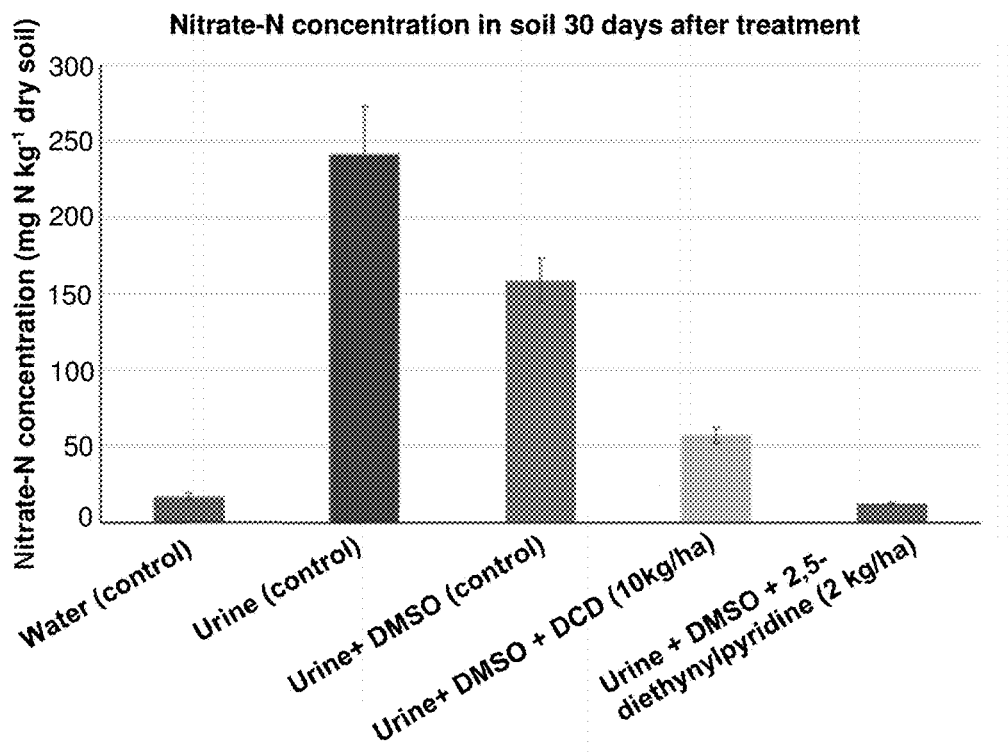
FIG. 9 shows the nitrate-N concentration in the soil at the end of 30 days of incubation, as affected by the application of 2,5-diethynylpyridine at 2 kg/ha, illustrating the highly efficient inhibition of nitrification by 2,5-diethynylpyridine, as shown by the lower nitrate-N concentrations in the urine+2,5-diethynylpyridine treated soil compared with the urine alone or urine+dimethyl sulfoxide (DMSO) control treatments. The error bars represent one standard error of the mean (SEM).

FIG. 9 shows the nitrate-N concentration in the soil at the end of 30 days of incubation, as affected by the application of 2,5-diethynylpyridine at 2 kg/ha to soil, illustrating the highly efficient inhibition of nitrification by 2,5-diethynylpyridine, as shown by the lower nitrate-N concentrations in the urine+2,5-diethynylpyridine treated soil compared with the urine alone or urine+DMSO control treatments.

Testing 3-Ethynylpyridazine

3-Ethynylpyridazine is a commercially available compound which can be sourced from many suppliers who can be found online using (CAS 1017793-08-6) see for example: https://www.chemicalbook.com/ChemicalProduct-Pro- perty_EN_CB_72570313.htm Study 1-10

A laboratory incubation study was conducted to determine the efficacy of 3-Ethynylpyridazine in nitrification inhibition when applied at a rate of 2 kg/ha. The experimental procedures are the same as described in Study 1-1.

Figure 10:
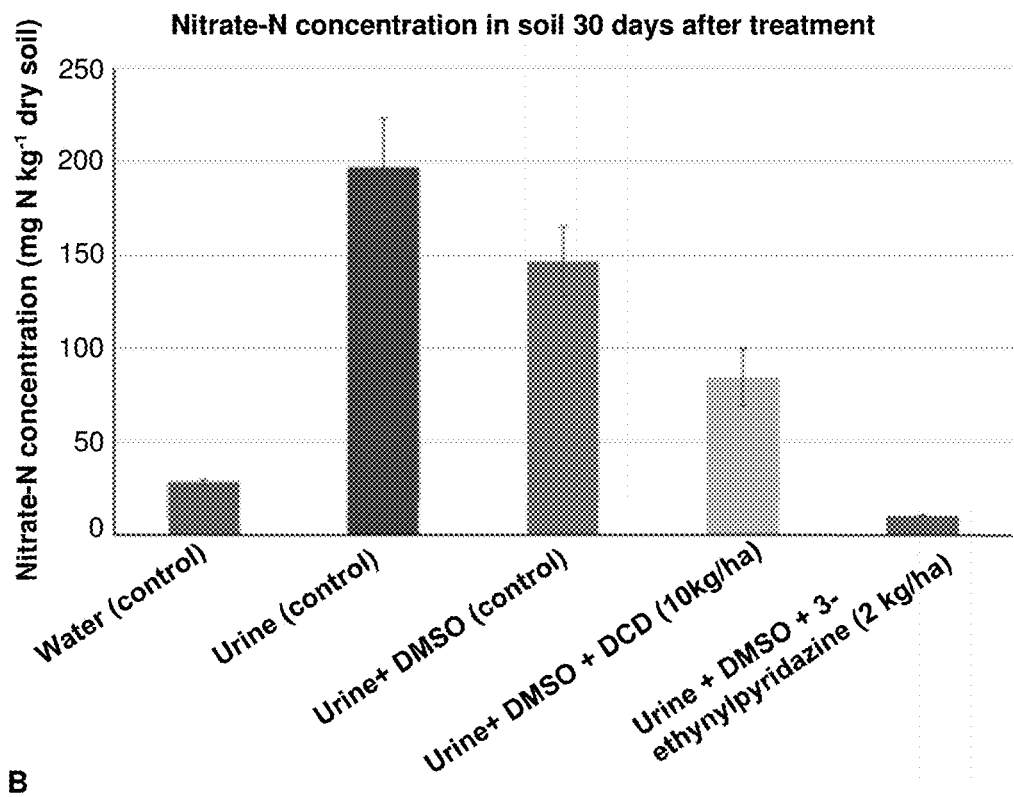
FIG. 10. (A) shows the nitrate-N concentration in the soil at the end of 30 days of incubation, as affected by the application of 3-Ethynylpyridazine at 2 kg/ha, illustrating the highly efficient inhibition of nitrification by 3-Ethynylpyridazine, as shown by the lower nitrate-N concentrations in the urine+3-Ethynylpyridazine treated soil compared with the urine alone or urine+dimethyl sulfoxide (DMSO) control treatments. The error bars represent one standard error of the mean (SEM). (B) shows the nitrate-N concentration in the soil at the end of 30 days of incubation, as affected by the application of 3-Ethynylpyridazine at 1 kg/ha, illustrating the highly efficient inhibition of nitrification by 3-Ethynylpyridazine, as shown by the lower nitrate-N concentrations in the urine+3-Ethynylpyridazine treated soil compared with the urine alone or urine+DMSO control treatments. The error bars represent one standard error of the mean (SEM). (C) shows the nitrate-N concentration in the soil at the end of 30 days of incubation, as affected by the application of 3-Ethynylpyridazine at 0.5 kg/ha, illustrating the highly efficient inhibition of nitrification by 3-Ethynylpyridazine, as shown by the lower nitrate-N concentrations in the urine+3-Ethynylpyridazine treated soil compared with the urine alone or urine+DMSO control treatments. The error bars represent one standard error of the mean (SEM).
Figure 10:
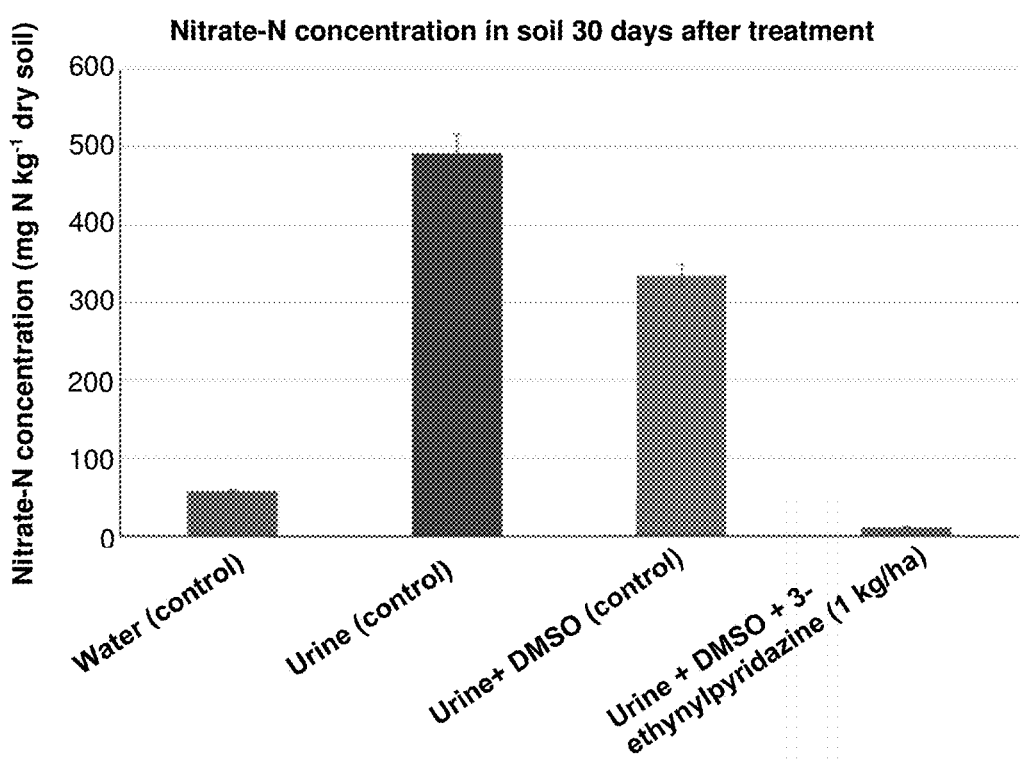
Figure 10:
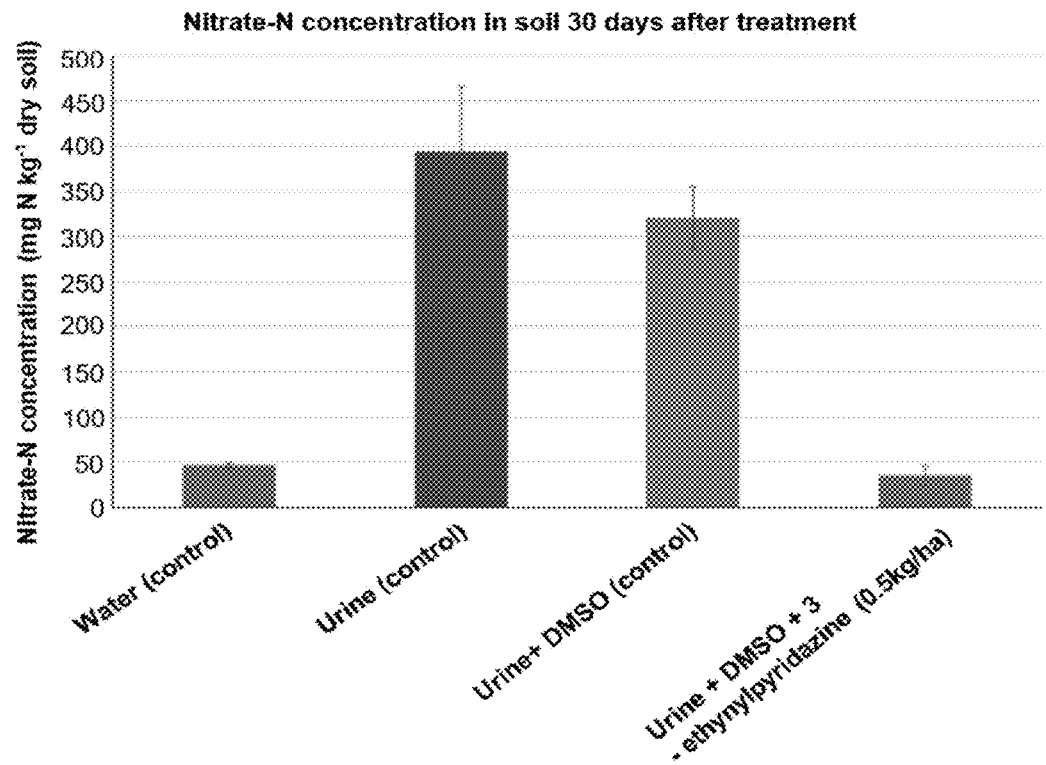

FIG. 10(A) shows the nitrate-N concentration in the soil at day 30 of incubation, showing significantly lower nitrate-N concentrations in the urine+(3-Ethynylpyridazine dissolved in DMSO) treatment, demonstrating the ability of 3-Ethynylpyridazine to inhibit nitrification in the soil at 2 kg/ha. These results show that when 3-Ethynylpyridazine is applied to treat urine patches in soil at 2 kg/ha, significant reductions in nitrification rate can be achieved. In particular, 3-Ethynylpyridazine at a concentration of only 2 kg/ha was more effective than DCD at a higher concentration of 10 kg/ha at reducing the nitrification rate.

Study 2-10

A second laboratory incubation study was conducted to determine the efficacy of 3-Ethynylpyridazine in nitrification inhibition when applied at a lower rate of 1 kg/ha. The experimental procedures are the same as described in Study 1-1.

FIG. 10(B) shows the nitrate-N concentration in the soil at the end of 30 days of incubation, as affected by the application of 3-Ethynylpyridazine at 1 kg/ha to soil, illustrating the highly efficient inhibition of nitrification by 3-Ethynylpyridazine, as shown by the lower nitrate-N concentrations in the urine+3-Ethynylpyridazine treated soil compared with the urine alone or urine+DMSO control treatments.

Study 3-10

A third laboratory incubation study was conducted to determine the efficacy of 3-Ethynylpyridazine in nitrification inhibition when applied at a lower rate of 0.5 kg/ha to soil. The experimental procedures are the same as described in Study 1-1.

FIG. 10(C) shows the nitrate-N concentration in the soil at the end of 30 days of incubation, as affected by the application of 3-Ethynylpyridazine at 0.5 kg/ha, illustrating the highly efficient inhibition of nitrification by 3-Ethynylpyridazine at this very low application rate, as shown by the lower nitrate-N concentrations in the urine+3-Ethynylpyridazine treated soil compared with the urine alone or urine+DMSO control treatments.

The effect of 3-Ethynylpyridazine on nitrate concentrations in soil in Studies 1-3 are shown in Table 1-10 below:

TABLE 1-10

| Effect of new nitrification inhibitors (NI) on nitrate concentration in soil | | | % reduction by NI |
|---|---|---|---|
| Study 1 | Urine | Urine + 3-ethynylpyridazine (2 kg/ha) | |
| Nitrate-N (mg N/kg soil) | 197.2 | 10.5 | 95% |
| Study 2 | Urine | Urine + 3-ethynylpyridazine (1 kg/ha) | |
| Nitrate-N (mg N/kg soil) | 491.8 | 10.3 | 98% |
| Study 3 | Urine | Urine + 3-ethynylpyridazine (0.5 kg/ha) | |
| Nitrate-N (mg N/kg soil) | 393.9 | 35.5 | 91% |

Testing 3-Ethynyl-6-methoxypyridazine
Study 1-11

A laboratory incubation study was conducted to determine the efficacy of 3-Ethynyl-6-methoxypyridazine in nitrification inhibition when applied at a rate of 2 kg/ha and 1 kg/ha. The experimental procedures are the same as described in Study 1-1.

Figure 11:
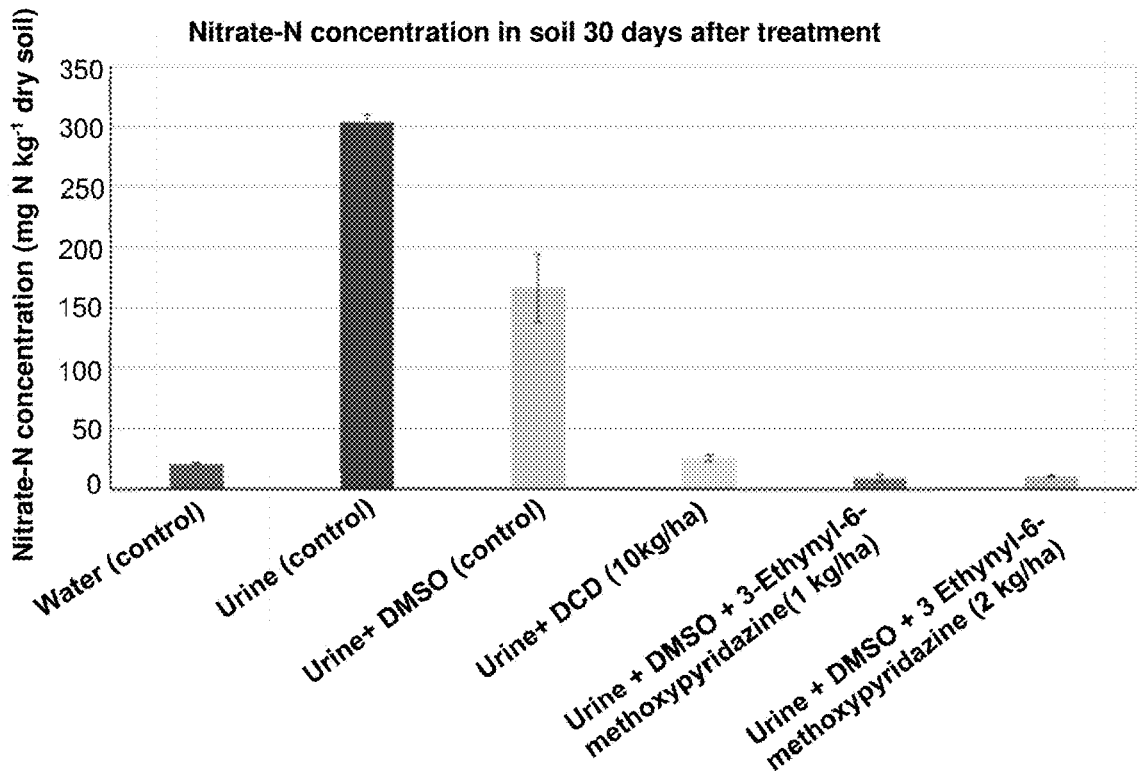
FIG. 11 shows the nitrate-N concentration in the soil at the end of 30 days of incubation, as affected by the application of 3-Ethynyl-6-methoxypyridazine at 2 kg/ha or 1 kg/ha, illustrating the highly efficient inhibition of nitrification by 3-Ethynyl-6-methoxypyridazine, as shown by the lower nitrate-N concentrations in the urine+3-Ethynyl-6-methoxypyridazine treated soil compared with the urine alone or urine+dimethyl sulfoxide (DMSO) control treatments. The error bars represent one standard error of the mean (SEM).

FIG. 11 shows the nitrate-N concentration in the soil at the end of 30 days of incubation, as affected by the application of 3-Ethynyl-6-methoxypyridazine at 2 kg/ha or 1 kg/ha to soil, illustrating the highly efficient inhibition of nitrification by 3-Ethynyl-6-methoxypyridazine, as shown by the lower nitrate-N concentrations in the urine+3-Ethynyl-6-methoxypyridazine treated soil compared with the urine alone or urine+DMSO control treatments.

Route Towards 3-Ethynyl-6-methoxypyridazine

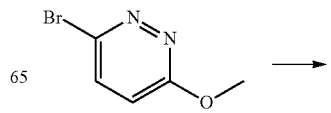

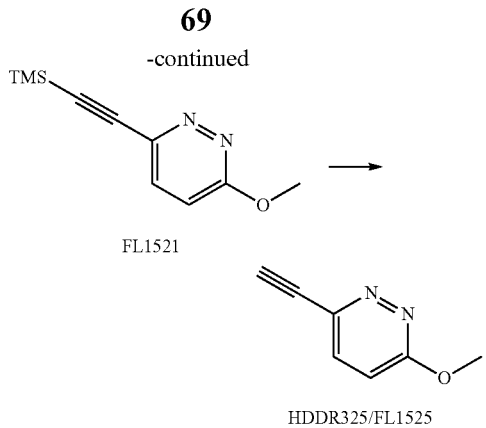

FL1521

↓

HDDR325/FL1525

A suspension of 3-bromo-6-methoxypyridazine (3.00 g, 15.9 mmol, 1.0 eqv.), ethynyltrimethylsilane (3.3 mL, 23.8 mmol, 1.5 eqv.), triethylamine (11.1 mL, 79.4 mmol, 5.0 eqv.), bis(triphenylphosphine)palladium(II) dichloride (557 mg, 0.79 mmol, 0.05 eqv.) and copper(I) iodide (303 mg, 1.6 mmol, 0.1 eqv.) in degassed anhydrous tetrahydrofuran (50 mL) was heated at reflux under argon for 18 h.

The mixture was cooled to room temperature, filtered through Celite® and the filtrate was concentrated in vacuo.

Purification by column chromatography (petroleum ether/ethyl acetate 19:1) afforded 3-methoxy-6-((trimethylsilyl)ethynyl)pyridazine (FL1521) as a brown solid (560 mg, 17%). $^1$H NMR (400 MHz, CDCl$_3$) δ 0.26 (9H, s), 4.13 (3H, s), 6.89 (1H, d, J=9.3 Hz), 7.42 (1H, d, J=8.8 Hz); $^{13}$C NMR (100 MHz, CDCl$_3$) δ −0.2 (CH3), 55.1 (CH3), 98.4 (C), 100.8 (C), 116.6 (CH), 132.6 (CH), 143.5 (C), 163.5 (C).

A mixture of 3-methoxy-6-((trimethylsilyl)ethynyl)pyridazine (FL1521, 560 mg, 2.7 mmol, 1.0 eqv.) and potassium carbonate (750 mg, 5.4 mmol, 2.0 eqv.) in diethyl ether-methanol (13.5 mL, 4:1 v/v) was stirred at room temperature for 2 h.

The mixture was then filtered and the filtrate was diluted with diethyl ether (50 mL) and saturated aqueous ammonium chloride solution (50 mL).

The separated aqueous layer was further extracted with diethyl ether (2×30 mL) and the combined organic extracts were dried over anhydrous sodium sulfate, filtered and concentrated in vacuo.

Purification by column chromatography (hexanes/ethyl acetate 19:1) afforded 3-ethynyl-6-methoxypyridazine (HDDR325/FL1525) as a brown solid (260 mg, 71%). mp 51.7-53.1° C.; $^1$H NMR (400 MHz, CDCl$_3$) δ 3.29 (1H, s), 4.12 (3H, s), 6.91 (1H, d, J=9.4 Hz), 7.44 (1H, d, J=9.4 Hz); $^{13}$C NMR (100 MHz, CDCl$_3$) δ 55.2 (CH3), 80.0 (C), 80.3 (CH), 116.6 (CH), 132.6 (CH), 142.7 (C), 163.8 (C); HRMS (ESI+): [M+Na]$^+$ calcd for C$_7$H$_6$N$_2$NaO, 157.0372; found, 157.0374.

Testing 2-ethynylpyrazine
Study 1-12

A laboratory incubation study was conducted to determine the efficacy of 2-ethynylpyrazine in nitrification inhibition when applied at a rate of 2 kg/ha. The experimental procedures are the same as described in Study 1-1.

Figure 12:
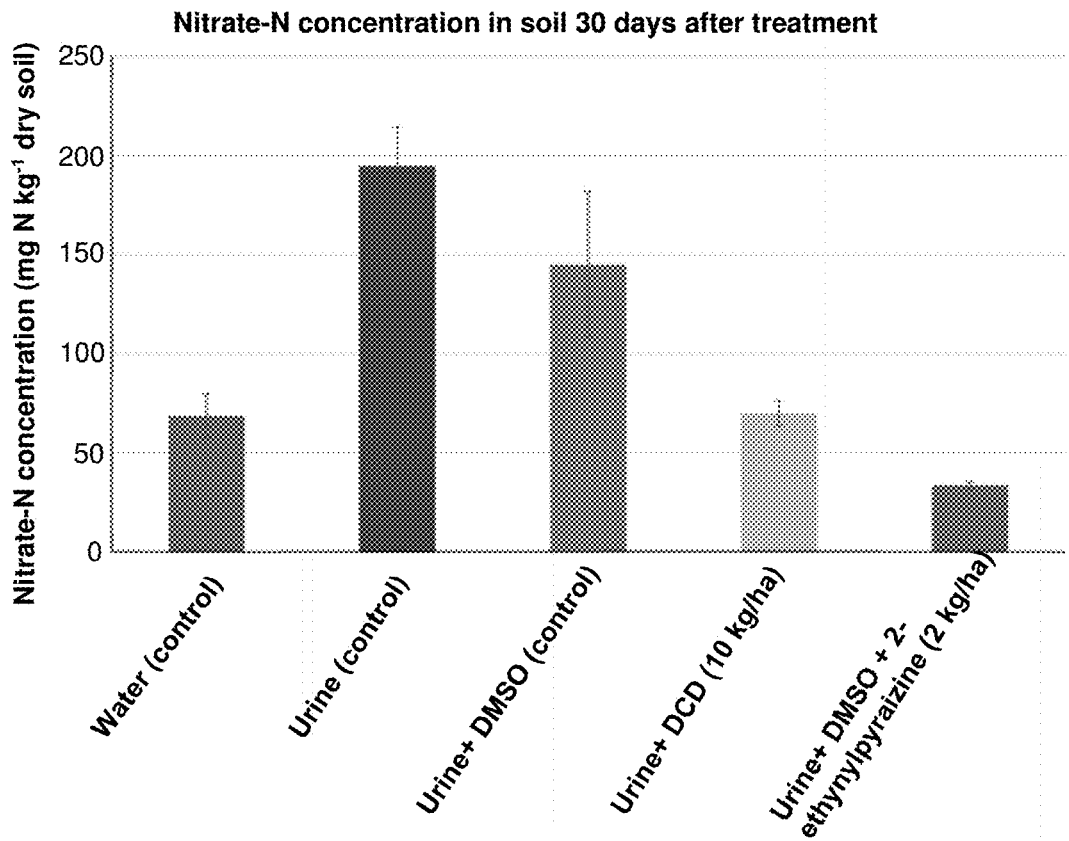
FIG. 12 shows the nitrate-N concentration in the soil at the end of 30 days of incubation, as affected by the application of 2-ethynylpyrazine at 2 kg/ha, illustrating the highly efficient inhibition of nitrification by 2-ethynylpyrazine, as shown by the lower nitrate-N concentrations in the urine+2-ethynylpyrazine treated soil compared with the urine alone or urine+dimethyl sulfoxide (DMSO) control treatments. The error bars represent one standard error of the mean (SEM).

FIG. 12 shows the nitrate-N concentration in the soil at day 30 of incubation, showing significantly lower nitrate-N concentrations in the urine+(2-ethynylpyrazine dissolved in DMSO) treatment, demonstrating the ability of 2-ethynylpyrazine to inhibit nitrification in the soil at 2 kg/ha. These results show that when 2-ethynylpyrazine is applied to treat urine patches in soil at 2 kg/ha, significant reductions in nitrification rate can be achieved. In particular, 2-ethynylpyrazine at a concentration of only 2 kg/ha was more effective than DCD at a higher concentration of 10 kg/ha at reducing the nitrification rate.

Testing 2-Ethynyl-5-methoxypyrazine
Study 1-13

A laboratory incubation study was conducted to determine the efficacy of 2-Ethynyl-5-methoxypyrazine in nitrification inhibition when applied at a rate of 2 kg/ha and 1 kg/ha. The experimental procedures are the same as described in Study 1-1.

Figure 13:
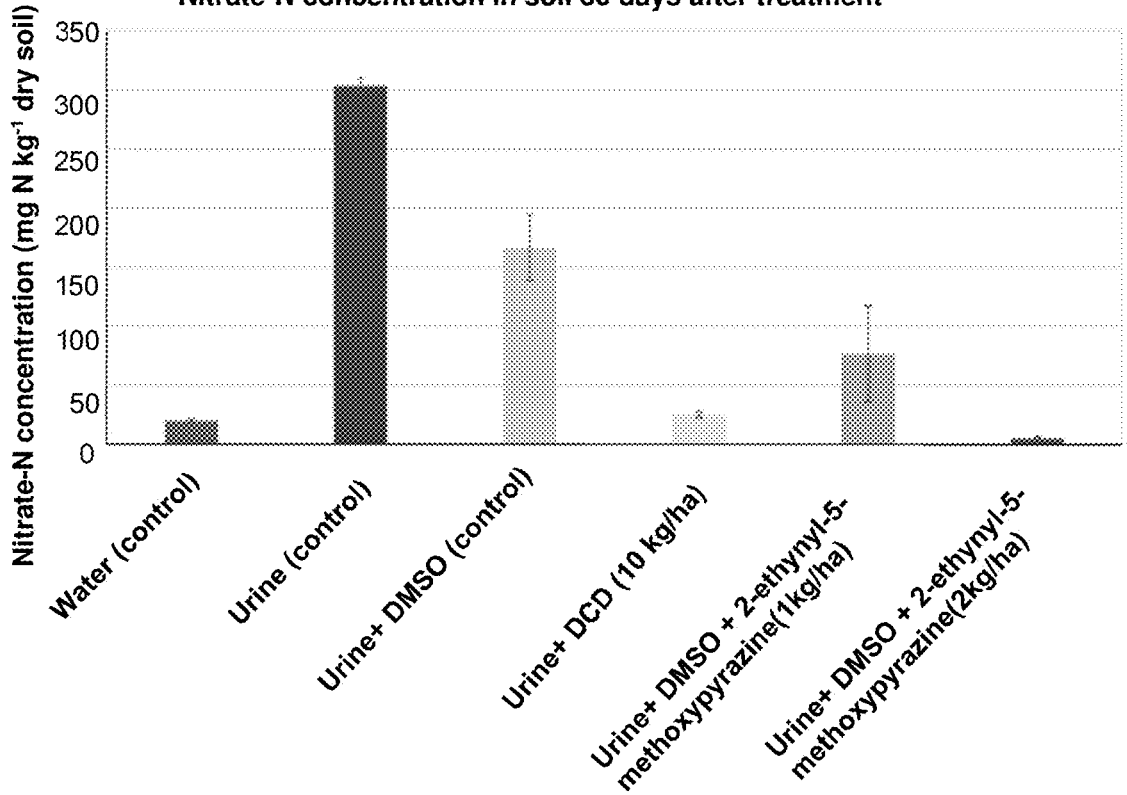
FIG. 13 shows the nitrate-N concentration in the soil at the end of 30 days of incubation, as affected by the application of 2-Ethynyl-5-methoxypyrazine at 2 kg/ha or 1 kg/ha, illustrating the highly efficient inhibition of nitrification by 2-Ethynyl-5-methoxypyrazine, as shown by the lower nitrate-N concentrations in the urine+2-Ethynyl-5-methoxypyrazine treated soil compared with the urine alone or urine+dimethyl sulfoxide (DMSO) control treatments. The error bars represent one standard error of the mean (SEM).

FIG. 13 shows the nitrate-N concentration in the soil at the end of 30 days of incubation, as affected by the application of 2-Ethynyl-5-methoxypyrazine at 2 kg/ha or 1 kg/ha to soil, illustrating the highly efficient inhibition of nitrification by 2-Ethynyl-5-methoxypyrazine, as shown by the lower nitrate-N concentrations in the urine+2-Ethynyl-5-methoxypyrazine treated soil compared with the urine alone or urine+DMSO control treatments.

Route Towards Synthesis of 2-Ethynyl-5-methoxypyrazine

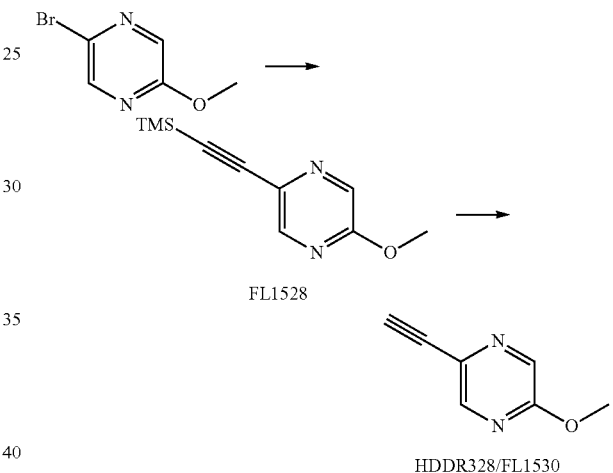

FL1528

↓

HDDR328/FL1530

A suspension of 2-bromo-5-methoxypyrazine (410 mg, 2.2 mmol, 1.0 eqv.), ethynyltrimethylsilane (0.5 mL, 3.3 mmol, 1.5 eqv.), triethylamine (1.5 mL, 11.0 mmol, 5.0 eqv.), bis(triphenylphosphine) palladium(II) dichloride (76 mg, 0.11 mmol, 0.05 eqv.) and copper(I) iodide (41 mg, 0.22 mmol, 0.1 eqv.) in degassed anhydrous tetrahydrofuran (8 mL) was stirred at room temperature under argon for 1 h.

The mixture was filtered through Celite® and the filtrate was concentrated in vacuo. Purification by column chromatography (hexanes/ethyl acetate 49:1) afforded 2-methoxy-5-((trimethylsilyl) ethynyl)pyrazine (FL1528) as a pale yellow liquid (295 mg, 66%). 1H NMR (400 MHz, CDCl$_3$) δ 0.27 (9H, s), 3.97 (3H, s), 8.16 (1H, d, J=1.5 Hz), 8.22 (1H, d, J=1.5 Hz); 13C NMR (100 MHz, CDCl$_3$) δ −0.1 (CH3), 54.1 (CH3), 96.8 (C), 100.9 (C), 131.5 (C), 135.6 (CH), 144.4 (CH), 159.3 (C).

A mixture of 2-methoxy-5-((trimethylsilyl) ethynyl)pyrazine (FL1528, 295 mg, 1.4 mmol, 1.0 eqv.) and potassium carbonate (395 mg, 2.8 mmol, 2.0 eqv.) in diethyl ether-methanol (10 mL, 4:1 v/v) was stirred at room temperature for 3 h.

The mixture was then filtered and the filtrate was diluted with diethyl ether (30 mL) and saturated aqueous ammonium chloride solution (30 mL).

The separated aqueous layer was further extracted with diethyl ether (2×15 mL) and the combined organic extracts were dried over anhydrous sodium sulfate, filtered and concentrated in vacuo.

Purification by column chromatography (n-pentane/diethyl ether 49:1) afforded 2-ethynyl-5-methoxypyrazine (HDDR328/FL1530) as a white solid (140 mg, 73%). mp 41.3-42.7° C.; 1H NMR (400 MHz, CDCl$_3$) δ 3.20 (1H, s), 3.96 (3H, s), 8.16 (1H, d, J=1.4 Hz), 8.24 (1H, d, J=1.4 Hz); 13C NMR (100 MHz, CDCl$_3$) δ 54.1 (CH3), 79.0 (CH), 80.1 (C), 130.6 (C), 135.8 (CH), 144.5 (CH), 159.5 (C); HRMS (ESI+): N/A.

Testing 4-Ethynylanisole

Figure 14:
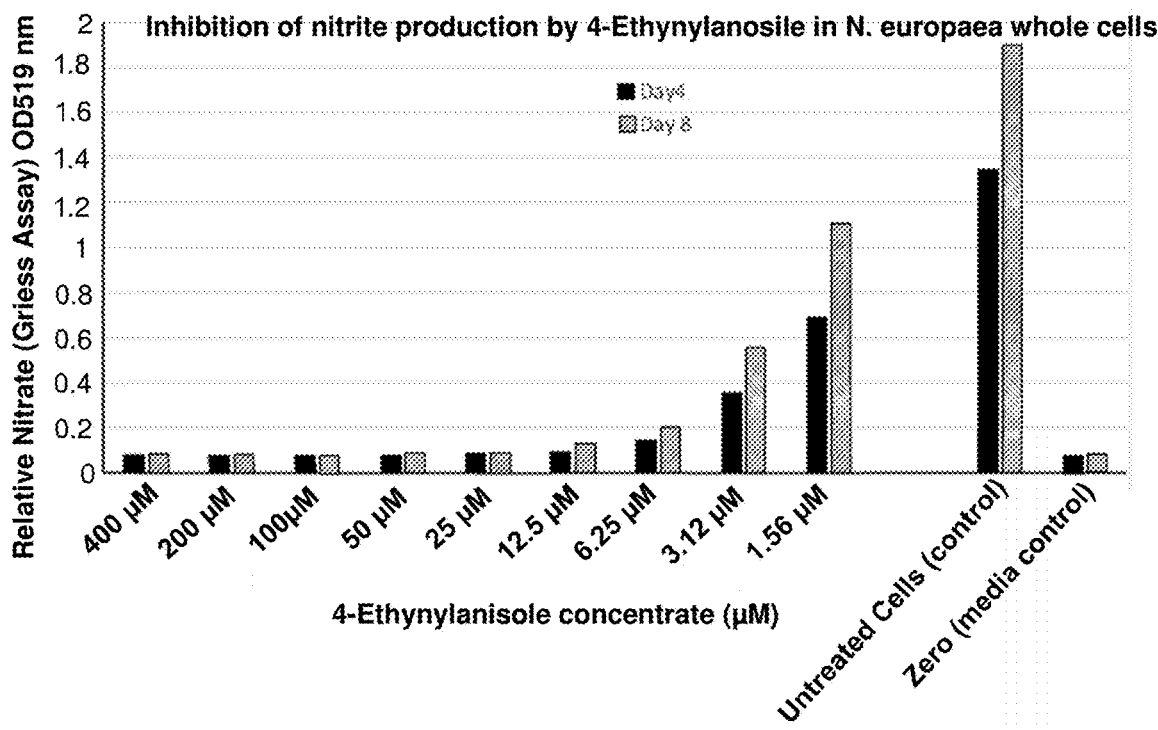
FIG. 14. (A) shows that when 4-Ethynylanisole was applied at a wide range of concentrations in in vitro screening, from 1.56 µM to 400 µM, the rate of nitrite production by *Nitrosomonas europaea* was significantly reduced, indicating effective inhibition of the nitrification process by 4-Ethynylanisole. The OD519 nm reading is an indicator of nitrite concentration in the liquid tested, the higher the reading, the higher the nitrite concentration. (B) shows the changes in nitrate-N concentration in the soil, as affected by the application of different rates of 4-Ethynylanisole. The error bars represent one standard error of the mean (SEM). The figure shows the significantly slower increase in Nitrate-N concentration in the urine+4-Ethynylanisole treated soil compared with that in the urine (control) treated soil, demonstrating the significant inhibition of the nitrification process by 4-Ethynylanisole. The lower the nitrate concentration the lower the risk of nitrate leaching and nitrous oxide emissions. (C) shows the nitrate-N concentration in the soil at the end of 30 days of incubation, as affected by different rates of 4-Ethynylanisole treatment, illustrating the highly efficient inhibition of nitrification by 4-Ethynylanisole, as shown by the lower nitrate-N concentrations in the urine+4-Ethynylanisole treated soil compared with the urine alone control treatment. The error bars represent one standard error of the mean (SEM). (D) shows the nitrate concentration in the soil at the end of 60 days of incubation, as affected by treatment with 4-Ethynylanisole applied at a rate equivalent to 10 kg/ha. The figure shows that 4-Ethynylanisole was much more potent than DCD in inhibiting the nitrate production from urine by inhibiting the nitrification process. The solvent (DMSO) did not result in statistically significant reduction in nitrate concentration compared with the urine alone treatment (P>0.05). The error bars represent one standard error of the mean (SEM). (E) shows the effectiveness of 4-Ethynylanisole in reducing $N_2O$—N emissions when 4-Ethynylanisole was sprayed to soil surface which had received animal urine. $N_2O$—N emissions in the urine+4-Ethynylanisole treated soil was 93.3% lower than that in the urine alone control treatment. This shows the efficiency of 4-Ethynylanisole in reducing $N_2O$ emissions in the soil. The nitrous oxide reduction by 4-Ethynylanisole was much greater than that by DCD which gave 43.4% reduction in $N_2O$ emissions. The error bars in the figure represent one standard error of the mean (SEM). (F) shows the nitrate concentration in the soil at the end of 60 days of incubation, as affected by treatment with 4-Ethynylanisole applied at a rate equivalent to 1 and 2 kg/ha. The figure shows that 4-Ethynylanisole applied at 1 or 2 kg/ha was much more potent than DCD at 10 kg/ha in inhibiting the nitrate production from urine by inhibiting the nitrification process. The error bars represent one standard error of the mean (SEM). (G) and (H) show that the ammonium-driven oxygen consumption was reduced to zero with the presence of 4-Ethynylanisole (G), whereas the hydroxylamine ($H_3NO$)-driven oxygen consumption was not affected by 4-Ethynylanisole (H), indicating that the ammonia monooxygenase enzyme (AMO) of the ammonia oxidising bacteria is the potential target of inhibition by 4-Ethynylanisole, not the hydroxylamine oxidoreductase.
Figure 14:
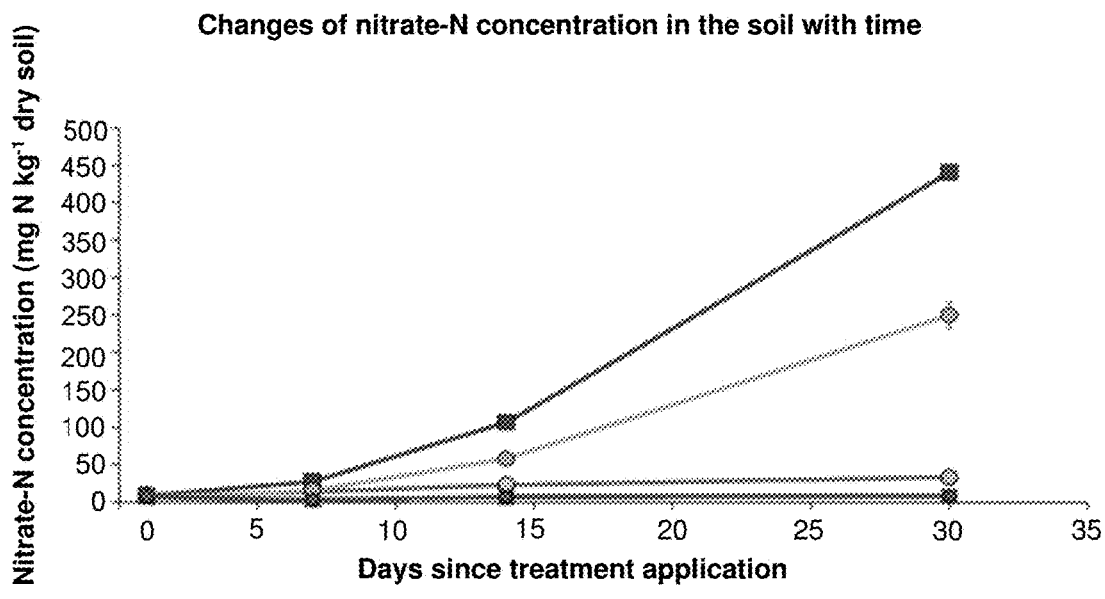
Figure 14:
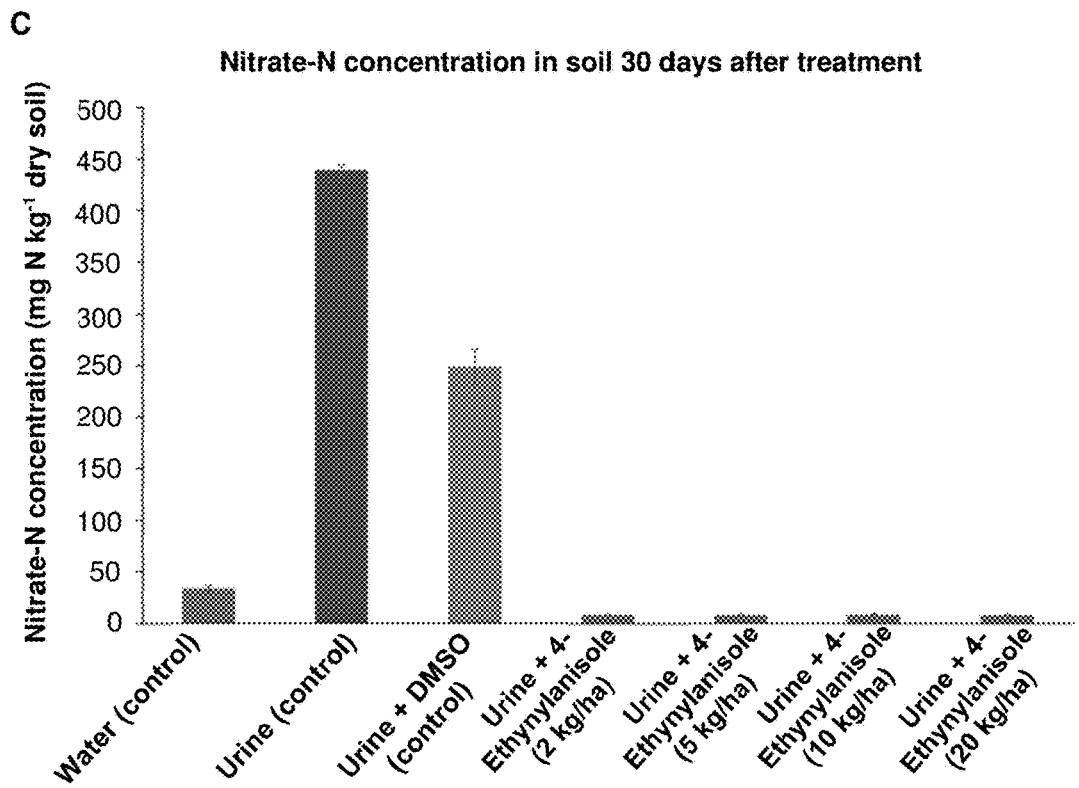
Figure 14:
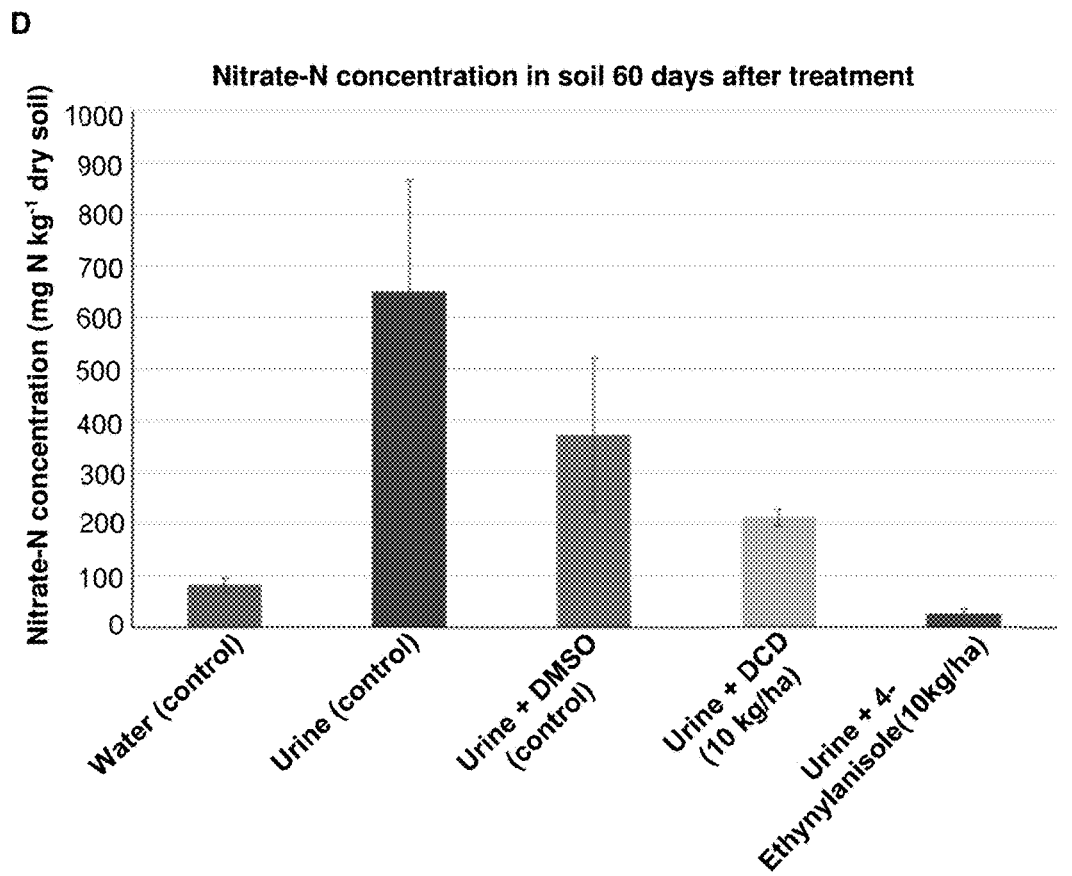
Figure 14:
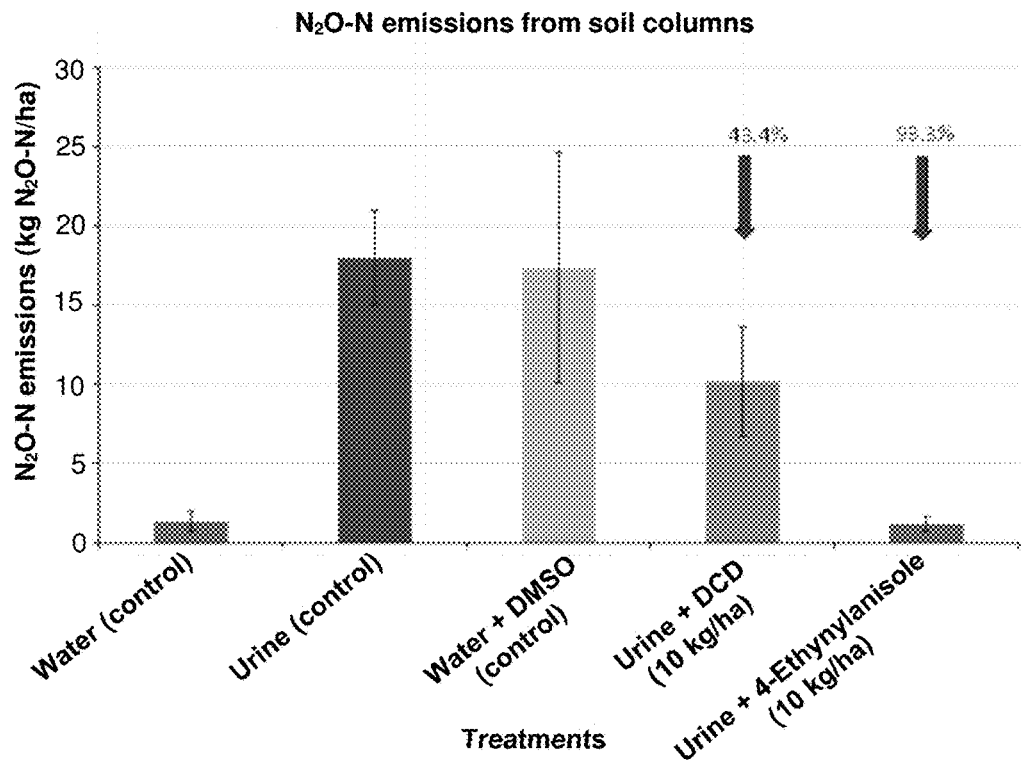
Figure 14:
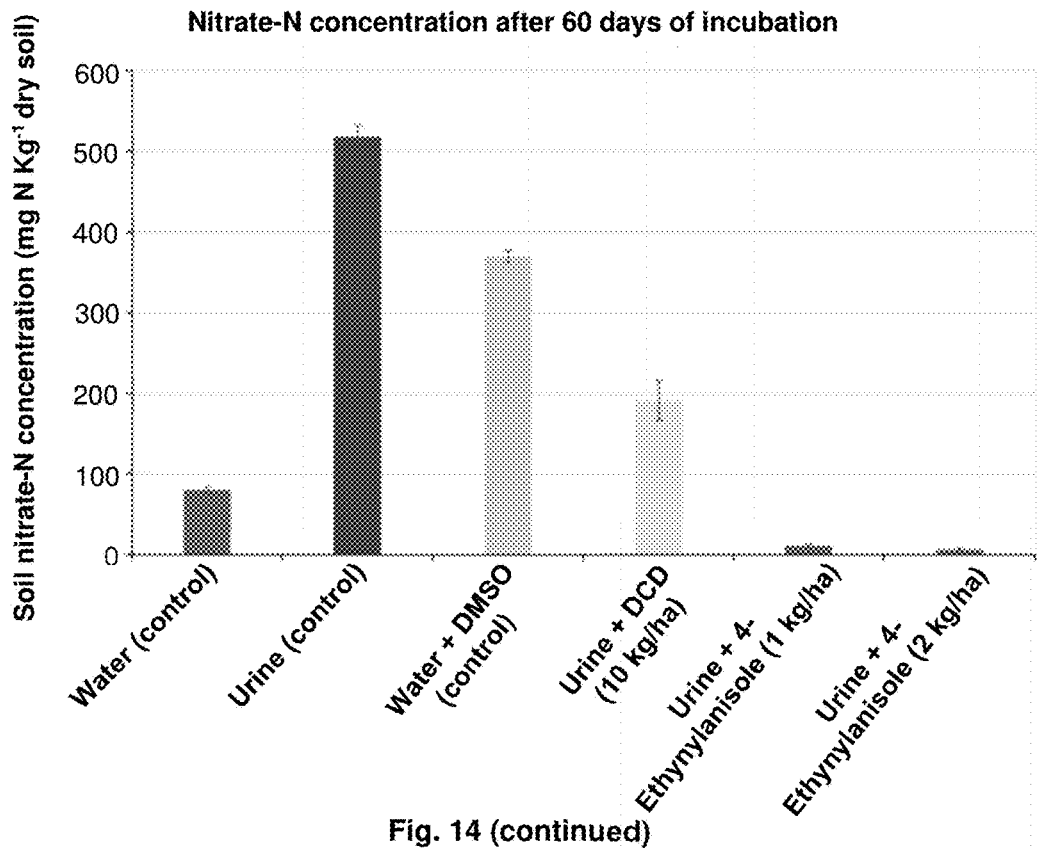
Figure 14:
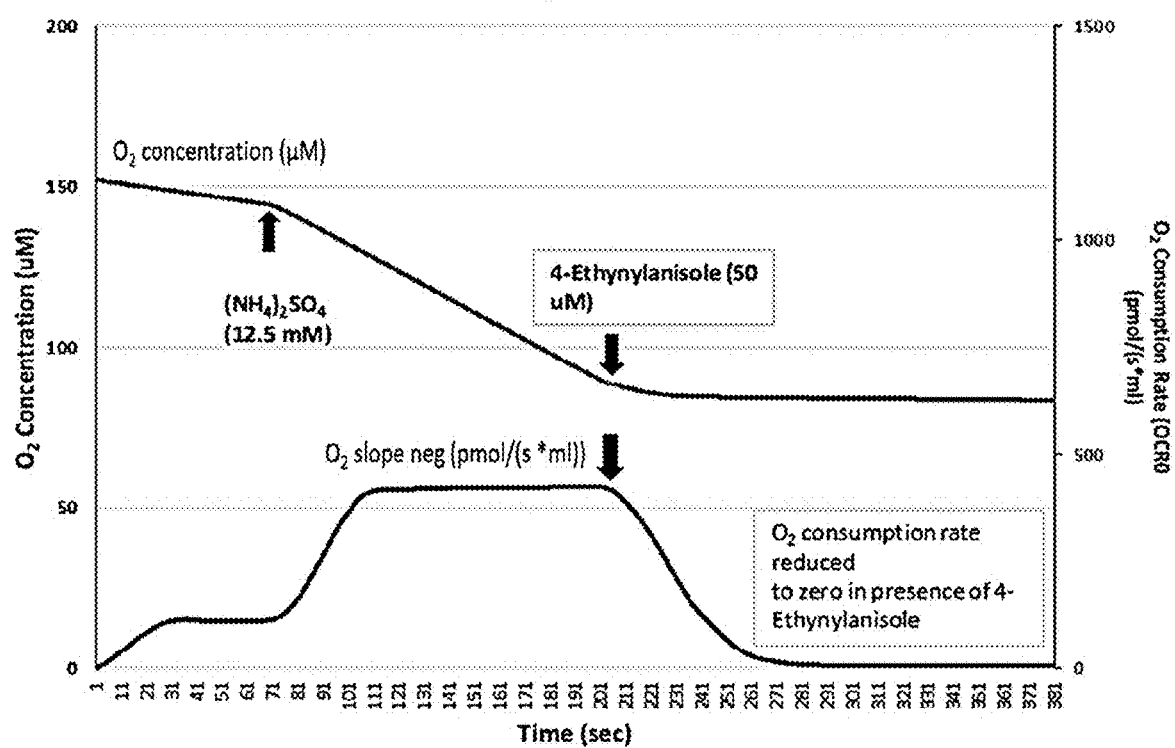
Figure 14:
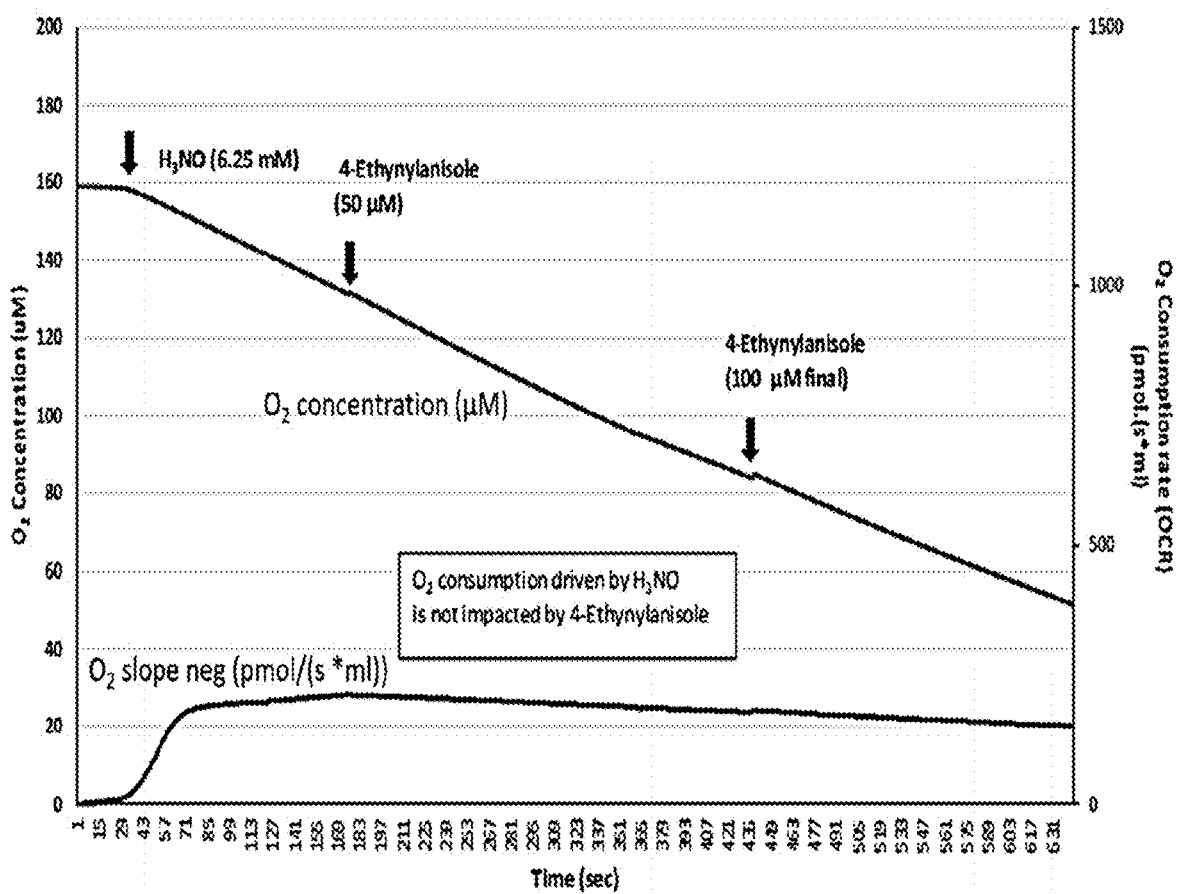

FIG. 14(A) shows that when 4-Ethynylanisole was applied at a wide range of concentrations in in vitro screening, from 1.56 µM to 400 µM, the rate of nitrite production by *Nitrosomonas europaea* was significantly reduced, indicating effective inhibition of the nitrification process by 4-Ethynylanisole. The OD519 nm reading is an indicator of nitrite concentration in the liquid tested, the higher the reading, the higher the nitrite concentration.

The Minimum Inhibitory Concentration (MIC) of nitrite production by 4-Ethynylanisole was determined to be 25-50 µM. The IC$_{50}$ (the concentration of the inhibitor where the nitrite production was reduced by half) was determined to be a very low value of 2.4 µM, showing the high potency of 4-Ethynylanisole for nitrification.

Study 1-14

Laboratory incubation studies were conducted to determine the efficacy of 4-Ethynylanisole in inhibiting nitrification in the soil. A Templeton sandy loam was used in this experiment. 500 g of soil (dry weight basis) was packed into a pottle. Synthetic cow urine with an N concentration of 7 g N/L (comprising about 87% urea-N and 13% glycine-N) was applied to the soil (equivalent to 700 kg N/ha on weight basis, assuming bulk density of 1 g/cm$^3$, top 10 cm). The 700 kg N/ha application was used to simulate the urine-N application rate under a typical dairy cow urine patch in a grazed pasture. 4-Ethynylanisole dissolved in DMSO was applied at a range of rates, 0, 2, 5 10 and 20 kg/ha equivalent to the soil. Control treatments also added to the soil were:

urine alone;
DMSO (equivalent to 0.9 mL/500 g soil)+urine to determine the effect of DMSO on nitrification rate;
water alone (simulating areas of the soil where no urine was deposited).

The urine, water, DMSO and 4-Ethynylanisole treatments were applied to the surface of the soil and the soil was thoroughly mixed. Pottles were covered with lids with breathing holes to allow for gas exchange during incubation. Pottles were incubated at 12° C. Soil moisture content was maintained at field capacity by adjusting on weight basis twice a week.

Soil samples were collected and were then thoroughly mixed and subsamples were extracted in a potassium chloride solute and analysed for mineral-N. Soil moisture content was also determined. Samples were taken at 1, 14, and 30 days.

FIG. 14(B) shows the soil nitrate-N concentration changes with time in the different treatments, showing significant inhibition of nitrate production in the soil by 4-Ethynylanisole at a range of rates.

FIG. 14(C) shows the nitrate-N concentration in the soil at day 30 of incubations, showing significantly lower nitrate-N concentrations in the urine+4-Ethynylanisole treatments, demonstrating the ability of 4-Ethynylanisole to inhibit nitrification in the soil at a range of rates. These results show that when 4-Ethynylanisole is applied to treat urine patches in soil at a range of rates, from 2 to 20 kg/ha, significant reductions in nitrification rate can be achieved. The actual application rate required will depend on the percentage reduction in nitrification inhibition desired and the cost of 4-Ethynylanisole.

Study 2-14

To determine the effect of treating the soil with 4-Ethynylanisole on nitrification rate and nitrous oxide emissions, soil column studies with static gas chambers were conducted. The experiment was conducted in cylindrical PVC containers (Diameter=186 mm, Height=240 mm). The containers were filled with soil to half of the container's height (120 mm), leaving 120 mm headspace. The soil was Templeton sandy loam collected from Lincoln University Research Dairy Farm. It was screened using a 5 mm sieve and air-dried to the required moisture level and packed to bulk density of 1 g/cm3.

The experiment was conducted under controlled conditions. The temperature of the soil columns were maintained at around 12° C. by using a water bath to control the temperature.

The treatments included Control (Water), Control (animal urine), Control (urine+DMSO), Control (urine+DCD at 10 kg/ha) and urine+4-Ethynylanisole (10 kg/ha) in DMSO. Synthetic cow urine was applied at 700 kg N/ha (comprising about 87% urea-N and 13% glycine-N), and 4-Ethynylanisole was applied at 10 kg/ha. There were two sets of cores for each treatment, one set were fitted with static gas chambers with removable lids for nitrous oxide sampling, and the other set used for soil sampling. The urine was sprayed to the surface of the soil simulating urine deposition by a grazing animal; DMSO, or DCD or 4-Ethynylanisole mixed with DMSO was also sprayed onto the urine treated soils to simulate the treatment of urine patches. Nitrous oxide gas measurements followed these treatments—as is detailed further below.

For the soil columns that were set up for taking soil samples for analysis of mineral nitrogen, the different treatments were mixed with the soil for soil sampling. Soil moisture was adjusted to 100% field capacity (FC) and maintained between 80 and 100% FC over the duration of the experiment.

Nitrous oxide (N$_2$O) gas sampling was conducted twice a week using the standard procedure (Di et al., 2007). Vials were evacuated prior to sampling. Three gas samples were taken with 20 minute intervals between each sampling. Sampling frequency was reduced to once a week when N$_2$O fluxes decreased in intensity.

Soil sampling was conducted on Day 1, 7, 14, 30, and 60. The soil samples were analysed for mineral nitrogen.

FIG. 14(D) shows the soil nitrate-N concentration at day 60 of the incubation, showing significantly lower nitrate-N concentrations in the urine+4-Ethynylanisole treatment, demonstrating the ability of 4-Ethynylanisole to inhibit nitrification in the soil. The figure shows that 4-Ethynylanisole was much more potent than DCD in inhibiting the nitrate production by inhibiting the nitrification process. DMSO did not result in statistically significant reductions in nitrate concentration compared with the urine alone treatment (P>0.05).

FIG. 14(E) shows the effectiveness of 4-Ethynylanisole in reducing nitrous oxide (N$_2$O—N) emissions when 4-Ethynylanisole was sprayed to soil surface which had received animal urine. N$_2$O—N emissions in the urine+4-Ethynylanisole treated soil was 93.3% lower than that in the urine (control) treatment. This shows the efficiency of 4-Ethynylanisole in reducing $N_2O$ emissions in the soil. The nitrous oxide reduction by 4-Ethynylanisole (93.3%) was much greater than that by DCD which only gave 43.4% reduction in $N_2O$ emissions.

Study 3-14

To determine the effect of treating the soil with 4-Ethynylanisole at low rates, e.g. at 1 kg/ha and 2 kg/ha, soil column studies were conducted. The experiment was conducted in cylindrical PVC containers (Diameter=186 mm, Height=240 mm). The containers were filled with soil to half of the container's height (120 mm), leaving 120 mm headspace. The soil was Templeton sandy loam collected from Lincoln University Research Dairy Farm. It was screened using a 5 mm sieve and air-dried to the required moisture level and packed to bulk density of 1 g/cm3.

The experiment was conducted under controlled conditions. The temperature of the soil columns were maintained at around 12° C. by using a water bath to control the temperature.

The treatments included Control (Water), Control (animal urine), Control (urine+DMSO), Control (Urine+DCD at 10 kg/ha), Urine+4-Ethynylanisole (at 1 kg/ha) in DMSO, and Urine+4-Ethynylanisole (at 2 kg/ha) in DMSO. Synthetic cow urine was applied at 700 kg N/ha (comprising about 87% urea-N and 13% glycine-N), and 4-Ethynylanisole was applied at 1 or 2 kg/ha equivalent. The treatments were mixed with the soil. Soil moisture was adjusted to 100% field capacity (FC) and maintained between 80 and 100% FC over the duration of the experiment. Soil sampling was conducted on Days 1, 7, 14, 30, and 60. The soil samples were analysed for mineral N.

FIG. 14(F) shows the soil nitrate-N concentration at day 60 of the incubation, showing significantly lower nitrate-N concentrations in the urine+4-Ethynylanisole treatment at 1 or 2 kg/ha, demonstrating the ability of 4-Ethynylanisole to inhibit nitrification in the soil at these low rates. The figure shows that 4-Ethynylanisole was much more potent than DCD applied at the higher 10 kg/ha rate in inhibiting the nitrate production by inhibiting the nitrification process.

Study 4-14

In addition, the inventors have also determined that 4-Ethynylanisole inhibits the oxygen consumption of ammonium-driven metabolism, but not the hydroxylamine-driven metabolism (refer FIG. 1(A)).

To begin to understand the mechanism of action of 4-Ethynylanisole the oxygen consumption rate was measured utilising an Oroborus oxygraphy-2k (Oroboros Instruments). Prior to the experiment, N. europaea cells were grown in ATCC 2265 medium for four days. After which time whole cells of N. europaea were washed extensively as previously described and re-suspended in ATCC 2265 wash buffer (no ammonium) to an $OD_{600}$ of 0.25. Prior to each experiment being initiated by the addition of a metabolizable energy source (ammonium or hydroxyl amine), the oxygen concentration in the assay suspension (2 ml of cells at $OD_{600}$ of 0.25) was equilibrated for 2-3 min with air until a stable signal was obtained. Under normal experimental conditions this typically yielded an oxygen concentration of approximately 220 µM. After the oxygen concentration had stabilised in the Oroborus oxygraphy-2k reaction cell, rubber stoppers were subsequently inserted to enclose the system. To initiate respiration, ammonium sulphate (12.5 mM) or hydroxyl amine (6.25 mM) were injected directly into washed cell suspension of N. europaea. Once a steady oxygen consumption rate was achieved in the presence of either ammonium or hydroxyl amine 4-Ethynylanisole was injected through the rubber stoppers at the concentrations indicated. All measurements were made at 25° C. with stirring at 750 rpm and a data recording interval of 1 $s^{-1}$.

FIG. 14(G) shows that the ammonium-driven oxygen consumption was reduced to zero in the presence of 4-Ethynylanisole, whereas the hydroxylamine ($H_3NO$)-driven oxygen consumption was not affected by 4-Ethynylanisole (FIG. 14(H)). This indicates that the ammonia monooxygenase enzyme (AMO) of the ammonia oxidising bacteria is the potential target of inhibition by 4-Ethynylanisole, not the hydroxylamine oxidoreductase (See equations 2 and 3 above).

Study 5-14

Furthermore, the inventors have also determined that 4-Ethynylanisole does not inhibit other bacteria found in the soil.

To determine if 4-Ethynylanisole specifically targets the ammonium oxidizing bacterium N. europaea we examined the antimicrobial properties of 4-Ethynylanisole against selected bacterial species. Bacteria were routinely grown in Lysogeny broth (LB) (E. coli and B. subtilis), LB-Tween (M. smegmatis), or Rhizobium defined media (G RDM) (M. loti R7A). E. coli, B. subtilis, and M. smegmatis were grown overnight (18 hr) at 37° C. with shaking (200 rpm), whereas M. loti R7A was grown for 48 hr statically at 28° C. 96-well microtiter plates used for the antimicrobial susceptibility testing were set up as follows; 200 µl of media (or as appropriate) was added to column 1 (A-H) and 100 µl of media was added to the remaining wells of a polystyrene 96 well plate. 4-Ethynylanisole was added to column 1 at a concentration of 512 µM (or as required) and serially diluted 2-fold (100 µl transfer) into the neighbouring wells, making sure to discard 100 µl from the last well. Thus, resulting in a serial dilution of each compound. Overnight cultures of bacteria were diluted in fresh media before adding 100 µl of culture to each well of the MIC plate, to achieve a uniform CFU/ml of $\sim 5\times 10^5$ in the MIC plate. Plates were incubated at either 37° C., or 28° C. (with shaking as required) for 18-48 hr before determining the MIC. MIC's were determined as the lowest concentration at which growth did not occur.

The results showed that 4-Ethynylanisole did not inhibit other soil bacteria, such as Mycobacterium smegmatis, Escherichia coli, Bacillus subtilis and Mesorhizobium loti R7A at 4-Ethynylanisole concentrations used in soil to inhibit nitrification to reduce nitrate leaching and nitrous oxide emissions.

Testing 1-ethoxy-4-ethynylbenzene

Study 1-15

A laboratory incubation study was conducted to determine the efficacy of 1-ethoxy-4-ethynylbenzene in nitrification inhibition when applied at a rate of 2 kg/ha. The experimental procedures are the same as described in Study 1-1.

Figure 15:
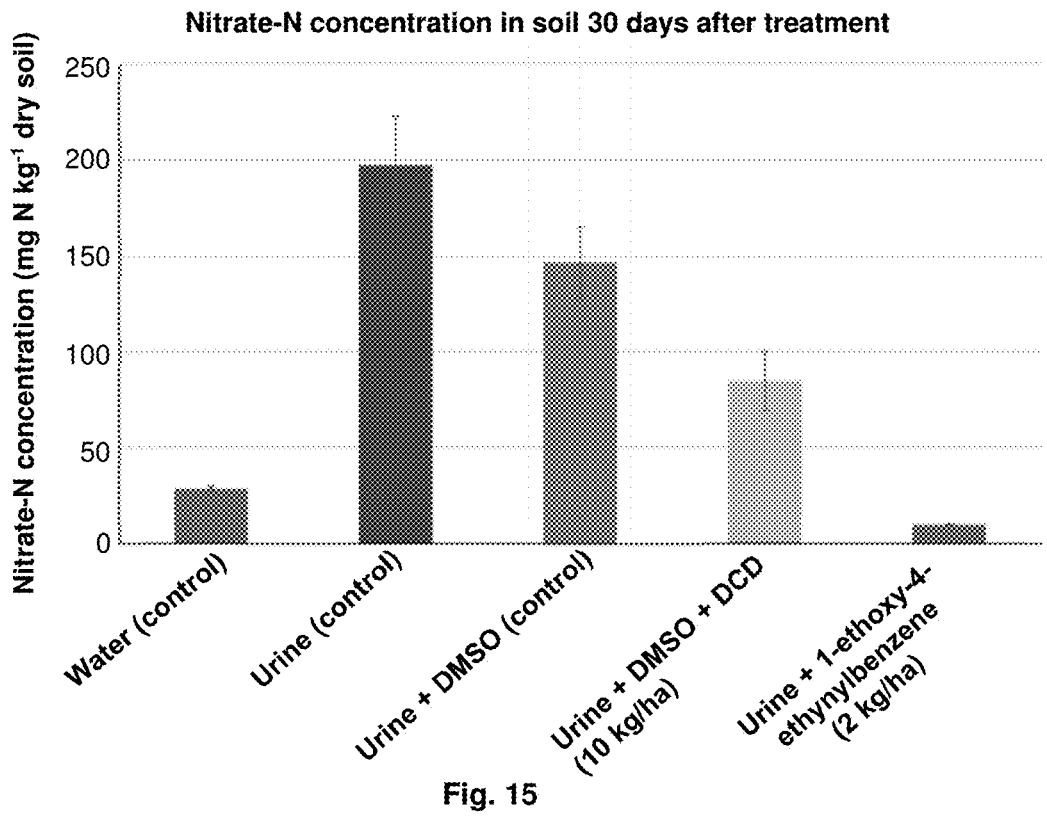
FIG. 15 shows the nitrate-N concentration in the soil at the end of 30 days of incubation, as affected by the application of 1-ethoxy-4-ethynylbenzene at 2 kg/ha, illustrating the highly efficient inhibition of nitrification by 1-ethoxy-4-ethynylbenzene, as shown by the lower nitrate-N concentrations in the urine+1-ethoxy-4-ethynylbenzene treated soil compared with the urine alone or urine+dimethyl sulfoxide (DMSO) control treatments. The error bars represent one standard error of the mean (SEM).

FIG. 15 shows the nitrate-N concentration in the soil at day 30 of incubation, showing significantly lower nitrate-N concentrations in the urine+(1-ethoxy-4-ethynylbenzene dissolved in DMSO) treatment, demonstrating the ability of 1-ethoxy-4-ethynylbenzene to inhibit nitrification in the soil at 2 kg/ha. These results show that when 1-ethoxy-4-ethynylbenzene is applied to treat urine patches in soil at 2 kg/ha, significant reductions in nitrification rate can be achieved. In particular, 1-ethoxy-4-ethynylbenzene at a concentration of only 2 kg/ha was more effective than DCD at a higher concentration of 10 kg/ha at reducing the nitrification rate.

Testing 1,4-diethynylbenzene

Study 1-16

A laboratory incubation study was conducted to determine the efficacy of 1,4-diethynylbenzene in nitrification inhibition when applied at a rate of 2 kg/ha. The experimental procedures are the same as described in Study 1-1.

Figure 16:
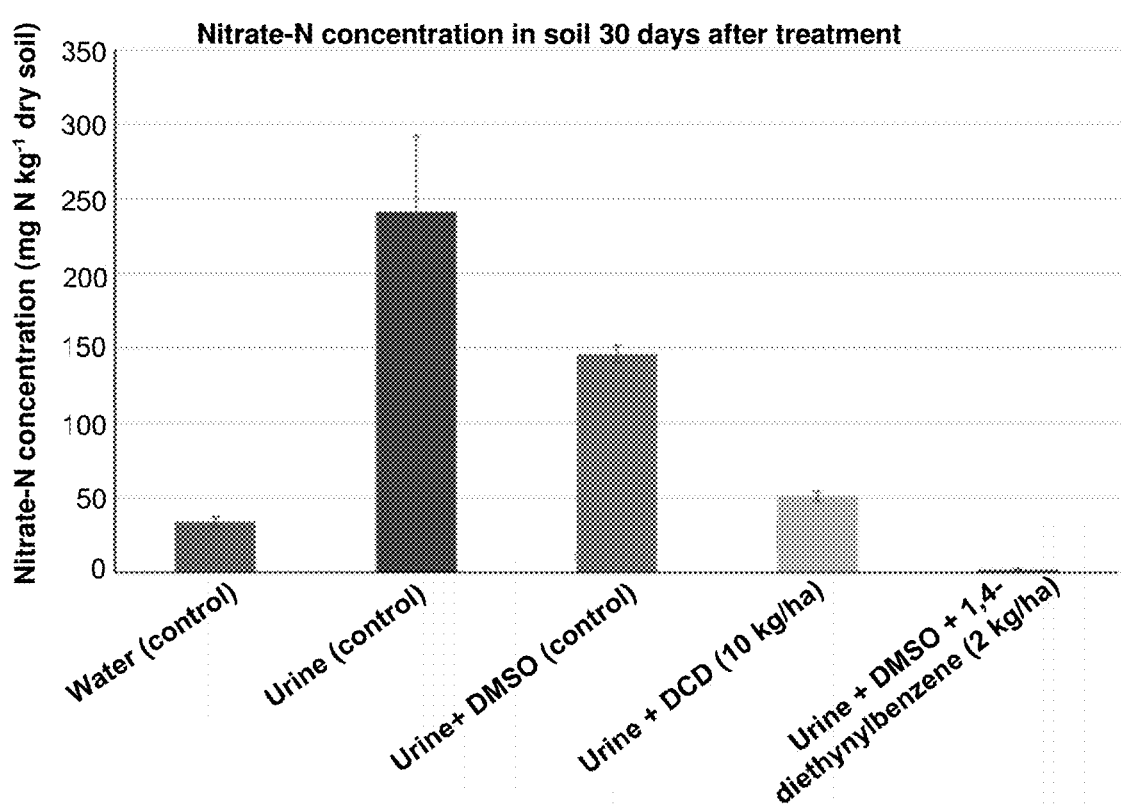

FIG. 16 shows the nitrate-N concentration in the soil at day 30 of incubation, showing significantly lower nitrate-N concentrations in the urine+(1,4-diethynylbenzene dissolved in DMSO) treatment, demonstrating the ability of 1,4-diethynylbenzene to inhibit nitrification in the soil at 2 kg/ha. These results show that when 1,4-diethynylbenzene is applied to treat urine patches in soil at 2 kg/ha, significant reductions in nitrification rate can be achieved. In particular, 1,4-diethynylbenzene at a concentration of only 2 kg/ha was more effective than DCD at a higher concentration of 10 kg/ha at reducing the nitrification rate.

Further Description of the Invention and Ways it can be Implemented

The manufacture of an NNI according to the present invention may involve the packing directly into bulk storage/transportation vessels at the place of manufacture.

In addition, the NNI may be packaged in an amount corresponding to the dose required to certain size of application area. For example, g/m$^2$ or kg/ha.

In some embodiments the storage/transportation vessels may include kg/ha amounts (or other amounts greater than 200 g) with instructions on how to apply to an area of land/plants. The instructions may include information on the amount/type of solvent/solute to provide the desired application dosage and preferred method of application.

The amount for urban use may be generally vended in amounts of 200 g for areas around half an acre (i.e. around 2023 m$^2$) or smaller areas. For example, vending such amounts may be useful for grassed areas such as parks which require N fertilisers to be applied at certain times of the year.

The NNI may be vended in dissolvable bags or containers for ease of preparation for delivery. The invention may also be said broadly to consist in the parts, elements and features referred to or indicated in the specification of the application, individually or collectively, in any or all combinations of two or more of said parts, elements or features.

Importantly, the inventors have found that the NNI can be delivered to the soil using an aqueous medium (such as water, DMSO or effluent) as a carrier in which the Nitrification Inhibitor is dissolved and/or suspended. For example, NNI can simply be sprayed on the soil surface which has received or will receive animal urine or added to a moving stream of liquid to apply to soil.

Alternatively, the NNI may be mixed with a nitrogen fertilizer or coated onto a nitrogen fertilizer, as is known in the art, and then co-applied to the soil.

Alternatively, in another example, NNI may be added in dissolvable bags holding a kg/ha dosage amount for addition to a water source such as an irrigation source or an effluent pond, mixed in with a pond pump, and then delivered when the pond is used to irrigate farmland.

Alternatively, in another example, NNI may be added in solution using a dosing pump to provide a kg/ha dosage amount for addition to a water source such as an irrigation source or an effluent pond, mixed in with a pond stirrer or pump, and then delivered when the pond is used to irrigate farmland.

Thus, NNI described herein truly represents an alternative to DCD which is one of the most widespread commercially used nitrification inhibitors in the world.

The soil can be treated (i.e. impregnated) with NNI in any convenient manner having regard to the properties of a particular NNI and/or area of land to be treated.

For example, depending on the properties of an NNI (or a formulation containing an NNI) it can be:
  mechanically mixed with the topsoil;
  applied to the surface of the soil;
  applied to the surface of the soil and then physically introduced/mixed with the topsoil (e.g. ploughed/disced or otherwise moved/mixed into the soil or washed into the soil by irrigation water);
  coated onto fertiliser granules and co-applied to soil/pasture;
  spayed directly onto land to be treated;
  introduced into irrigation water;
  granulated and delivered to an area of land via a land or aerial hopper apparatus or such like;
  specifically delivering the nitrification inhibitor(s) to a urine patch, or to a specific area of land (e.g. paddock) soon after animals were grazing thereon as part of a rotational grazing program.

However, the above list for how the NNI can be applied to treat the soil should not be seen as limiting.

By way of example if an NNI is to be directly applied onto pasture, the grass is cut, or grazed, to have an average height of around 40 mm to 50 mm. Following application, the treated pasture requires rain or irrigation, ideally within less than 24 hours to 48 hours, to wash the NNI off the grass and into the top-soil.

Advantages of the present invention may also include on or more of the following:
  safe to manufacture and handle;
  providing an alternative nitrification inhibitor to DCD;
  ability to be formulated as a solution or suspension preparation for directly spraying onto soil/land/plants;
  increased nitrification efficacy over DCD at significantly lower kg/ha doses;
  ability to be co-applied with fertilisers;
  ability to be co-applied with irrigation water;
  ability to be co-applied with effluents;
  ability to vary dosage amounts in order to meet certain regulatory targets, relating to nitrate leaching; or nitrous oxide emissions;
  ability to lower dosage amounts and still remain at least as effective as DCD;
  ability to reduce $N_2O$ emissions by more than DCD;
  ability to reduce $NO_3^-$ leaching by more than DCD;
  ability to be delivered by an aqueous carrier;
  ability to be applied by an agricultural spray vehicle or autonomous robot;
  ability to be granulated and delivered by a hopper;
  ability to be mixed into the soil by mechanical means;
  ability to coat fertilizer granules;

It should be appreciated the above list is not intended to be limiting and other advantages may also be inherent in the present invention and aspects thereof detailed herein.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages.

Aspects of the present invention have been described by way of example only and it should be appreciated that modifications and additions may be made thereto without departing from the scope thereof as defined in the appended claims.

REFERENCES

1. Dai, Y., Di, H. J., Cameron, K. C. and He, J. Z. (2013). Effects of nitrogen application rate and a nitrification inhibitor dicyandiamide on ammonia oxidizers and $N_2O$ emissions in a grazed pasture soil. *Science of the Total Environment.* 465: 125-135.
2. Di, Hong Jie and Cameron, Keith C. (2016). Inhibition of nitrification to mitigate nitrate leaching and nitrous oxide emissions in grazed grassland: a review. J Soils Sediments (2016) 16:1401-1420.
3. Di H J, Cameron K C (2002) The use of a nitrification inhibitor, dicyandiamide (DCD), to reduce nitrate leaching and nitrous oxide emissions in a simulated grazed and irrigated grassland. Soil Use Manag 18:395-403.
4. Di, H. J., Cameron, K. C. and R. R. Sherlock (2007). Comparison of the effectiveness of a nitrification inhibitor, dicyandiamide (DCD), in reducing nitrous oxide emissions in four different soils under different climatic and management conditions. *Soil Use and Management* 23: 1-9.
5. De Klein, C., Cameron, K. C., Di, H. J., Rys, G., Monaghan, R. and Sherlock, R. R. (2011). The effect of long-term use of the nitrification inhibitor DCD on reducing $N_2O$ emissions from cow urine. *Animal Feed Science and Technology* 166-167, 480-491.
6. Griess, P. (1879). Bemerkungen zu der abhandlung der H. H. Weselsky and Benedikt "Ueber einige azoverbindungen." *Chem. Ber.* 12, 426-8.
7. Tisdale, Samuel L.; Nelson, Werner L.; Beaton, James D. (1985), Soil fertility and fertilizers, New York: Macmillan, pp. 161-168, ISBN 0-02-420830-2

What is claimed is:

1. A method of inhibiting nitrification in fertilizer, soil, urine, a urine patch, an effluent, manure, waste water, water, a plant or other medium, carrier, or animal comprising a step of adding, using or introducing a compound selected from the group consisting of:
   2-Ethynyl 1,3 Diazine;
   3-Ethynyl 1,5 Diazine;
   4-Ethynylpyrimidine;
   2-Ethynyl-5-methoxypyrimidine;
   5-Ethynyl-2-methoxypyrimidine;
   2-ethynyl-5-methoxypyridine;
   5-ethynyl-2-methoxypyridine;
   3-ethynylpyridine 1-oxide;
   3-Ethynylpyridazine;
   3-Ethynyl-6-methoxypyridazine;
   2-ethynylpyrazine;
   2-Ethynyl-5-methoxypyrazine;
   4-Ethynylanisole;
   1-ethoxy-4-ethynylbenzene; and
   1,4-diethynylbenzene;
directly or indirectly to the fertilizer, the soil, the urine, the urine patch, the effluent, the manure, the waste water, the water, the plant or the other medium, carrier, or animal.

2. The method of claim 1, wherein the compound is applied indirectly to the soil via a solid or liquid carrier.

3. The method as claimed in claim 2 wherein the carrier is a solid or liquid fertilizer.

4. The method as claimed in claim 3 wherein the fertilizer is urea or another fertilizer that contains or produces ammonium or ammonia.

5. The method as claimed in claim 2 wherein the carrier is water, effluent, animal urine or manure.

6. The method of claim 1 comprising applying the compound to a urine patch.

7. The method of claim 6, wherein the compound is applied to the urine patch via an agricultural spray vehicle or autonomous robot.

8. The method as claimed in claim 7 wherein the agricultural spray vehicle or autonomous robot has apparatus thereon for detecting urine patches.

9. A method, as claimed in claim 1, wherein the compound has a dosage rate when applied to soil of 2 kg/ha.

10. A method, as claimed in claim 1, wherein the compound is selected from the group consisting of:
    2-Ethynyl 1,3 Diazine;
    3-Ethynyl 1,5 Diazine;
    4-Ethynylpyrimidine;
    2-Ethynyl-5-methoxypyrimidine;
    5-Ethynyl-2-methoxypyrimidine;
    2-ethynyl-5-methoxypyridine;
    3-ethynylpyridine 1-oxide;
    3-Ethynylpyridazine;
    3-Ethynyl-6-methoxypyridazine;
    2-Ethynyl-5-methoxypyrazine; and
    4-Ethynylanisole;
    and has a dosage rate when applied to soil of 1 kg/ha.

11. A method, as claimed in claim 1, wherein the compound is selected from the group consisting of:
    2-Ethynyl 1,3 Diazine;
    3-Ethynyl 1,5 Diazine;
    2-ethynyl-5-methoxypyridine;
    3-ethynylpyridine 1-oxide; and
    3-Ethynylpyridazine;
    and has a dosage rate when applied to soil of 0.5 kg/ha.

12. The method as claimed in claim 1 wherein the selected compound has a dosage rate when applied to soil between 1 kg/ha to 9 kg/ha.

13. The method of claim 1, wherein the compound reduces nitrate leaching or nitrous oxide emissions from soil nitrogen or nitrogen added to soil, wherein the soil nitrogen or the nitrogen added to the soil contain or produce ammonium or ammonia.

* * * * *